United States Patent [19]

Nottingham et al.

[11] Patent Number: 4,757,716
[45] Date of Patent: Jul. 19, 1988

[54] BORESONIC INSPECTION SYSTEM

[75] Inventors: Lawrence D. Nottingham, Charlotte, N.C.; Thomas E. Michaels; Jennifer E. Michaels, both of Freeville, N.Y.

[73] Assignee: Westinghouse Electric Corp., Pittsburgh, Pa.

[21] Appl. No.: 117,918

[22] Filed: Nov. 6, 1987

Related U.S. Application Data

[63] Continuation of Ser. No. 879,015, Jun. 26, 1986, abandoned.

[51] Int. Cl.⁴ .......................................... G01N 29/04
[52] U.S. Cl. ................................. 73/623; 73/865.8; 904/44
[58] Field of Search ...................... 73/621, 623, 865.8, 73/866.5; 128/660; 310/336; 901/1, 44; 318/626; 376/249; 356/241

[56] References Cited

U.S. PATENT DOCUMENTS

| | | | |
|---|---|---|---|
| 3,021,706 | 2/1962 | Cook et al. | |
| 3,221,544 | 12/1965 | Gunkel | |
| 3,415,110 | 12/1968 | Cowan | |
| 3,575,044 | 4/1971 | Gibbs | |
| 3,583,211 | 6/1971 | Brech | |
| 3,810,384 | 5/1974 | Evans | |
| 3,845,463 | 10/1974 | Timbs | 73/623 X |
| 3,952,581 | 4/1976 | Gottelt | |
| 3,960,006 | 6/1976 | Smith | |
| 4,229,796 | 10/1980 | Garrett | 364/507 |
| 4,304,134 | 12/1981 | Rouse et al. | 73/634 |
| 4,311,556 | 1/1982 | Iwamoto et al. | 901/44 X |
| 4,441,369 | 4/1984 | Lessard et al. | 73/602 |
| 4,460,920 | 7/1984 | Weber et al. | 73/623 X |
| 4,581,938 | 4/1986 | Wentzell | 73/623 |
| 4,597,294 | 7/1986 | Brill, III et al. | 73/623 |
| 4,619,143 | 10/1986 | Franken | 73/598 |

FOREIGN PATENT DOCUMENTS 664763  1/1952  United Kingdom .

OTHER PUBLICATIONS

F. Ammirato, "Ultrasonic Inspection of In-Service Shrunk-On Turbine Wheels", Apr. 1981, *Materials Evaluation*.

Krautkramer, J., "Ultrasonic Testing of Materials", 2nd Ed., Springer-Verlag, 1977, p. 456.

(List continued on next page.)

Primary Examiner—Jerry W. Myracle
Attorney, Agent, or Firm—D. C. Abeles

[57] ABSTRACT

An immersion based ultrasonic inspection system is disclosed which is used to interrogate the bore and near bore material of turbine and generator rotors by passing ultrasonic search units through the rotor bore. This system utilizes variable focus array inspection transducers in a shear mode inspection of the near bore material. A ranging transducer is provided which is used to correct the surface time of the inspection beam. A mapping transducer and blind bore sensor allow diameter mapping of the rotor bore as well as a blind rotor end sensing as the scan head carrying the transducers enters the bore. A scan head centering device or chuck deploys four radial arms to center and support the scan head. Each arm has a roller attached to the end which contacts the bore and rolls along so that the bore will not be damaged as the scan head passes through the bore. The chuck is driven by an electric motor and coupled to a resolver allowing the chuck to be adjusted according to bore geometry mapped by the mapping transducer. The chuck includes a pneumatic disengagement device for fail-safe disengagement of the centering arms to allow retrieval of the scan head in the event of motor or wiring failure. The chuck also includes cable pathways for control cables for the various scan head motion axes. An inspection transducer carriage is provided that provides three axes of motion to the inspection transducer. A radial motion is provided by two radial support assemblies driven by an electric motor and coupled to a resolver allowing radial position to be accurately determined.

28 Claims, 46 Drawing Sheets

OTHER PUBLICATIONS

H. S. Brooks, A. W. Brown, A. C. Rankin; "Ultrasonic Inspect. of the Nimrod Power Plant Alternator Rotors"; Proc. of the 4th Int'l. Conf. on Non-Destructive Testing; London, Sep. 9-13, 1963; pp. 196-202.

G. J. Posakony; "Ultrasonic Tech. for Remote Inspect. of Nuclear Reactor Vessels"; Periodic Inspect. of Pressure Vessels Conf.; London; May 9-11, 1972; IME, pp. 119-125.

J. N. Baez, C. Venturino, O. Wartman; "In-Service Inspect. Sys. for the 1st Arg. Atomic Power Plant"; Per. Inspect. of Press. Vessels Conf.; London; May 9-11, 1972; IME; pp. 97-101.

SWRI Proj. 17-3286-01, Fin. Rep., V. I.; "Jan. 1972 Inserv. Exam. of San Onofre Nuc. Gen. Stat., Unit 1"; So. Calif. Edison Co.; Apr. 1972, pp. 1-32; A-1-B-5.

"San Onofre Nuc. Gen. Stat. Unit 1 Anal. of 2nd Surveillance Mater. Capsule"; So. Calif. Edison Co.; Jul. 1972, pp. 1-15.

"Jan. 1972 San Onofre Nuc. Gen. Stat. Unit 1 Nondestructive Inserv. Inspect."; So. Calif. Edison Co., Jul. 1972, pp. 1-21.

"In-Serv. Inspect. Tool for Nuc. Reactor Vess."; H. W. Keller, D. C. Burns, T. R. Murray; Conf. on Per. Inspect. of Press. Vess.; London; May 9-11, 1972; IME, pp. 126-139.

"Mech. Equip. for Inserv. Inspect. of Nuc. Reac."; C. E. Lautzenheiser; Conf. Per. Inspect. of Press. Vess.; London; May 9-11, 1972; IME; pp. 205-220.

"Boresonic Inspect. of Forged Turbine & Gen. Rotors"; W. R. Marklein, R. E. Warnow; ASMEP 65--WA/PWR-2; ASMEWA Meeting, N.Y., 11/29-12/4, 1964.

"Inserv. Inspect. of San Onofre Nuc. Gener. Stat. Unit 1,2,3"; C. G. Johnson, D. Albertstein, O. J. Ortega, C. E. Lautzenheiser; ASMEP 70-WA/NE-5; ASMEWA Mtg., N.Y., 11-29 to 12-3, 1970.

"Rev. of the Tech. of Inserv. Inspect."; C. E. Lautzenheiser, III, Inter-American Conf., Feb. 1972.

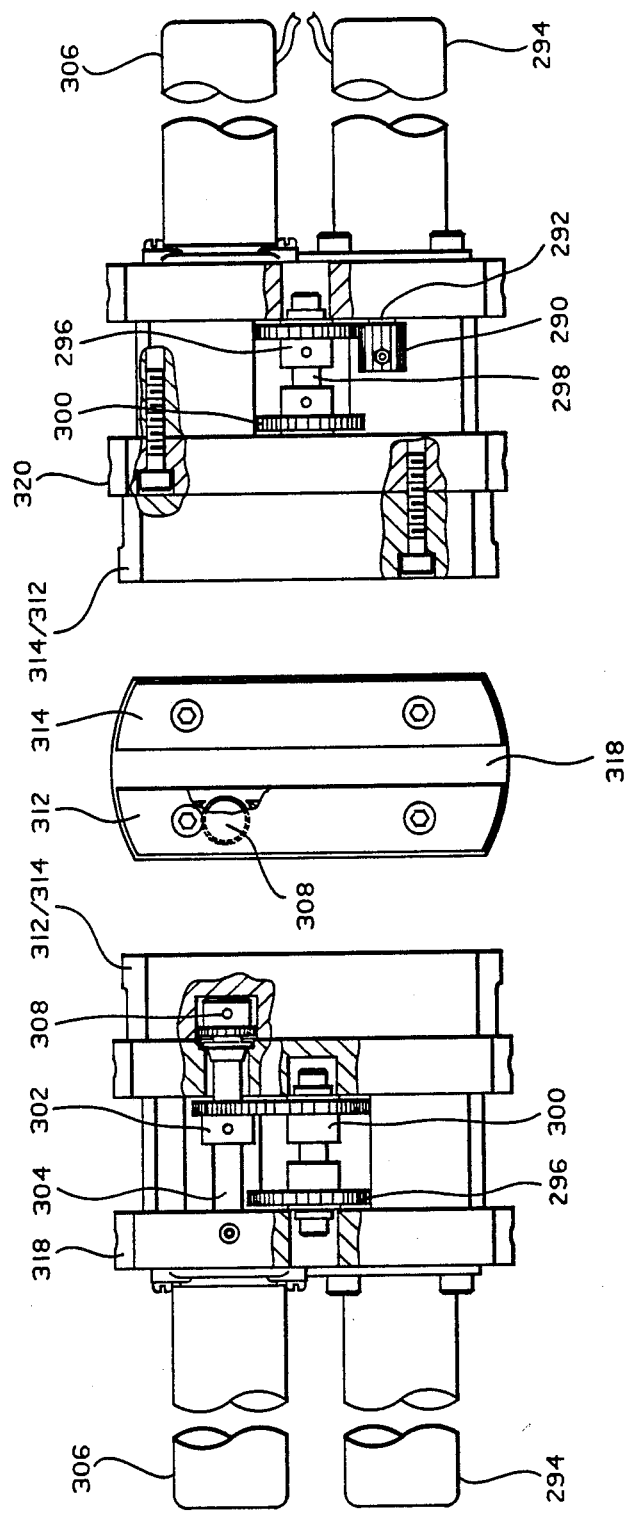

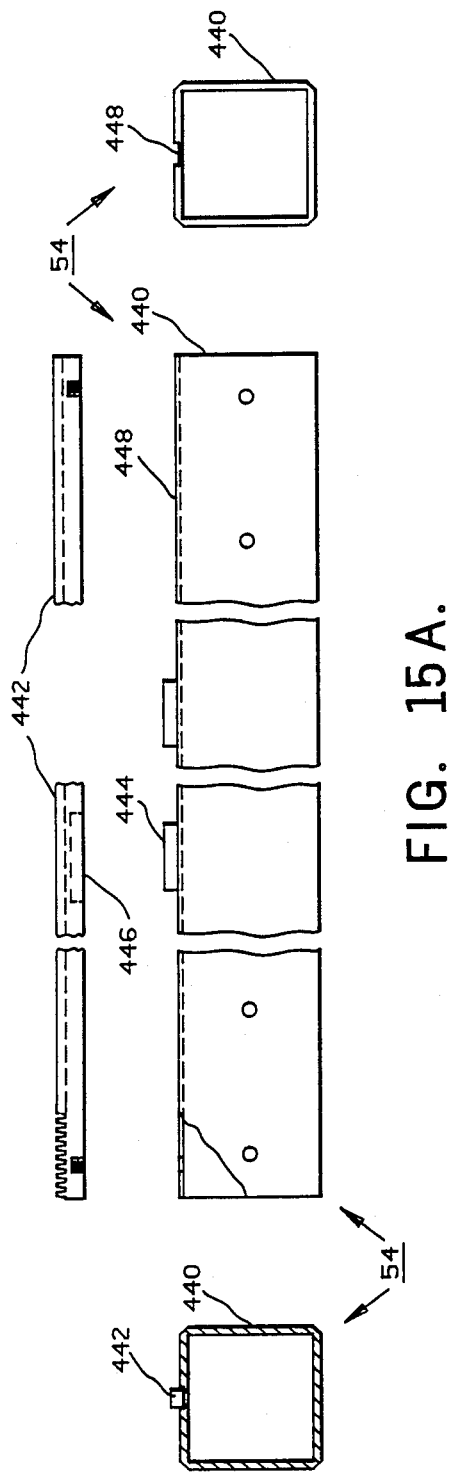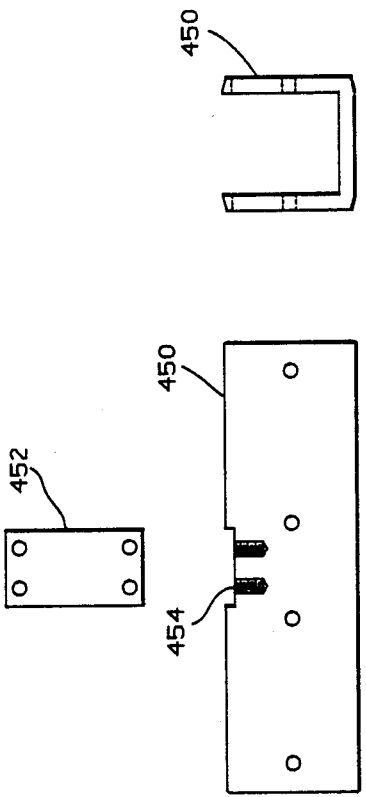

BORESONIC INSPECTION SYSTEM

This application is a continuation of application Ser. No. 879,015 filed June 26, 1986, now abandoned.

CROSS REFERENCES TO RELATED APPLICATION

This application is related to concurrently filed U.S. applications assigned to Westinghouse and entitled Ultrasonic Signal Processing System Including a Flaw Gate by the inventors of the invention described herein and having U.S. Ser. No. 878,817 and entitled Bore Mapping and Surface Time Measurement System by the inventors of the invention described and having U.S. Ser. No. 878,649. The above-mentioned applications are incorporated by reference herein. This application is also related to copending U.S. applications entitled Apparatus for Ultrasonically Inspecting a Large Shaft from a Liquid-Filled Bore and entitled Water Treatment System for Ultrasonic Inspection of Turbine Rotors from the Bore having U.S. Ser. Nos. 844,499, now U.S. Pat. No. 4,699,008, and 862,332, now U.S. Pat. No. 4,670,029, respectively.

BACKGROUND OF THE INVENTION

The present invention is directed to an inspection system for ultrasonically inspecting a material such as metal, and, more particularly, the present invention is directed to a boresonic inspection system which performs shear mode inspection of near bore material in turbine and generator rotors by passing ultrasonic search units through an axial rotor bore.

For many years, there has been increasing interest in, and a growing demand for, equipment and methods which can be used to inspect power generation turbine and generator rotors for possible material discontinuities or degradation which could lead to premature, and possibly catastrophic, failure of these components and which allow rotor life extension where appropriate. The consequences of a sudden, catastrophic failure of such a component would be severe, certainly in financial terms and possibly in terms of human looses. The center portion of the steel forgings from which these rotors are made, by the very nature of the manufacturing process, is perhaps the most suspect material in the rotor in terms of naturally occurring discontinuities and other material disorders. This is, in fact, one reason that a central bore hole is machined through most rotors in an attempt to remove this suspect material. In addition, the operating conditions at and near the central bore holes in rotors can lead to service related disorders such as thermal creep, fatigue and thermal embrittlement, especially in the presence of inherent forging discontinuities. Thus, there is a great interest in rotor inspection capabilities.

Several nondestructive test methods have been developed for use in interrogating the bore and near bore regions of rotor forgings. When the forging is new and before the final machining has taken place, it is still cylindrical or near cylindrical in shape and ultrasonic inspection from the outside has proven to be a valuable tool. However, because of the complex geometries which characterize the outer peripheries of completely machined forgings, ultrasonic inspection from the outside is impractical for inspecting rotors once they are machined. Other methods such as visual and magnetic particle examination have been used successfully to inspect the bore, but these methods are only sensitive to discontinuities which intersect or are very near to the bore and then only yield a two dimensional view of the material and any detected discontinuities.

Since the early to mid 1970's, ultrasonic inspection from the rotor bore itself has gained fairly wide acceptance as a viable volumetric inspection method. In this method, which has become known as boresonic inspection, the ultrasonic transducers are transported through the central bore hole by some convenient method and the ultrasonic beams are directed from the bore surface into the rotor material. The ultrasonic wave can penetrate well into the rotor material, and by collecting, processing, and observing any reflections of the wave which occur within the forging, one can get some idea of the integrity of the material. Volumetric inspection is achieved by scanning the transducers around the circumference and along the length of the bore while directing the ultrasonic beam into the material so that the beam has been ultimately passed through all of the material of interest.

Early borosonic test systems and some still in use, such as that described in U.S. Pat. No. 3,960,006, are based on conventional, contact ultrasonic practices. In a contact system, Plexiglas shoes (or shoes made of a similar material) are ground to the exact curvature of the bore being inspected and are mounted on the ultrasonic transducers. The search units (transducers with shoes attached) are then operated in direct contact with the bore surface, with some viscous liquid couplant medium spread over the surface to enable sound transmission from the shoe into the metal. The transducers themselves contain piezoelectric elements which generate ultrasonic waves in the compressional, or longitudinal, mode in the shoe. If a longitudinal wave is desired in the metal, the transducer element is oriented in a plane parallel or nearly parallel to a bore tangent plane; in other words, so that the incident wave in the shoe is aimed nearly radially at the bore. If an angled shear wave is desired in the metal, the plane of the search unit shoe onto which the transducer is mounted, is inclined relative to the bore tangent plane such that a refracted shear wave is produced at the shoe/metal interface. In other words, the incident wave in the shoe is not normal to the bore surface. The geometry can be such that the refracted wave travels at an angle somewhere between radial and tangential while remaining in a plane perpendicular to the bore axis (tangential aim shear), at an angle somewhere between radial and axial while remaining in a plane cut through the bore axis (axial aim shear), or a combination of the two. Typically, the refracted shear wave is on the order of 35° to 70°. Angled compressional wave interrogation can also be employed but this is not standard practice.

In a conventional contact ultrasonic system, the emitted wave travelling through the rotor material is divergent; that is, the wave front grows in size as it moves away from the source. The intensity of this wave therefore decreases with increasing travel distance (since the area covered by the wave is increasing) and therefore, the intensity of a wave returning from a given reflector decreases with increasing distance of the reflector from the search unit. Also, since most reflectors are small relative to the area (bem size) covered by the wave, the size of the reflector affects the intensity of the reflected wave. These principles have been long known and understood in ultrasonic testing in general and are used to provide an estimate of the size of an unknown reflector.

The intensity of a reflected wave is normally converted, through the piezoelectric property of the transducer element, to a voltage which is then linearly presented as a signal amplitude on a cathode ray tube type presentation. Distance/Amplitude and Area/Amplitude relationships are determined using known reflectors in reference standards under conditions which reproduce or, at least, simulate the prevailing test conditions (bore curvature, attenuation, etc.). The total inspection system, including the search unit, transmit and receive electronics, amplifiers, displays, cables, etc., are calibrated using the known, artificial reflectors in a reference standard. Reflectors are considered to be reportable when their amplitudes exceed a specific amplitude limit which normally includes the Distance/Amplitude correction. Its size is estimated using the established Area/Amplitude relationship.

Most, if not all, of the existing boresonic test systems incorporate some sort of mechanical transport system to deliver the transducers into and along the bore. In general, these transport systems have three things in common: some mechanism, normally hydraulic or pneumatic, is used to properly position the test head within the bore; the transport system provides a means by which the transducers are held against the bore surface; and the system incorporates a scanning mechanism through which complete coverage of the bore is achieved. Other features such as automatic couplant feed have been added to some systems.

Some of the disadvantages associated with boresonic test systems using contact transducers are as follows:

1. Maintaining intimate contact between the search unit and the bore surface is a constant problem and the results of not doing so are severe and nonconservative. Any loss of contact results directly in blind areas within the rotor from which no useful data are obtained; in other words, reflectors can be inadvertently missed. Furthermore, partial loss of contact and even contact pressure fluctuations result in partial wave loss and therefore in erroneous amplitude measurements and erroneous reflector size estimates. In an attempt to overcome this deficiency, developers have instituted hard to meet requirements for extremely smooth and uniform bore surfaces. Another aid in minimizing this problem has been the development of compliant transducer transport fixtures which will follow the bore contour while maintaining contact with it.

2. Contact ultrasonic inspection in general, and as applied to boresonic inspection in particular is limited in its ability to detect reflectors lying at or near the surface from which the test is being conducted. Even if a reflector is detected, size estimates can be very inaccurate. For rotors, this is especially significant since the stresses and probability of having flaw or discontinuity indications are both highest at the bore surface and decrease with distance away from the bore. This near surface capability limitation is due primarily to two factors. First, is the effect of the shoe between the transducer and the bore surface. Part of the sound which is generated by the transducer is reflected back into the shoe at the interface of the shoe with the metal. This is a natural occurrence which results from the different acoustic properties of the two materials. This sound continues to reverberate in the shoe, with some escaping each time it strikes a boundary, until it eventually decays to an insignificant level. Until it reaches this level, however, a signal is generated each time the sound wave strikes the transducer. These signals appear to be located at or beyond the shoe/rotor interface and mask any real reflections that originate in rotor material but that are received during the time period of the unwanted reverberations. Although much has been done to eliminate or at least minimize this effect, the first ¼ inch of rotor material is normally considered to be uninspectable. The second factor has to do with the near field characteristics of the sound beam. As a wave propagates away from the transducer, its characteristics undergo certain changes. Near the transducer, the beam is characterized by pressure maxima and minima which arise due to constructive and destructive interference of the wave front as it is forming. As the wave travels away from the transducer, the pressure fluctuations decrease, both in number and in relative magnitude until, a point is reached at which a uniform, divergent beam has been formed. This point is defined as the near field limit. The Distance/Amplitude and Area/Amplitude relationships discussed earlier can only be developed in, and are therefore only useful in, the presence of a uniform wave front. The exact point at which this occurs is a function of several variables, of which transducer size and frequency are the most significant. In general, however, the ability to detect reflectors lying near the test surface is considered to be extremely unreliable, at best.

3. Contact inspection is limited in its ability to accurately size real reflectors. Ideal reflectors, commonly flat bottom holes (with the beam normal to the flat) and side drilled holes (with the beam normal to the hole axis), are used to develop the Distance/Amplitude and Area/Amplitude relationships used for detecting and sizing reflectors with a divergent beam transducer. Since any given reflector geometry has its own reflectivity, these relationships are only valid for the type of reflector from which they were derived. Therefore, the use of a given set of relationships developed on, for example, flat bottom holes will not be accurate for other specific geometries such as spheres, off-axis discs, elliptical notches, etc. The problem is compounded further when considering irregular, randomly oriented reflectors characteristic of real reflectors in real materials. It is for this reason that size estimates for such reflectors are normally given in terms of equivalency to the ideal reflectors used to develop the calibration relationships (such as Equivalent Flat Bottom Hole Area) and do not necessarily reflect the actual size.

4. Compliant transducer support systems used to improve surface contact contribute directly to inaccuracies in estimates of the position of a reflector. Reflector position is determined from a combination of the transducer position, the beam direction, and the time of flight of the wave from the time the transducer is pulsed until the reflection arrives. A soft mechanical support system can affect the accuracy of the transducer position as well as the beam direction.

5. Resolution, as used in ultrasonic testing, is defined as the ability to discriminate between two reflectors lying in close proximity to one another. Because the ultrasonic beam in a contact system is divergent, resolution is very poor. This means, for example, that a number of relatively small reflectors could be reported as one larger reflector, an error which could affect the analysis and final disposition of the rotor.

6. Since the beam is divergent with the pressure decaying with increasing distance from the transducer, sensitivity falls off sharply with increasing depth.

More recently, a new direction regarding bore ultrasonic inspection of rotors has begun to emerge. A test system, known as TREES (Turbine Rotor Examination and Evaluation System) has been developed under the direction of the Electric Power Research Institute (EPRI) for the American Electric Power Company. This test system is the first known rotor bore inspection system to provide inspection capability based upon immersion ultrasonic testing techniques. For the purpose of this writing, TREES is categorized as a fixed focus immersion system.

Fixed focus immersion systems provide certain features which overcome many of the shortcomings of the contact systems. The transducers operate in an immersion bath which eliminates many, if not all, of the contact problems. No transducer shoes are required as the water provides a path for the sound to travel from the transducer to the rotor. The transducer can be offset from the bore by an amount which provides for the near field effects to occur entirely in the water so that the beam is formed and well behaved at the bore surface and beyond. Generation of either angled compressional or shear waves in the rotor can be easily accomplished by simply tilting the transducer such that the beam strikes the bore surface at other than normal incidence.

Focussing of the ultrasonic beam can be accomplished by fitting a lense to the transducer. The outer surface of the lense is concave and the exact geometry can be designed to achieve the desired results. For example, the lense can be spherically or cylindrically concave depending on the desired spot size geometry. The lense can also include correction for the effects of material geometry on the beam, such as correction for the focussing effect of striking a cylindrical bore surface. By carefully designing the lense geometry, in combination with a specific stand off distance from the test surface, the depth within the material at which the beam will be in focus can be controlled. Adding a focussing capability is the most significant advantage offered by using immersion ultrasonic technology. By utilizing carefully designed lenses, the ultrasonic beam can be reduced in size over some effective focal length in the material. This results in a small, high intensity beam which yields significant improvements in both sensitivity and resolution. In addition, using highly focussed beams improves the accuracy of reflector size estimates. Instead of using amplitude as compared to some ideal reflector, the reflector can be outlined by scanning the finely focussed beam across the reflector. Because the beam is small and of high intensity, reflections can be obtained from relatively poor reflecting surfaces of a reflector, thereby improving the accuracy of the size estimate. This also yields shape information which is generally unavailable from contact testing.

The primary disadvantage of a fixed focus system is that the beam only retains the high intensity, small spot size over a limited depth range. To achieve volumetric inspection with conventional immersion transducer technology, a number of specifically designed transducers must be used. In the TREES system, for example, 12 transducers (6 pairs of tangential aim transducers looking in opposite directions) are required to cover the first four inches of rotor material. When so many transducers are required, it becomes cumbersome to transport them through the bore. One must choose between retaining flexibility by including motion capabilities within the scan head for each transducer, and maintaining the capability of passing all transducers through the bore at one time and thereby performing an inspection in a single scan pass. Multiple scans are not an attractive option due to the time required to do so. Limiting the motion capabilities and crowding the transducers into as small a space as possible limits the capability of inspecting bore geometries other than a straight cylinder. Bottle bores and bottle bore transitions are very difficult to interrogate unless each transducer can be moved to the appropriate position as it passes such areas.

All of the known systems use hydraulically or pneumatically activated, articulated arm devices to move some bore riding feature, normally the shoe, to the bore surface. These have been three arm devices that take advantage of the self-adjusting nature of three contact points in circular cavity. In some of these systems the articulating center mechanism also serves as a transducer housing. There are several disadvantages associated with this type of support system:

1. The mechanical advantage of the articulating arm design, employed because the apparatus must operate in a variety of bore sizes, is variable with bore diameter. That is, when the device is in a small bore and the arms are near to their closed position, it is stiff axially and soft radially. When the same device is in a large bore and the arms are near to their full open position, it is stiff radially and soft axially. Both of these extremes can lead to problems. In a small bore situation, the radial softness can result in an inability of the centering device to fully support the weight of the scan head. In the large bore case, the radial stiffness can result in a radial deflection of the scan head from the nominal bore centerline when bore geometry irregularities such as dimples are encountered. The radial stiffness characteristics are even more important if the centering device is also being used as a transducer positioning device. It must be stiff enough, when at its lowest mechanical advantage, to support the weight of the scan head and hold the transducers in intimate contact with the bore. On the other hand, when at its greatest radial mechanical advantage, it must be soft enough to allow the arms to track the bore even in the presence of irregularities without pulling the scan head away from the bore centerline and applying a bending moment to the scan head. This is a very difficult, if not impossible, compromise to reach, especially over a wide range of bore sizes.

2. If this type of support system is hydraulically or pneumatically actuated, it cannot be adjusted to operate at a specific offset from the bore. The centering mechanism is either engaged or disengaged, depending on the status of the hydraulic of pneumatic pressure.

3. Even if motor driven, the positional accuracy would be reduced by the ratio of the radial displacement to the motor action required to achieve that displacement.

4. The position accuracy of such a device is a function of the bore diameter in which the device is being engaged since the radial motion is achieved by a specific motor action and varies with depth.

5. Uninterrupted support as the device passes steps and tapered bottle bore transitions is difficult to achieve. Typically, supports cannot be engaged in bottle bore transitions because of the irregular geometry which results from the machining done in these areas. Supports definitely cannot be engaged near steps in bores. This means that multiple supports must be included so that some may be disengaged while other are engaged and providing the necessary support. Articulated arms, if long enough to provide for fairly large bores and yet designed to fold in so that they can pass through small bores, require excessive axial space in the scan head, especially when multiple devices are provided.

In prior art contact systems, the mechanism, as mentioned above, which holds the transducers in contact with the bore surface involves one or more articulated arms. In this type of device the transducer is attached, via some pivoting feature, to one end of an arm which lies primarily in the axial direction, that is, along the rotor bore axis. The opposite end of the arm is attached, also via some pivoting feature, to some centrally located housing. An actuator is attached to the arm somewhere along its length and the transducer is moved to and held against the bore by applying a radially outward force via the actuator and allowing the arm to rotate about its attachment to the central housing. The transducer rotates about its pivot as contact is made with the bore surface until it is in complete contact with the bore. The actuator mechanism is either hydraulically or pneumatically driven in the prior art designs. In all but one known case, the articulated arms are arranged in groups of three located at the same axial position and equally spaced around the central housing. This configuration takes advantage of the self-centering capability of three point contact in a circular hole. Transducers can be mounted on any or all of the arms.

In some contact inspection systems, the tranducer locating mechanism also support the scan head and in other systems, scan head support and transducer location have been maintained as separate functions. In all cases, the transducers and scan head support mechanisms are deployed to their operating positions and then the entire assembly is driven through some scan pattern so that the transducers pass over the bore surface.

The second type boresonic system, as mentioned above, involves the application of immersion testing techniques which allow for the use of focussed ultrasonic beams and thereby offer several advantages in terms of sensitivity and resolution. In immersion testing, the transducers operate at a distance from the surface of the material being inspected and an immersion fluid is used to provide for the transmission of the sound from the source (transducer) into the metal and back when a reflection of the sound occurs. In the prior art, immersion-based boresonic inspection systems, the transducers are offset from the bore in a housing. The housing itself operates in contact with the bore and is deployed to the bore from the scan head in a manner similar to the method described for contact testing. However, only a single articulating arm is used and all of the transducers used for an inspection are mounted in a single housing. In this type of support, the transducers must be properly set within the housing so that they are at the appropriate attitudes relative to the surface when the housing is moved to the bore. Once the position of the transducer is set with the housing, it cannot be changed without removing the scan head from the bore.

Many boresonic inspection systems, as discussed above, are based upon contact transducer technology. In such systems, immersion fluid containment is not required and so a seal is not required. For immersion boresonic test systems, a variety of immersion approaches are available. First, one can provide a cavity which contains the immersion fluid around each transducer. This type of water column approach is advantageous in that the entire scan head is not submersed, but it is limited in its ability to track different diameters, tapered transistions, surface irregularities, etc. Another approach which may be taken involves immersing only the portion of the scan head which contains the ultrasonic transducers. This approach requires a seal which moves along the bore with the transducers and yet can seal on a variety of bore sizes. This option is very difficult to perfect. Another option involves immersing the entire bore and moving the circumferential and axial motion drives into the immersion bath. In the prior art immersion systems, the bore is completely immersed and the drive mechanism is designed such that the circumferential motion drive resides in the immersed portion of the scan head and the axial motion drive is outside of the bore but still in the immersion fluid. This solution has several disadvantages, including the following:

1. It is difficult and expensive to waterproof all drive components, especially electrical components such as motors, slip rings, and switches;

2. The use of an immersed circumferential drive mechanism and slip rings limits the quantity of wires which can be carried into the bore. This has an impact on the numbers and types of support devices, ultrasonic transducers, and auxiliary devices which can be placed in the scan head; and 3. The inclusion of the axial drive in the immersion fluid (but remote from the bore) requires a large immersion tank since the axial drive is fairly large and must be very stable. This requires a large volume of water which is harder to handle during various conditioning steps such as air removal, chemical treatment with wetting agents and rust inhibitors, etc.

The exact path along which the transducers move varies considerably for existing systems. One system, the TREES system mentioned previously, uses a continuous helical motion to advance the scan head down the bore as it is continuously rotated. Another manual system, uses a motorized rotation coupled with an air powered actuator for the axial advance. There are several disadvantages associated with the above-mentioned drive systems:

1. The drive system for the TREES scan head uses motors to continuously rotate the transducer assembly and an axial drive to push the entire assembly through the bore. For this type of system, the motor and position encoder for the rotation must be placed near the transducer assembly, and slip ring type connectors must be used to make the electrical connections to the transducers. The slip rings are necessary to permit continuous rotation without cable interference. There are three disadvantages to this type of drive system: A. the motor and position encoser for the rotation must be near the scan head and thus must be small enough to fit into the bore cavity; B. the cross-sectional space required for the rotational drive in the bore severely limits the number of electrical cables that can pass through to the down-bore components such as centering motors, ultrasonic transducers, etc.; and C. slip rings are expensive and often have reliability problems, especially when immersed.

2. The manual boresonic inspection system uses a drive box that is external to the bore and scan head. This drive box is constructed using limit switches and relay logic to produce alternate 400 degree rotations of the scan head. One increment of axial advance is used between each rotation. The axial advance is driven by a solenoid operated, compressed air powered linear cylinder. The solenoid is connected to the relay logic to produce an axial advance at the end of each rotation pass. The main disadvantages with this system are: A.

the motions are neither readable nor controllable by the main computer; B. the incremental advance of the axial drive is fixed such that the system does not have fine positioning capabilities; C. The rotational drive system is belt controlled and does not have sufficient torque to rapidly rotate large unbalanced loads; and D. the drive rods are not held with sufficient rigidity in the drive box to permit accurate readout of the scan head position in the bore.

In the prior art, manual, pneumatic and motor driven inspection systems the control systems that move the scan head and provide position indications have been cumbersome and inaccurate due to resolver locations that require knowledge of mechanical slack in the system and positioning apparatus that does not allow for high resolution positioning. As a result, the location and size of discontinuities and flaws have been inaccurately located. Inaccurate flaw location, requires that remachining to remove flaws cover a larger area than is necessary, weakening the rotor at its highest stress area, near the bore. Inaccurate flaw location also hinders comparison of previous inspections with current inspections because it is difficult to determine whether a given flaw is a new flaws or an old flaw that has been inaccurately located due to alignment inaccuracies.

SUMMARY OF THE INVENTION

It is an object of the present invention to provide a mechanism which accurately positions immersion inspection transducers in a bore.

It is another object of the present invention to provide a system which creates refracted shear waves in a near bore region of a central bore in a rotor.

It is a further object of the present invention to provide a scan head in which primary transducer stations are located at or about the axial center of the scan head with support mechanism located on either end.

It is an additional object of the present invention to provide remotely adjustable motor driven support and centering mechanisms.

It is a further object of the present invention to provide accurately controllable motor drives to allow variable and controllable positioning capabilities for the center of the scan head.

It is another object of the present invention to provide a pneumatic disengagement feature including a proximity sensor to allow collapse of the centering supports and fail-safe retrieval of the scan head.

It is also an object of the present invention to allow the disengagement mechanism to be deactivated so that the centering mechanism is reengaged during preinspection testing.

It is still a further object of the present invention to provide multiple scan head support devices that can be individually retracted to pass dimensional changes in bore size without sacrificing accurate positioning of the transducers in the scan head.

It is yet another object of the present invention to provide a scan head which will operate in blind bores and plugged rotors.

It is an additional object of the present invention to provide an inspection transducer station at the end of the scan head to allow inspection near the blind end of the plugged or blind end bore.

It is another object of the present invention to join the scan head to a drive rod with a mechanism that allows the scan head to be decoupled from drive rod sag and other lateral loads on the scan head.

It is an object of the present invention to provide transducer motion capabilities within the scan head.

It is still another object of the present invention to allow a rotor being inspected to be tilted to aide in removing air from the bore.

It is a further object of the present invention to provide plural motor driven motion axes to accurately position ultrasonic transducers in a rotor for an ultrasonic inspection.

It is an object of the present invention to provide resolvers coupled to the object being moved and associated with each axis of motion to provide position information to a control computer and to the operator.

It is also an object of the present invention to provide motion axes which utilize radial displacement and rotation about a pivot to provide various combinations of surface time and refracted angle, in either a compressional or shear propagation mode.

It is an additional object of the present invention to provide two radial displacement motion axes for a transducer which will allow the transducer to be tilted for inspection of tapered bore areas.

It is another object of the present invention to provide a three axis motion system for positioning one or more transducers.

It is a further object of the present invention to provide a fluid seal between an immersion fluid in which a rotor is immersed and a drive box which provides axial and circumferential motions to a scan head.

It is yet another object of the present invention to provide a water seal which will allow axial and rotational motions of a drive rod.

It is yet an additional object of the present invention to provide a drive box which provides both axial and circumferential motions to a drive head and position readout using resolvers.

It is an object of the present invention to provide a drive box which does not rest in an immersion fluid.

It is another object of the present invention to provide a rectangular drive rod which is hollow and free from projections to allow cables to be inserted and pulled therethrough without damage, and to provide a tight coupling between the drive system, the rod and a resolver system to allow accurate scan head positioning.

It is an object of the present invention to provide a tension coupling between the drive rod and position sensing resolvers to overcome irregularities in the drive rod.

It is an additional object of the present invention to provide a drive box that circumferentially moves a scan head and includes a fail-safe feature that prevents over-rotation.

It is a further object of the present invention to provide a scan head control system that, with high resolution, accurately positions the scan head and feeds back the position, allowing accurate determination of flaw locations during an inspection.

It is an object of the present invention to provide a control system which has independently controllable plural motion axes.

It is yet another object of the present invention to provide a device for locating indications based on their transit times and scanner coordinates.

The present invention attains the above objects by providing an immersion based ultrasonic test system used to interrogate the bore and near bore material of turbine and generator rotors by passing ultrasonic search units through the rotor bore. This system utilizes variable focus array inspection transducers in a shear mode inspection of the bore surface and near bore material. A mapping transducer and a blind bore sensor allows the diameter of the rotor to be mapped as well as the end of a blind rotor to be detected. A scan head centering device or chuck deploys four radial arms to center and support the scan head. Each arm has a roller attached to the end which engages the bore so that the bore will not be damaged as the scan head passes through the bore. The chuck is driven by an electric motor and coupled to a resolver allowing the chuck to be accurately adjusted according to the bore geometry determined by bore mapping. The chuck also includes a pneumatic disengagement device which allows disengagement of the positioning arms for fail-safe retrieval of the scan head in the event of motor or wiring failure. A transducer carriage is provided in the scan head that provides three axes of motion for the inspection transducer. The carriage provides position feedback to allow accurate transducer positioning throughout the rotor. The carriage also carries a ranging transducer that allows correction of inspection beam path geometry for varying bore diameters. A drive rod seal is provided between the immersion fluid and an axial and circumferential drive box that prevents immersion fluid from corroding the mechanism in the drive box. The drive box provides both circumferential and axial motions to the scan head during an inspection. Position resolvers engage the moving drive rod to provide accurate positioning information for the scan head. The drive box provides rapid alternating 360° plus rotations of the scan head coupled with precise steps along the axis of the rotor. The control system for the plural motion axes allows accurate positioning and positioning feedback to a computer which calculates the position of discontinuities. The ultrasonic location procedure allows for flaws to be properly located in near real time during a rotor examination.

These together with other objects and advantages which will be subsequently apparent, reside in the details of construction and operation as more fully hereinafter described and claimed, reference being had to the accompanying drawings forming a part hereof, wherein like numerals refer to like parts throughout.

DESCRIPTION OF THE DRAWINGS

FIGS. 12A–12C illustrate details of the radial motion assembly;

FIGS. 15A–15C depict a drive rod section;

FIG. 16 illustrates a drive rod connector;

FIGS. 33A and 34B together are a servo subroutine executed by the position processor 698;

DESCRIPTION OF THE PREFERRED EMBODIMENTS

The present invention is a rotor ultrasonic inspection system which, based upon immersion ultrasonic test methods, utilizes variable focus shear waves generated by phased array transducers available from New York Institute of Technology. Shear waves are generally better at detecting interfaces that can be cracks in the rotor.

Figure 1:
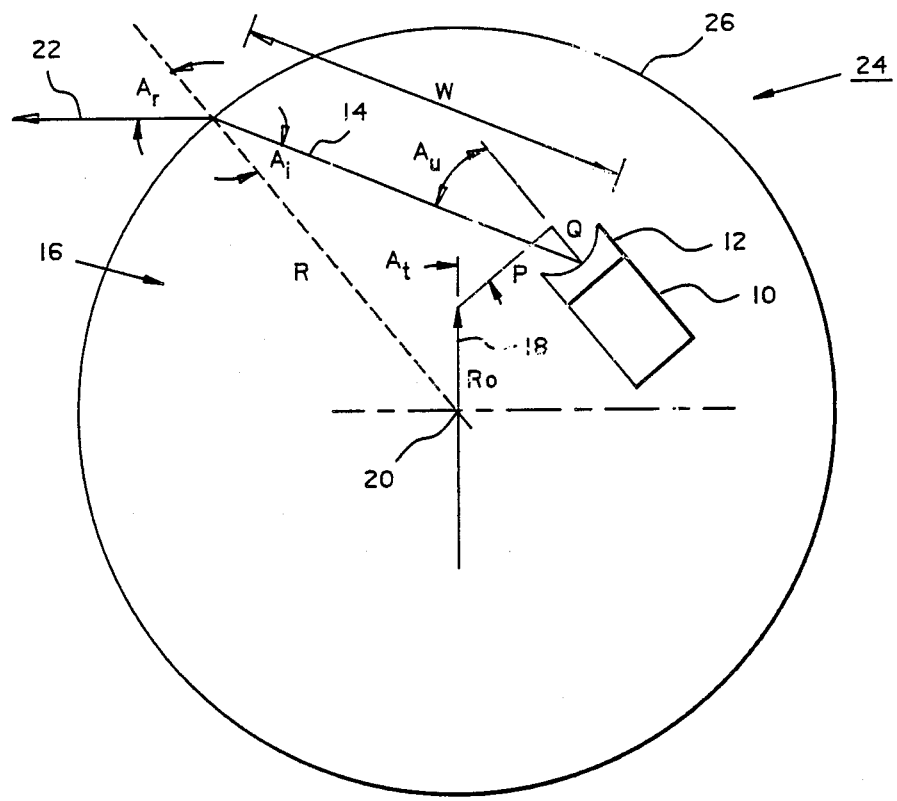
FIG. 1 depicts the relationship between an inspection transducer 10 and a rotor bore 24.

An understanding of the preferred transducer design is necessary to fully understand the present invention. Each transducer 10, as illustrated in FIG. 1, has nine elements that are concentric, planar arc segments, as in a section of an annular array (not shown). Each transducer 10 has a lense 12 attached to the front surface such that the emitted wave 14 passes first through the lense 12 and then into an immersion fluid 16. The lense 12 is designed such that the transducer operates at a specific offset from the bore centerline 20 and when operated at this point a refracted shear beam 22 of a specific angle is generated in the rotor material 24. Beam focus is achieved through a combination of two mechanisms. First, the lense 12 causes a diffraction of the beam as it passes through the complex, concave front surface of the lense 12 into the immersion fluid 16. Second, the pulsing of the array leads to construction and destructive interference of the sound waves generated by the various elements and to the eventual formation of a high intensity focal spot. The lense 12 corrects for the effects of the cylindrical bore curvature and creates a geometrically focussed ultrasonic beam at a given depth in the rotor material 24. A geometrically focussed beam is one which is focussed primarily by the lense; that is, a beam that is formed by pulsing all of the elements at the same time. In this case, the geometric focal depth is approximately 1 to 1¼ inches radially below the bore surface 26 and the designed refracted angle Ar of the shear beam is approximately 40-60 degrees. The geometric focal depth and refracted angle are chosen to allow steering of the beam to the bore surface in one direction and to a depth of 4-6 inches in the other direction. Other focal depths and refracted angles are possible and in certain cases are desirable.

The beam can be steered to, and focussed at, depths other than the geometric focal point by phasing the pulses applied to the various array elements in a known manner. If, for example, it is desirable to steer and focus the beam nearer the bore surface, the outer element of the transducer is pulsed first and the others pulsed sequentially from the outer elements to the inner elements. The amount of the delay provided between each of the elements controls the degree to which the beam is steered, with more delay, steering and focussing the beam nearer the surface. If the beam is to be steered and focussed deeper than the geometric focal depth, the inner element is pulsed first and the sequential pulsing progresses toward the outer elements.

The steering and focussing of the beam by the phasing of the pulses applied to the various elements of the array is called transmit focus. In a real time inspection system, it is neither practical nor necessary to transmit focus on each reflector encountered. Because a given focal point has some depth of focus associated with it, a limited number of focal increments, with overlapping coverage at the transitions from one zone to the next, is sufficient. In the preferred embodiment four to six focal points providing four to six overlapping focal zones or windows is preferred when detailed inspections are necessary. In larger bores, the depth of focus is larger than in smaller bores, requiring less focal zones to get complete coverage in larger bores than in smaller bores.

A second form of focussing involves the method employed to receive the returning echoes. Receive focus is accomplished by receiving the reflected wave on more than one of the elements. For a given focal depth, specific amounts of delay are applied between the various elements receiving the returns so that the returns can be added in phase to achieve optimum signal enhancement. Continuous receive focus, as opposed to incremental receive focus, is achieved by applying appropriate delays to the return signals in hardware as a function of transit time such that the focussing is transparent to the operator. Continuous receive focussing is also referred to as dynamic focussing.

The present invention utilizes multi-element transmit focus with single element receive. This particular means of implementing the phased array technology was selected because of its capability in achieving the desired sensitivity with a minimum of system complexity. However, the present invention can utilize the above-discussed receive focus technique for higher accuracy if desired. Additional details concerning the use of the preferred transducers using the above-described methods can be obtained from the New York Institute of Technology or in the technical literature under the topic of medical ultrasonic imaging.

The present invention is an immersion system in which the bore is completely flooded with an immersion fluid and the transducers are not in contact with the bore. The present invention uses two transducers 10 to accomplish volumetric inspection, with focussed beams, over the first 4-6 inches of material from the bore surface 26 radially outward. The two transducers 10 are identical and each interrogates the full volume of material described. One transducer 10 (FIG. 1) is oriented relative to the bore such that the resulting beam in the material is in a radial/circumferential plane, oriented at an angle $A_r$ of 40-60 degrees from tangent, and aiming in the clockwise direction. The second transducer 10 is identical except that its beam is aimed in the counterclockwise direction. The transducers 10 are located relative to the bore such that the incident angle $A_i$ is about 19-26 degrees and the resulting 40-60 degrees refracted wave 22 in the rotor propagates in the shear mode. The outer four array elements on each side of the transducer are used as transmit elements, and the center element is used as the receiver. This configuration permits the use of a single pre-amplifier near the transducer to boost the return signals before they travel over fairly long cables to the remote electronics.

Figure 2:
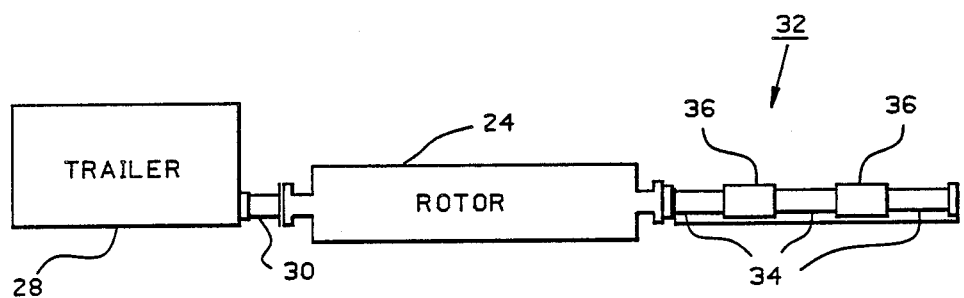
FIG. 2 illustrates the relationship between a rotor 24 being inspected and a trailer 28 housing part of the inspection system.

Part of the inspection system according to the present invention is housed in a trailer 28 coupled to the rotor 24 by a fluid carrying Plexiglas tube 30, as illustrated in FIG. 2. On the opposite end of the rotor 24 from the trailer 28, is a scan head support unit 32 which includes fluid carrying tubes 34 and tube supports 36. The mating between the various fluid bearing tubes 34 and the rotor 24 is accomplished with adapter plates which tightly fit between the rotor and the tube, preventing immersion fluid escape using the necessary seals and O-rings appropriate to the rotor 24 being inspected. Although not shown in FIG. 2, the rotor 24 is tilted at approximately 6 inches per 20 feet (two degrees), with the end away from the trailer 28 being the lower end, so that the rotor bore is completely filled with the immersion fluid.

Figure 3:
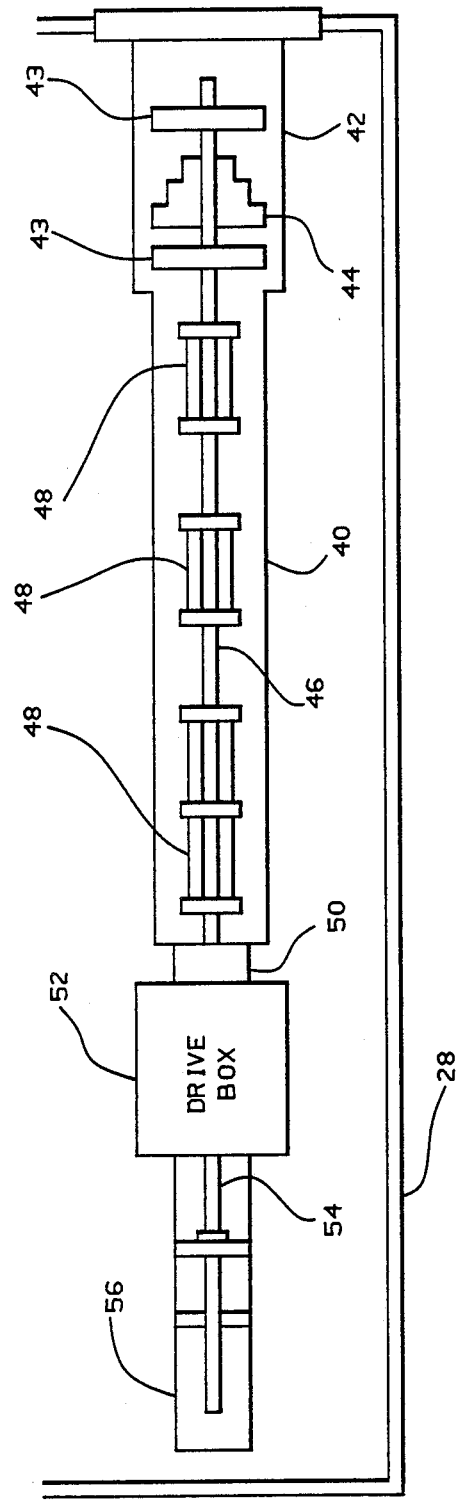
FIG. 3 is a top view of the interior of the trailer 28 of FIG. 2.

Inside the trailer, as illustrated in FIG. 3, is a tilted trough 40 also containing the immersion fluid. The entire trough 40 including calibration tank 42, drive box 52 and drive rod support trolley 56 are mounted on an I-beam 87 (FIG. 4) which is attached to the trailer 28 with jacks 89 and coupled to the trough 40, drive box 52 and calibration tank 42 by supports 88. The jacks 89 provide a means of tilting the trough 40 vertically and moving the trough 40 horizontally to align the trough 40 assembly with the rotor, as described later. The tilting of the rotor ensures that the rotor is completely filled with immersion fluid and allows air in the rotor to escape without requiring additional air removal mechanisms. At one end of the trough 40 is a calibration tank 42 which contains a base for holding one or more calibration blocks 44 used to calibrate a scan head 46 prior to insertion into the rotor 24. These calibration blocks are constructed such that they have a positive positional reference such as a groove, for resting on a support structure 43 in the calibration tank 42 having a corresponding groove. This permits the use of various blocks for different bore diameters while maintaining positive and repeatable position reference for each block with respect to the position of the scan head 46. The scan head 46, while in the trough 40 is supported by slidably movable plexiglas support tubes 48 which are engaged by scan head chucks discussed in detail later. The support tubes 48 are supported by slide rails (not shown) in the bottom of the trough 40. At the end of the trough is a drive rod end seal 50 which prevents the immersion fluid in trough 40 from pouring into drive box 52 or into the trailer 28. The drive box 52 axially and circumferentially moves a segmented hollow rectangular geared drive rod 54 which is supported behind the drive box 52 by drive rod support trolley 56. The I-beam 87 also supports the trolley 56 although this feature is not shown in FIG. 4.

The trough 40, drive box 52 and consequently the drive rod 54 are aligned with the tilted rotor by stretching piano wire from the center of the far end of the rotor 24 using a precision plug to hold the wire. The wire is stretched to and attached to a centering guide mounted at the midpoint of the trough 40. The trough 40 is then moved vertically and horizontally until the wire exits the rotor in the center. The trough 40 is then rotated around the midpoint until the wire is centered in an alignment guide mounted in the calibration tank 42. Proper alignment is necessary to prevent excessive twisting and bending of the drive rod 54 and scan head 46.

Figure 4:
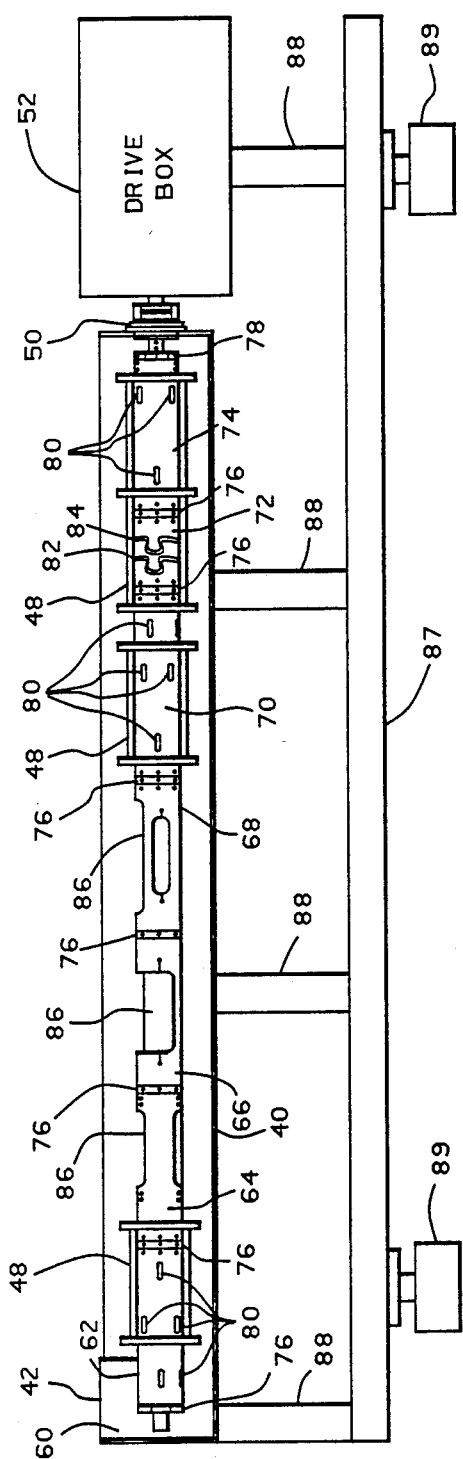
FIG. 4 is a detailed side view of the relationship between a through 40 and a scan head 46 and a drive box 52.

The cylindrical approximately three inch stainless steel scan head 46 is constructed of separate segments 60-74 which are jointed together by connectors 76 and is coupled to the drive rod by a circular-to-rectangular inner diameter fit adapter 78, as illustrated in FIG. 4. The connectors 76 and adapter 78 are constructed with no protruding surfaces so that the scan head 46 will not catch on the interior of a three inch diameter bottle bore. The scan head 46 is actually slightly less than three inches in diameter such that it will fit into bores as small as three inches in diameter.

The scan head 46, which carries the transducers at transducer stations 64-68 through the bore has chucks which center and support the scan head 46 in the bore. Centering of the scan head 46 is achieved via eight motor driven, radially expandable chuck assemblies, discussed in detail later, which extend chuck arms through cutouts 80 in the hollow three inch stainless steel tubes which comprise the chuck stations 62, 70 and 74. The chucks are located in two stations 62 and 70 of three chucks and one station 74 of two chucks. The two stations 62 and 70 are the scan head supports and are located on either side of the transducer stations 64-68. To maintain the position of the transducers 10 relative to the bore, when the transducers 10 do not actually contact the bore, the support system is non-compliant. That is, the supports are rigid because no provisions are needed to make the transducer 10 track the bore surface 26. The grouping of three chucks on either side of the transducers 10 allows for one chuck to be disengaged from the bore as it passes over steps and tapered bottle bore transitions. This is advantageous since the use of at least two chucks at a time on each end of the scan head 46 provides a bending moment on each end which decreases the static sag of the scan head due to its own weight. As the scan head 46 passes axially through the bore, each chuck can be sequentially retracted and then extended as it comes to and then passes by significant bore dimensional changes. The separation between the chucks in a group is approximately nine inches allowing bore transitions of at least eight and one-half inches to be traversed while maintaining alignment of the scan head. As illustrated by FIG. 4, the chuck arm cutouts 80 are offset circumferentially with respect to each other providing twelve different support points when all three chucks on each side of the transducers 10 are engaged and eight support points when bore transitions are traversed. The multiple support points, offset circumferentially, insure rigid support and centering alignment of the scan head 46.

The scan head is driven axially and circumferentially by the remote drive box 52 which remains outside of the bore and which is connected to the scan head via a set of interconnecting drive rods 54. The drive rod 54, discussed in detail later, is a rectangular sectioned hollow aluminum tube that allows all scan head cabling to pass through without obstruction. The scan motion is one of alternating clockwise and counterclockwise 360° plus rotations of the scan head 46 with an axial index each time a rotation reversal occurs. The preferred rotation is 400° with 20° of acceleration rotation being provided before each 360° scan to allow a constant rotational speed to be obtained and 20° being provided for deceleration. The scan rotation time is a function of the bore size so that the surface speed is constant. For a four inch diameter bore a scan rotation is preferably performed in five seconds followed by a spiral axial move to the next scan position. Larger bores are scanned at slower rotational speeds. The axial portion of the spiral move of preferably 0.025 inches is accomplished in 1 second allowing an inspection to be performed at an axial rate of approximately 0.25 inches per minute. The axial index is programmable and can be as small as 0.001 inches or larger than 0.025 inches, if desired.

The chuck station 74 with two chucks is located behind the rear set of scan head chucks 70 between the drive end of the scan head and the drive rod 54. The station 74 is separated from the station 76 by a universal joint station 72. The universal joint station 72 completely decouples the scan head 46 from the drive rod 54 in terms of transmission of lateral loads by using two precision universal joints 82 and 84. The two universal joints 82 and 84 are hollow substantially backlash free stainless steel joints with stainless steel bearing blocks and pins. The hollow joints 82 and 84 allow control cables to pass to the scan head. The joint station 72 not only decouples the scan head 46 from lateral loads but also allows the scan head 46 to be pivoted clear of the trough 40 during maintenance.

The single station 74 of two chucks supports the bore end of the drive rod 54 while scan head 46 is in the bore. Only chuck station 74 is required because the universal joint prevents sag of the drive rod 54 from being transmitted to the scan head 46. Since some sag of the drive rod 54 can be tolerated, the bending moment developed by having at least two chucks of a group engaged at any single time is not required. The use of two chucks within station 74 allows bore diameter transitions of the same size as traversable by the scan head 46 to be transited; however, three chucks would provide better support during transitions. It is also possible to provide drive rod supports (not shown) that can be clamped onto the drive rod 54. The drive rod supports would be required to be of a known diameter as determined by bore mapping, should be spaced approximately six feet apart and should have four nylon feet 90° apart, for contact with the bore surface 28.

The scan head 46 can have up to four transducer stations 60, 64, 66 and 68, where one station 64 is optional. The stations 64–68 are hollow stainless steel tubes with transducer cutouts 86. The required transducer stations 66 and 68 are located between the two chuck stations 62 and 70. The transducer stations 66 and 68 are used for inspection transducers 10 under normal circumstances when the rotor bore extends through the entire length of the rotor 24 and the scan head 46 can pass out of the far end of the rotor 24. It is always advantageous to keep the transducers 10 as close together as possible axially since increased axial spacing equates directly to additional time required to pass the transducers through the bore.

The third required transducer station 60 is located forward of the front chuck station 62 and is used to hold an inspection transducer 10 when blind bore rotors or plugged rotors are inspected. In blind bore inspections, the scan head 46 cannot pass out the far end of the rotor 24 to carry the transducers 10 to the end. The inspection of a blind bore is first conducted in the normal manner over the length possible and then each inspection transducer is moved to the front station 60 and passed along the section missed during the normal portion of the test. The front station 60 during the normal part of the inspection carries bore mapping transducers, for mapping bore diameter as the scan head 46 is inserted into the rotor, as well as a blind bore end sensor for detecting the end of a blind bore. Bore mapping during insertion allows the chucks to be adjusted while moving the scan head 46 into the bore and later while moving the scan head 46 out of the bore during the inspection.

In addition to the two array inspection transducers at stations 60 and 68, the system contains additional single element ranging transducers located in each inspection station and used for surface tracking. These transducers are oriented such that their beams are directed radially outward with the bore surface reflection being the signal of interest. One of these ranging transducers is located in close proximity to each of the two array inspection transducers 10. They are used to track the bore surface as a function of circumferential and axial position and the measurements made with these transducers are used to correct the data collected with the array inspection transducers 10 for diameter changes, misalignment and other geometric variations. It is necessary to use separate transducers because the array transducers 10 do not receive a surface reflection when they are oriented to generate shear waves in the rotor 24. The relationship and operation of the inspection, ranging and bore mapping transducers are discussed in detail in the related applications mentioned in the cross references section.

The two required center transducer stations 66 and 68 each have three motor driven motions, as will be discussed in more detail later, which serve several functions during the course of an examination: (1) they are used to position the transducers properly within the scan head 46 during calibration such that the beam enters the material at the proper attitude; (2) they are used during a scan to reposition the transducer when a new bore size is encountered; and (3) they can be used to tilt the transducers 10 axially so that the beam is oriented properly as the transducer 10 passes through tapered bottle bore transitional regions.

The front transducer station 60, when carrying inspection transducers 10, normally has two motor driven motions which provide the same capabilities as the center stations excluding the axial tilt motion used in tapered regions. The front transducer station 60 can also contain an optional third motion to provide the axial tilt as well as an air evacuation probe. This probe is attached to a remove vacuum system via a vacuum tube which runs through the drive rod 54 and the scan head 46. The air evacuation probe can have one motor driven motion to move it radially outward toward the bore to remove entrapped air pockets, for example, from bottle bores.

Figure 5:
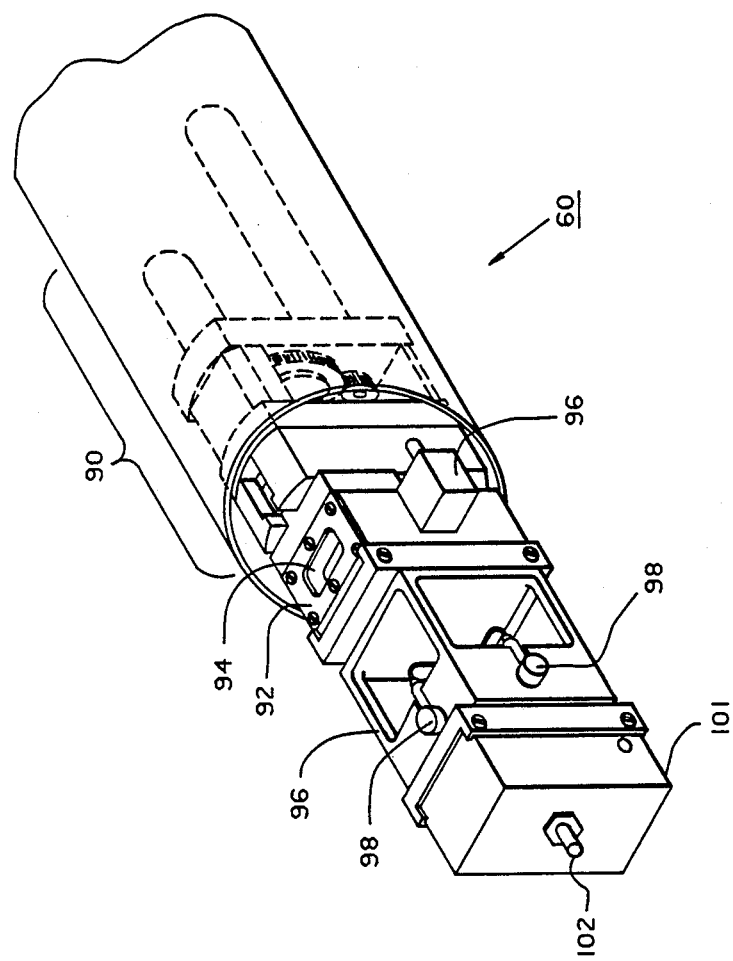
FIG. 5 is a perspective view of a front transducer station 60 when carrying bore mapping transducers 98 and a blind bore end sensor 100.

The front station 60 when carrying the bore mapping transducers and blind bore sensor, is configured as illustrated in FIG. 5. The assembly of FIG. 5 is rotated in alternating spiral motions during a mapping pass while the scan head 46 is being inserted into the bore. A radial motion assembly 90, which will be discussed in more detail later with respect to the inspection transducer carriage, provides radial motion to the mapping transducers 98 so that radial centering adjustments can be made if desired. Attached to the radial motion assembly is the vacuum chamber 92 which includes a vacuum port 94. The vacuum chamber 92 is coupled to a vacuum tube (not shown) by a vacuum tube fitting 96. The radial motion assembly 90 can move the vacuum port 94 into contact with air bubbles and allow them to be removed. Attached to the vacuum chamber 92 is a bore mapping fixture 96 which holds four bore mapping transducers 98, two of which are not shown in this perspective drawing. Suitable one-fourth inch diameter piezoelectric ceramic transducers are available from Panametrics of Massachusetts. The bore mapping transducers 98 are held in position by set screws in fixture 96. The fixture 96 points the transducers 98 normal to the bore surface 26 while the radial assembly 90 centers the fixture 96. The electrical wires from the bore mapping transducers 98, since the entire assembly is in the immersion fluid, should be water tight. On the front of the bore mapping fixture 96 is a blind bore sensor switch 100 with a switch plunger 102. When the blind bore plunger 102 is depressed, the axial motion drive assembly is immediately disabled for continued forward motion of the scan head 46 into the bore. If an inspection transducer 10 is substituted for the bore mapping transducers 98, a tilting mechanism, which will be discussed in more detail later with respect to the inspection transducer carriage, is substituted for the bore mapping fixture 96.

Figure 6:
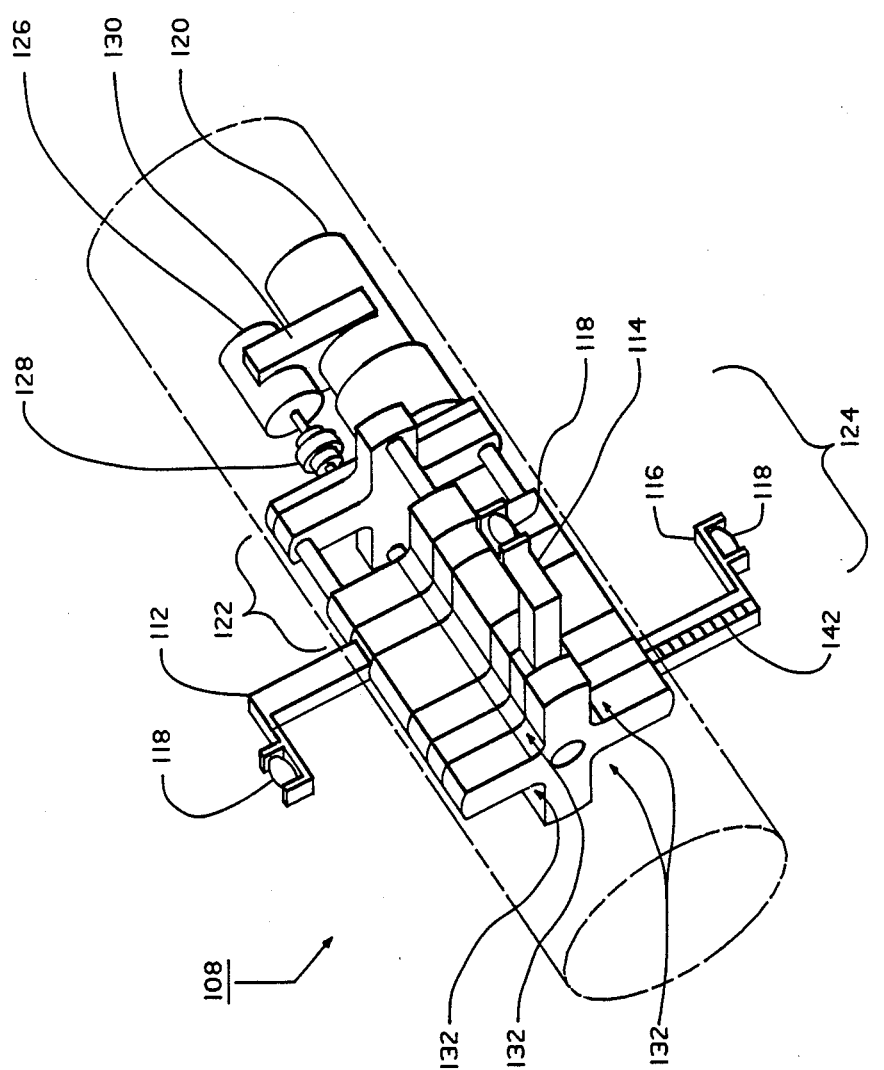
FIG. 6 is a perspective view of a single scan head chuck 108.

One of the chucks as mounted in one of the chuck stations 62, 70 and 74, is illustrated perspectively in FIG. 6. The chuck 108 deploys four stainless steel radial arms 110-116 of which only three 112-116 are shown in FIG. 6. Each arm has a stainless steel slightly crowned roller 118 which engages the bore surface 26 so that the bore surface 26 will not be damaged as the scan head passes through the bore. The chuck arms 110-118 are driven by an electric servomotor 120 through a gear box assembly 122 and an arm drive assembly 124, both of stainless steel. The electric motor 120 is a 20 volt motor obtainable from Pittman of Pennsylvania or TRW and it must be appropriately water proofed. The position of the chuck arms 110-116, is determined by a resolver 126 coupled to the gear drive box 122 by a wafer spring coupling 128 which isolates the resolver 126 from lateral misalignment loads between the resolver 126 and the gear box 122. A suitable resolver is available from Harrow Servo Controls or Transicoil of Pennsylvania and can be a standard aircraft system resolver producing a five volt resolver signal. The resolver 126 is held to the motor 120 by a resolver mounting bracket 130. The four chuck arms 110-116 are set at angles of 90 degrees apart, allowing four cable channels 132 to be created by the radial arm support and spacer plates 134-138 in the arm drive assembly 124.

Figure 7:
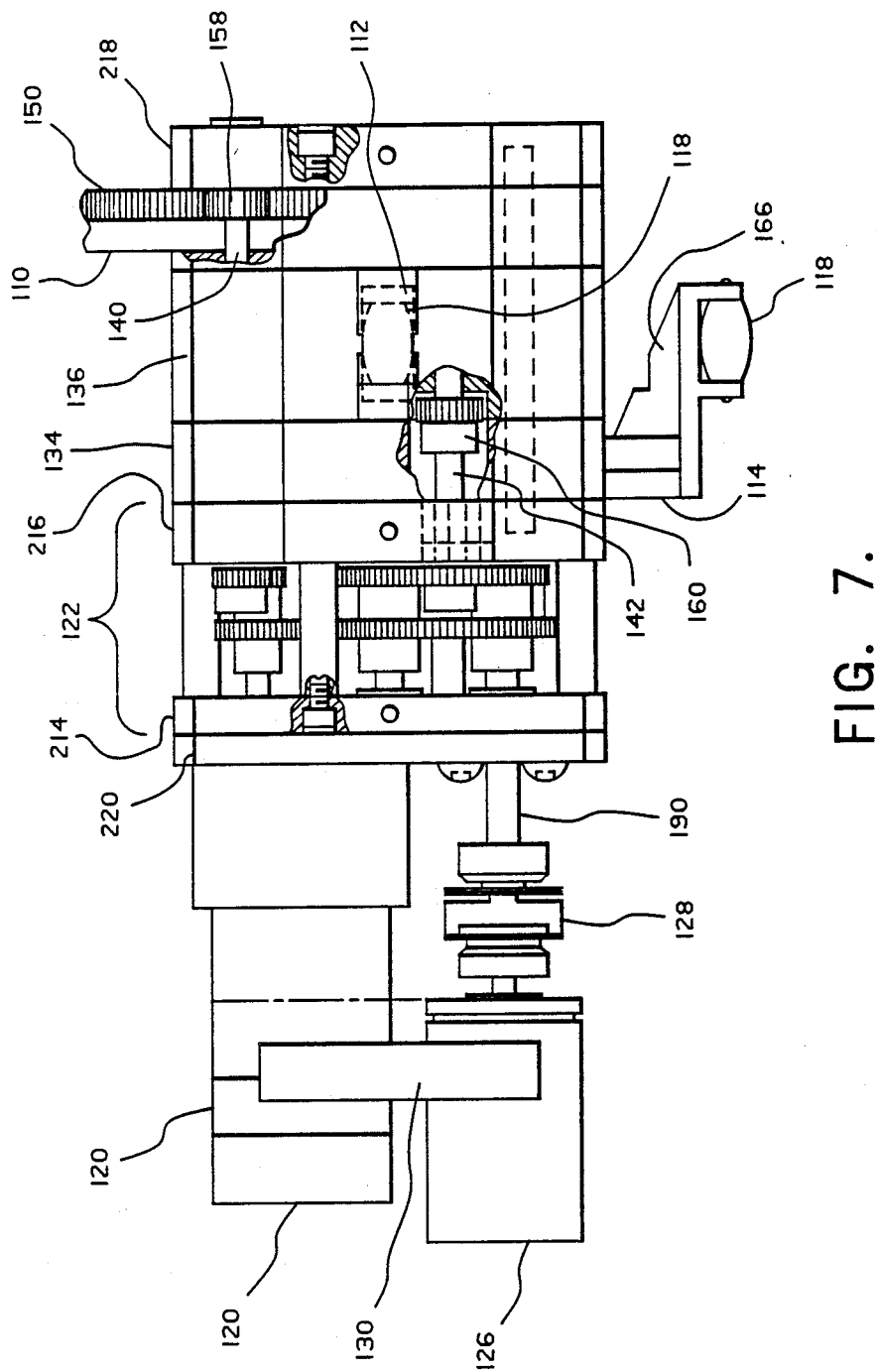
FIG. 7 is a side view of the chuck 108.

As illustrated in FIG. 7, the motor transfers power to the radial support arms 110-116 through gear box 122 which is coupled to rack drive shafts 140-148 in the arm drive assembly 124. The radial support arms include respective racks 150-156 which engage respective rack spur gears 158-164. The radial support arms are offset axially in the chuck station and include cantilevered portions 166 which align the rollers 118 in the same circumferential plane along the bore axis so that the rollers 118 contact the bore surface at the same axial position thereby providing planar scan head support forces that do not apply a twisting moment to the scan head.

Figure 8A:
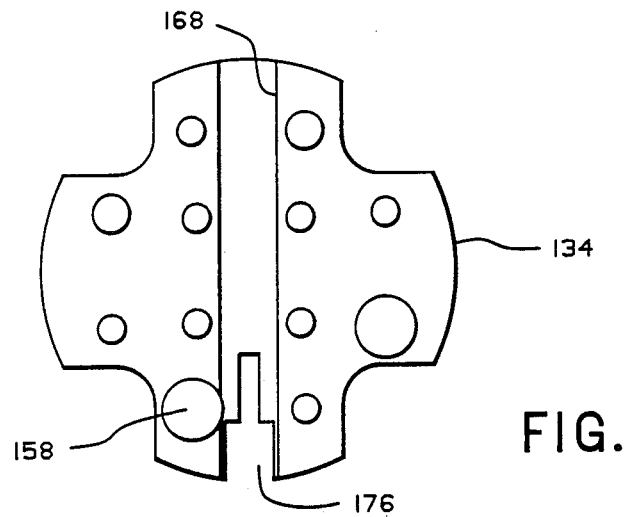
FIGS. 8A and 8B illustrate a support arm support plate 166.
Figure 8B:
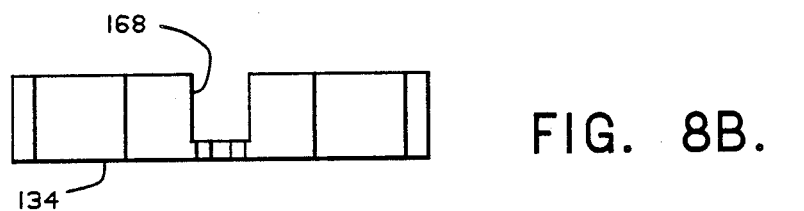

The support arms are separated by stainless steel chuck spacer plates 134-138 which provide lateral support to each radial support via a channel 168 as illustrated in FIGS. 8A and 8B. The channel 168 forms sliding surfaces for the support arms 110-116. The support plate includes a cutout 176 which allows a roller support arm and cantilevered support 166 to be completely retracted into the stainless steel tube chuck station. The pinion gear 158 for driving the rack 150 of the radial support arm 110 is located toward the exterior of the spacer plate so that the radial support arm can be extended to a diameter more than twice the fully retracted chuck diameter by approximately the distance between the spur gears driving diametrical support arms.

Figure 9:
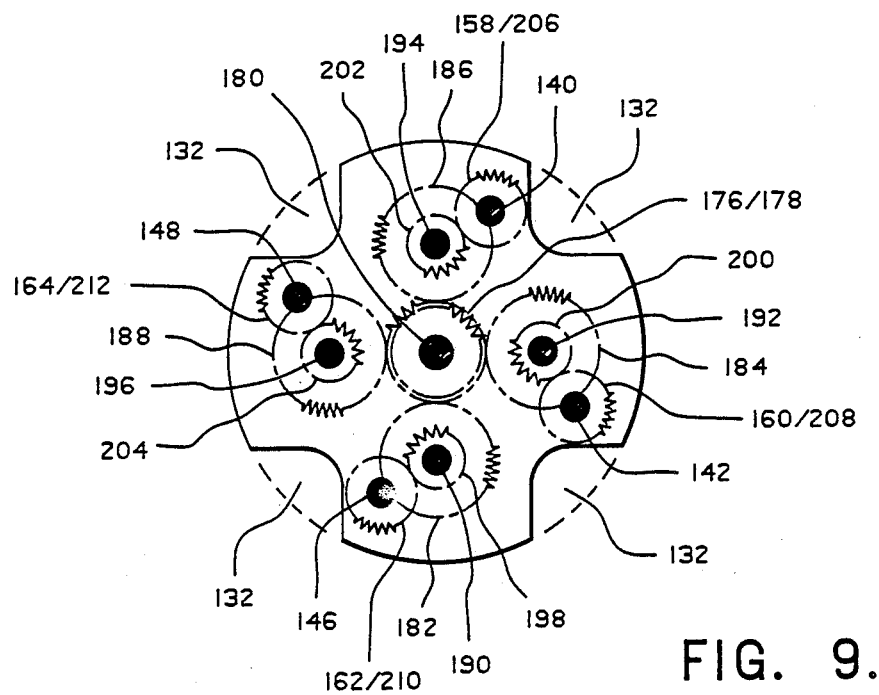
FIG. 9 is an end view of a gear box 130 of the chuck 108 showing the relationship of various shafts and gears for driving the support arms and indicating position.

The motor couples motion to the gear box 122 through a motor shaft 172 and motor gear 174. The motor gear 174 drives a cluster gear 176 rotating a second cluster gear 178 through a cluster gear shaft 180 (See FIG. 9). Cluster gear 178 couples directly to large intermediate gears 182-188. The larger intermediate gears rotate intermediate shafts 190-196 that carry small intermediate gears 198-204. The small intermediate gears 198-204 drive spur gears 206-212 on rack drive shafts 140-148. One intermediate shaft 190 is extended to couple with resolver 126 through spring coupler 128. The various shafts are mounted in friction ball bearings in gear box support plates 214 and 216 and chuck end plate 218. The gear box support plate 214 holds motor support plate 220. The gears, obtainable from W. M. Berg are pinned to the appropriate shafts and produce a substantially backlash free gear train. Appropriate bearings are also obtainable from W. M. Berg. The support plates and gear box are held together by bolting the chuck assembly together on an alignment pin. The chuck assembly is held in position in the chuck station by recessed screws which pass through the chuck station wall while the roller arms 110-116 are aligned with the slots in the chuck station.

To engage the support arms with their associated spur gears 158-164, the last rack tooth on each arm is held in engagement with the associated spur gear while the motor 120 is rotated to cause the support arms 110-116 to be expelled from the chuck. When the motor 120 is reversed, the tooth at the end of the support arm for each spur gear engages the associated spur gear at the same time. If constant pressure is maintained on the roller support arms when the motor direction is reversed, the support arms should be synchronously engaged. After engaging the support arms, the arms can be retracted until the chuck will fit into a calibration tube of known diameter and expanded until the arms contact the interior of the tube. If all the arms do not contact the interior of the calibration tube, the procedure for synchronizing the arms should be conducted again.

Figure 10:
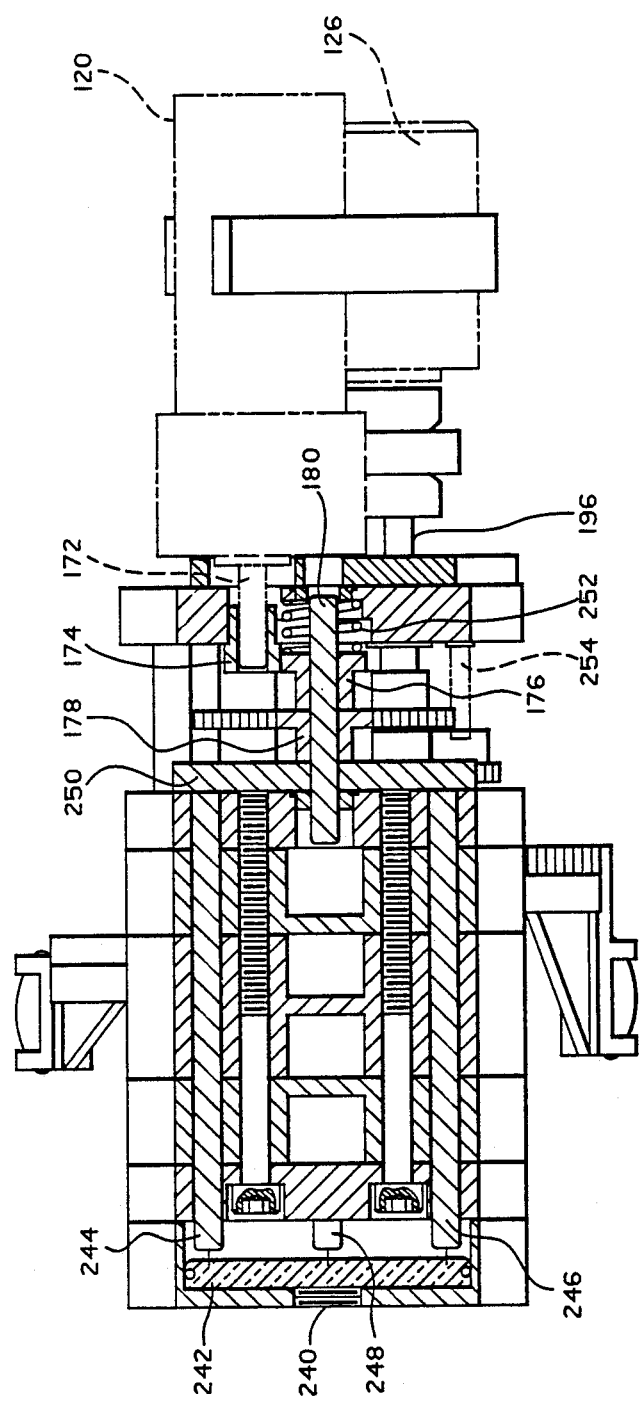
FIG. 10 illustrates a pneumatic chuck disengagement mechanism.

FIG. 10 illustrates a pneumatic disengagement device which disengages the cluster gears 176 and 178 from the intermediate gears and allows the roller arms to be retracted whenever the motor 120 becomes inoperable. When air is forced into air inlet 240, it forces O-ring sealed pressure plate 242 against push rods 244-249. The four push rods 244-249 transmit force to cluster gear shaft lifting plate 250 which is coupled to cluster shaft 180 on which cluster gears 176 and 178 ride. The movement of shaft 180 disengages the cluster gears from the intermediate gears 182-188, allowing the rack shafts 140-148 to freely rotate. When the scan head 46 is withdrawn from the bore, the roller arms 110-116 will automatically retract when smaller bore diameter portions are encountered. A spring 252 will force the cluster gears 176 and 178 back into engagement with the intermediate gears 182-188 whenever the pressurized air, applied through air inlet 240, is released. The spring 252 is useful for testing the disengagement mechanism prior to insertion of the scan head 46 into the rotor 24. A proximity sensor 254 is positioned to sense when the lifting plate 250 has disengaged the cluster gears 176 and 178 from the intermediate gears 182-188, thereby providing confirmation that the support arms are disengaged and the scan head can be removed.

Since the chuck will likely encounter rotor bores of varying diameter, a supporting frame or guide can be clamped to the exterior of the chuck station to provide extra lateral and circumferential support for very long support arms. These may be sized such that they just fit into the minimum clearance opening for any particular bore, thereby providing maximum possible support when the arms are extended into an internal bottle bore.

Figure 11:
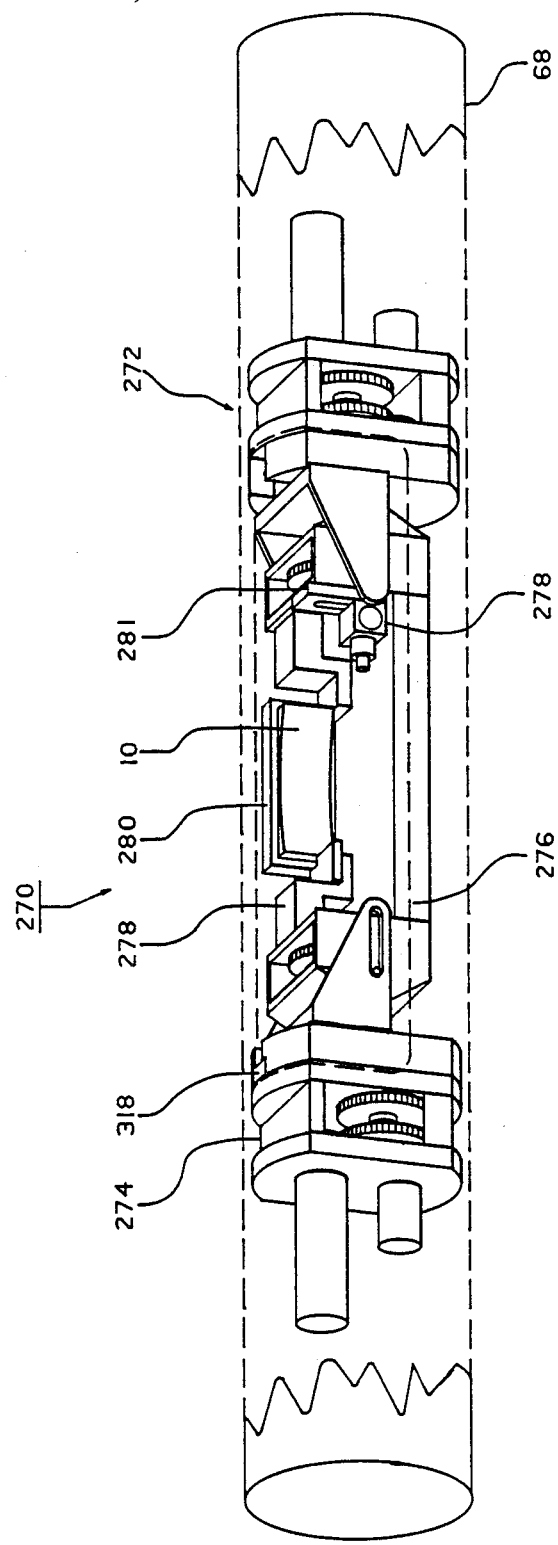
FIG. 11 is a perspective view of a carriage 270 for an inspection transducer and a ranging transducer 278 as positioned in the scan head 46.

Each of the inspection transducers 10 is mounted in a carriage which has three independent motion axes to properly position the transducer 10 such that the ultrasonic beam enters the material at the proper incident angle. Radial support assemblies 272 and 274, as illustrated in FIG. 11, provide radial adjustment of the transducer and when one radial support assembly is held at a constant level, while the other radial support assembly is moved, the transducer can be tilted. The carriage 276 attached to the radial support assemblies 272 and 274 can be used to rotate the transducer support bar 278 providing the third axis of motion. The transducer carriage also holds a ranging transducer 278 on an adjustable bracket 280.

In immersion ultrasonic testing the key parameters which must be controlled in order to maintain beam integrity are water path length, or transducer standoff distance, and incident angle, or the angle at which the beam strikes the bore surface 26. Water path length is important since reflector positions must be is determined by a calculation based on the wave transit time in combination with a knowledge of the beam path and associated travel velocities. When focussed beams are used, water path length is even more significant because it affects the point within the material at which the beam will be in focus. The incident angle is important since it affects the beam propagation mode in the material (i.e., compressional mode or shear mode), its refracted angle in the material, and the intensity of the beam. All of these play key roles in maintaining inspection sensitivity, resolution, and accuracy of positional placement of reflectors. In the preferred embodiment, the transducers 10 are placed relative to the bore surface 26 such that the resultant wave in the rotor material propagates in shear mode, in a radial-circumferential plane, and at a refracted angle of about 45 degrees relative to tangent. The transducer offset and the resulting water path lengths are a matter of transducer design and can be set to any desired value.

FIG. 1 shows the key transducer position parameters for immersion based, shear mode interrogation of rotor material with the ultrasonic beam entering from the bore. The angle $A_u$ at which the ultrasonic beam exits from the transducer 10 is fixed for a particular transducer 10 by the transducer 10 and lense 12 designs. The desired refracted angle $A_r$ in the rotor material and the desired water path length W which the transducer must be offset from the bore surface 26 are determined by the transducer design. The key to achieving sensitive, accurate, repeatable inspections is to correctly position the transducer 10 relative to the bore surface so that the water path length W and the refracted angle $A_r$ are accurately set to the design values and can be repeated accurately. FIG. 1 also shows the two motion axes used in the present invention to properly position the transducer 10. The offset $R_o$ is the radial support motion and the angle $A_t$ is the transducer tilt motion. The transducer 10 offsets P and Q are setup values which are functions of the position in which the transducer 10 is mounted within the support carriage 276. During the process of mounting the transducer 10, the values for P and Q are fixed and can be measured with a mechanical measuring device, and the transducer 10 is also adjusted so that the beam is in a radial-circumferential plane, that is, the transducer 10 is adjusted so that it is not tilted axially. The values set for radial offset $R_o$ of the rotation axis and transducer tilt $A_t$ about the rotation pivot point are servo-motor driven and the positions are read by resolvers and fed back to a central computer for motion control and operator display. The water path W and refracted $A_r$ angle can be calculated according to the following equations:

$$C = (R_o \sin A_t - Q) \tan A_u + P + R_o \cos A_t$$

$$A_i = \sin^{-1} [(C/R) \cos A_u]$$

$$W = C \sin (90° + A_u - A_i)/\sin A_i - (R_o \sin A_t - Q)/\cos A_u$$

$$A_r = \sin^{-1} [(V_s/V_w) \sin A_i]$$

where, as illustrated in FIG. 1, $A_r$ equals the refracted angle in shear mode, $A_i$ equals the incident angle, $A_u$ is the ultrasonic beam angle out of transducer 10, $A_t$ is the transducer 10 rotation angle, Q equals the fixed offset of the transducer 10 from the center of the transducer tilt rotation in a direction parallel or nearly parallel to the beam, P is the fixed offset of transducer 10 from center of the transducer tilt rotation in a direction perpendicular or nearly perpendicular to the beam, R is the bore radius, $R_o$ equals the radial offset of the transducer rotation axis, W is the water path length (the immersion fluid path length), $V_w$ is the velocity of sound in water, and $V_s$ is the shear velocity in steel. The transducer 10 is clamped in a mounting bracket 280 which is part of the transducer carriage 276. The bracket and support arm 278 can be rotated within the carriage 276 which results in transducer rotation $A_t$. The entire carriage 276 is displaced radially to accomplish the second motion $R_o$ required for transducer positioning.

The radial motion at each end of the transducer carriage 276 is accomplished by the radial motion assembly, shown in FIGS. 12A-12C. The assembly is designed to mount inside the cylindrical stainless steel scan head 46. All components fit within a limited portion of the cross section of the scan head 46 so that additional space is reserved for wiring which must pass by the radial suport (see end view FIG. 12B). A drive gear 290 is mounted on a shaft 292 of a drive motor 294 (FIG. 12A). The drive gear 292 engages with spur gear 296 which is mounted in an intermediate shaft 298. Gear 300, which is also mounted on the intermediate shaft 298, engages spur gear 302 mounted on the output shaft 304 (FIG. 12C). This output shaft 304 directly drives a position resolver 306 at a 1 to 1 ratio and has a second gear 308 which runs a rack 310 in a radial direction. The rack 310 is T-shaped and is part of a carrying bracket that supports the carriage 276. Each shaft is provided with the appropriate bearings to ensure smooth operation.

The T-shaped gear rack 310 slides in rack guides 312 and 314 (FIG. 12B) which support it and maintain it in intimate contact with gear 308 which drives the rack 310. The guides 312 and 314 form a T-shaped channel 316 (FIG. 11) which securely supports the rack 310 throughout its length. The gear rack 310 is attached to the end of the transducer carriage bracket so that operation of the radial support motor results in a radial displacement of the end of the carriage 276. Two of the radial support assemblies are used, one attached to each end of the carriage, to support the carriage 276 and provide for axial tilt. The gear racks 310 are interchangeable and are made in different lengths to cover different bore sizes. Appropriate spacers are provided to maintain separation between mounting plates 318 and 320 for holding the motor 294, resolver 306 and guides 312 and 314.

The radial offset of the transducer 10 rotation axis is controlled by the two radial motion assemblies 272 and 274, one located on each axial end of the transducer carriage 276, so that the two radial motions can be used to tilt the transducer carriage 276 in the radial-axial plane as the transducer 10 passes through tapered areas of a bore. If this tilting capability is to be used for tapered areas in this manner, the transducer can be manually tilted in the mounting bracket 280 (rotation about its radial axis) to maintain the beam in a plane which is perpendicular to the bore surface. This adjustment, if required, is done during system calibration. Alternately, transducer 10 rotation about its radial axis could be incorporated as a fourth motion. As still another option, and the preferred one, the carriage is tilted through the use of the two radial supports, and any reflector positional error which results from not providing the accompanying rotation about the radial axis of the transducer would be removed using known geometry calculations with parameters that are determined during calibration.

Figure 13A:
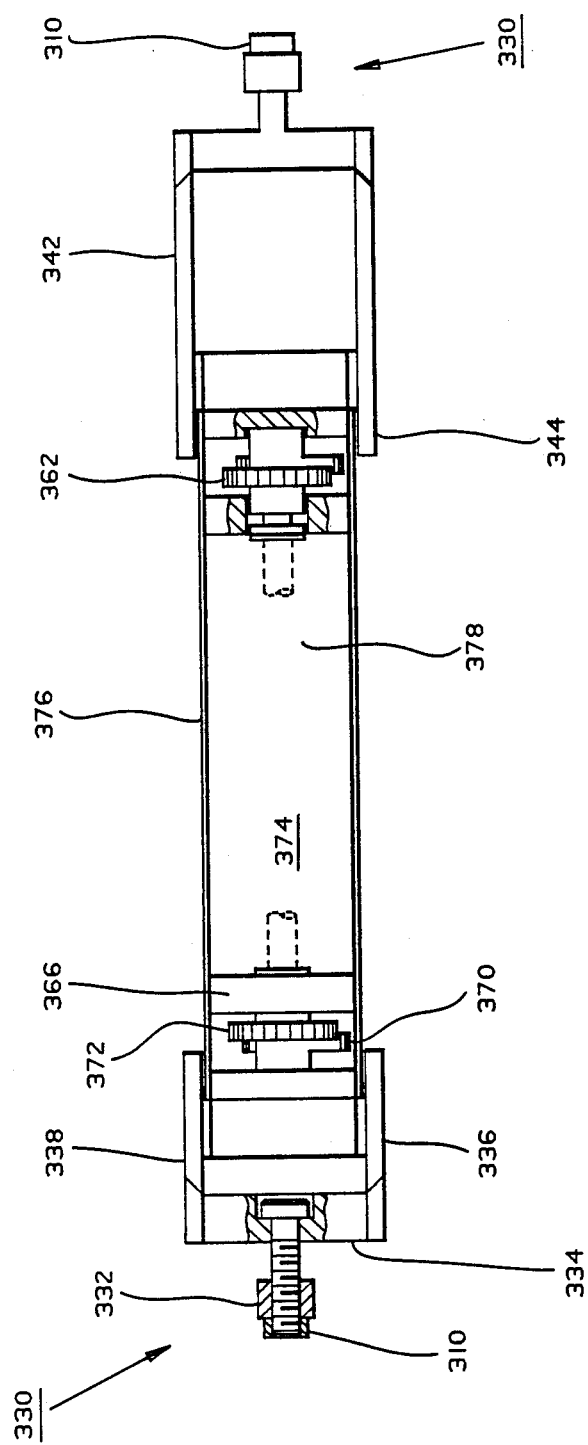
FIGS. 13A–13E depict the components of the carriage assembly.
Figure 13B:
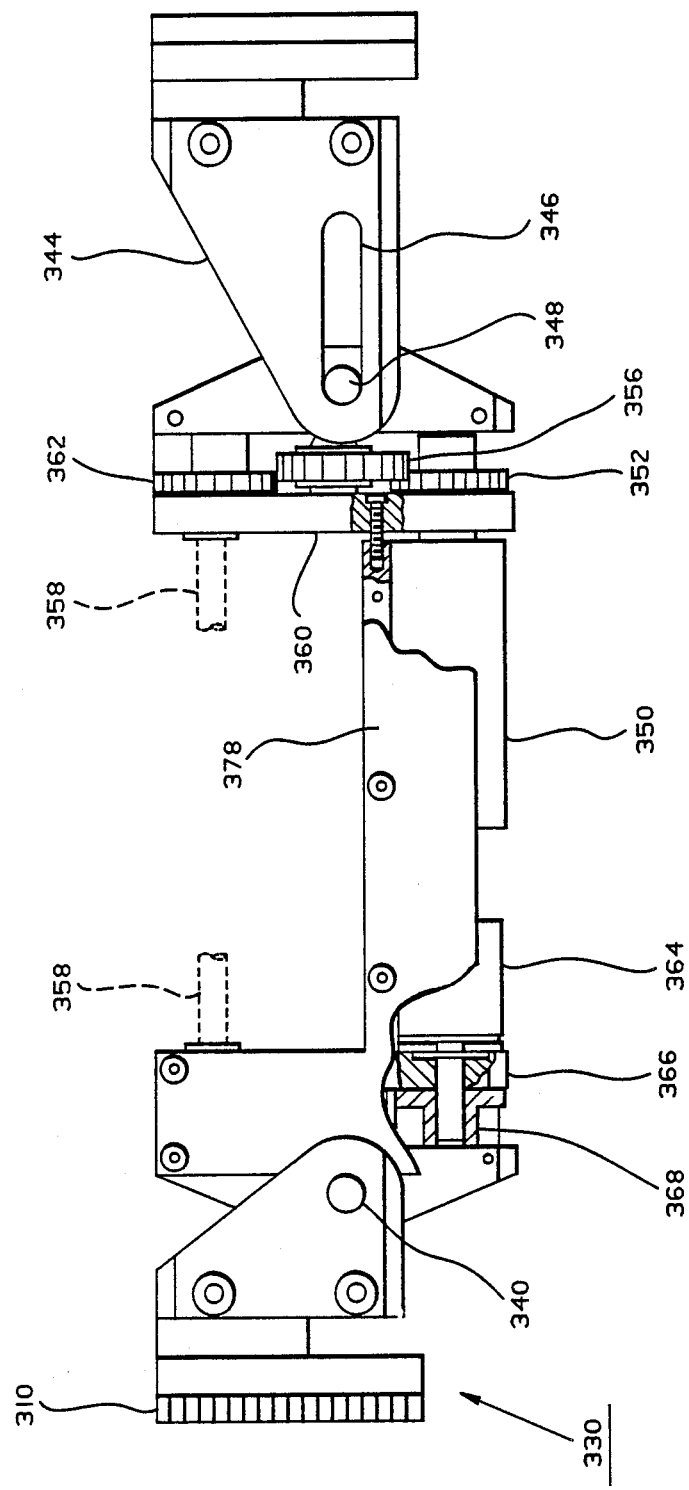
Figure 13C:
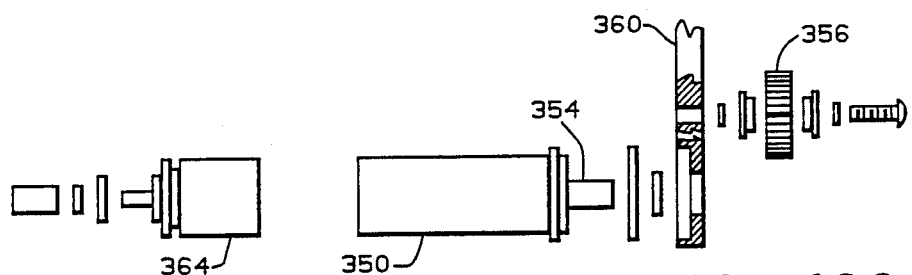

The transducer carriage 276 is shown in detail in FIGS. 13A–13C. Each gear rack assembly 330 is made up of the gear rack 310, a spacer 332 which positions it properly relative to the gear 308 which drives it, a mounting plate 334 to which the gear rack 310 and spacer 332 are attached, and two side plates 336 and 338 which attach to the mounting plate 334 and to the carriage and form the carriage mounting bracket. The side support plates 336 and 338 are rigidly attached to the gear rack mounting plate 334 and to the carriage 276 via a pivot shaft 340. The side or pivot plates 336 and 338 on one end of the carriage 276 provide only rotation, and the pivot plates 342 and 344 on the other end of the carriage 276 provide for axial motion of the carriage relative to the pivot plates as well as rotation. This is accomplished through the use of a sliding pivot slot 346 in each plate and allows for the effective change in the axial dimension of the carriage 276 by sliding on pivot shaft 348, which goes by the cosine of the tilt angle, as it is tilted.

The carriage assembly which holds and rotates the transducer mounting fixture, is shown in a cutaway view of FIG. 13B. A motor 350 lies in the bottom portion of the aluminum carrage 276, with its axis parallel to the transducer rotation axis, and with its drive end facing outboard rather than toward the center of the carriage 276. The motor 350 has an integral gear box and is available from TRW Corporation through distribution of their TRW Globe motor products. A drive gear 352 is mounted on the motor shaft 254 and drives an intermediate gear 356 which is used merely to increase the spacing between the motor 350 and the transducer rotation shaft 358 without using large gears. The motor 350, intermediate gear 356 and shaft 358 are mounted in a motor plate 360 forming one end of the carriage 266. The intermediate gear 356 engages gear 362 to rotate the transducer rotation shaft 358. The transducer rotation shaft 358 is directed back over the motor so that transducer lies above the motor. A resolver 364 is mounted in resolver mounting plate 366 in line with the motor 350 with its driven end facing away from the motor 350. The plate 366 forms one end of the carriage 276. The resolver 364 is connected through three gears 368–372, similar to the gear arrangement between the motor 350 and transducer rotation shaft 358, to the second part of transducer rotation shaft 358. The carriage also includes a center plate 374 and two side plates 376 and 378 which form a U-shaped rigid structure for carrying the transducer 10.

Figure 13D:
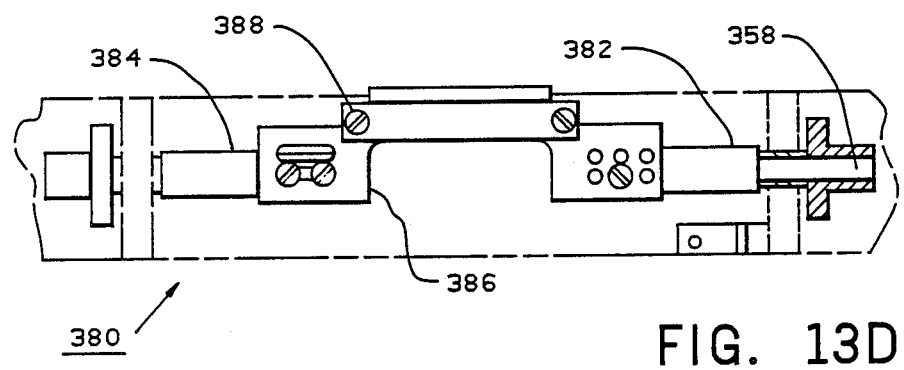
Figure 13E:
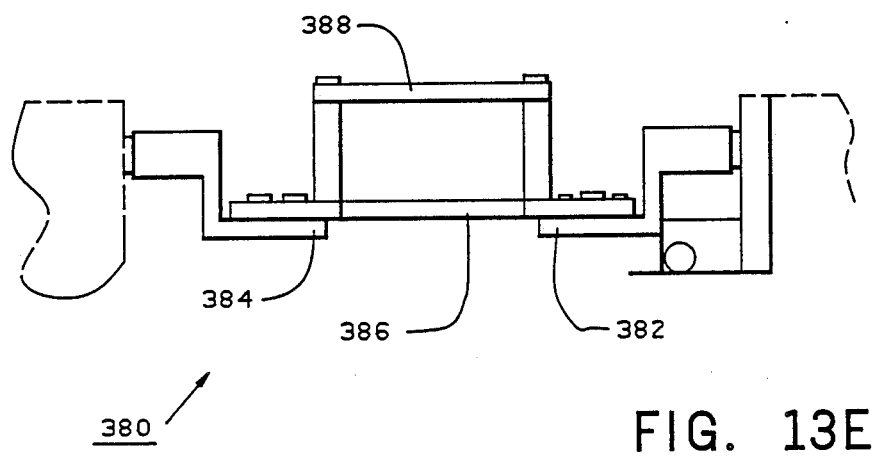

A transducer mounting bracket assembly 300 (FIGS. 13D and 13E) attaches to the shaft 358. The mounting bracket assembly includes shaft riders 382 and 384 which support an adjustable transducer holder 386 having a cutout that prevents ultrasonic reflections from the holder itself. Other artifact reflections discovered during calibration can be damped with appropriate damping material. The transducer 10 is held in holder 386 by a top plate 388. Motor rotation is converted to a rotation of the transducer mounting bracket, which is transferred to the resolver gearing, and finally to the resolver 364 for position readout and monitoring. The space between the motor 350 and resolver 364 and the transducer rotation shaft 358 is sufficient to allow the transducer 10 to rotate without interfering with the rest of the carriage 276. All shafts are provided with appropriate bearings to allow smooth operation.

The normal configuration for the front station 60 during blind bore inspections is to attach a modified carriage to the front radial support motion. This modified carriage (not shown) is similar to the normal carriage shown in FIGS. 13A–13E except the end plates are removed from both ends of the carriage and one end is rigidly attached to rack assembly 330. One optional modification to this inspection type front station is to insert a manual tilt motion between the rack assembly and the modified carriage to provide for tilting of the carriage during inspection of tapered regions. This tilt motion could also be motor driven with a resolver readout.

Suitable motors, resolvers, gears and bearings for the transducer station can be obtained from the suppliers previously mentioned.

Figure 14A:
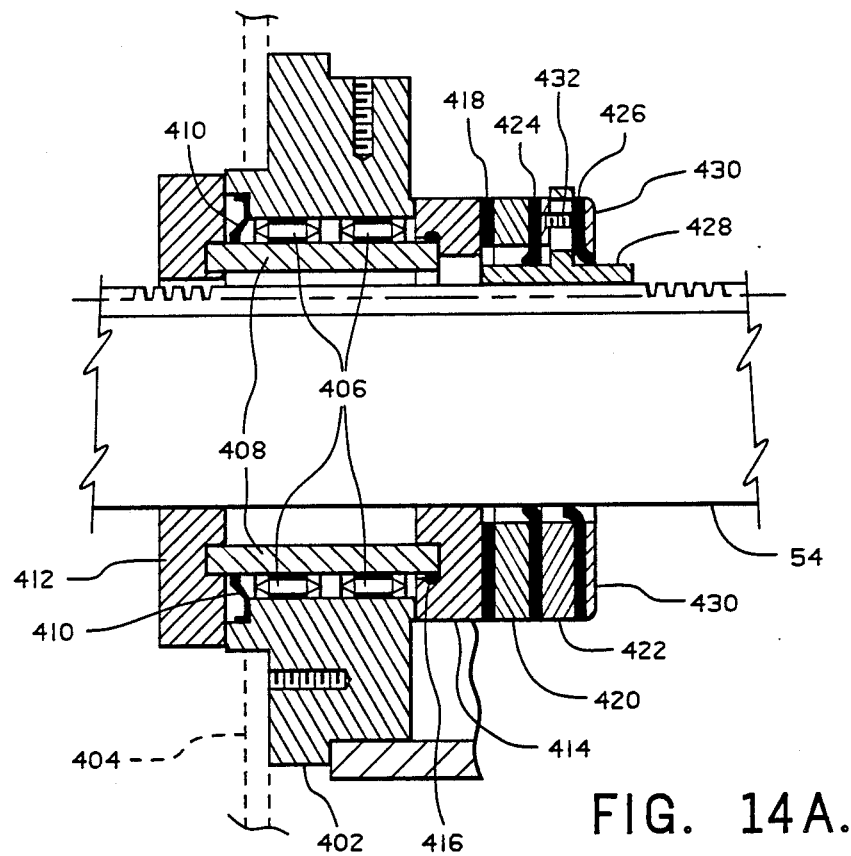
FIGS. 14A and 14B show the drive rod seal 40 that fits on the trough 40 and holds the drive rod 54.
Figure 14B:
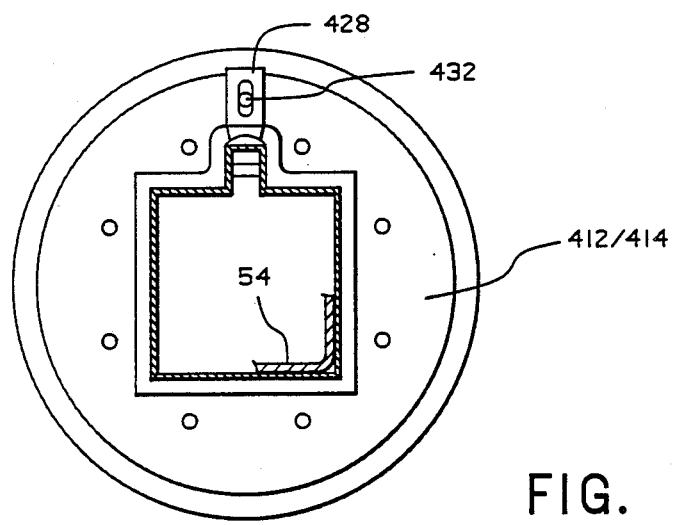

A drive rod seal 400, as illustrated in FIGS. 14A–14B, permits a transition from a wet water filled trough 40 to a dry drive box 52. With the drive box 52, a drive rod 54 is driven axially and circumferentially to accomplish the motion of the scan head 46 which carries the ultrasonic transducers 10. Since the drive box 52 is located outside of the trough 40, a method of sealing is needed to prevent excessive water from leaving the trough 49 where the drive rod 54 exits and then enters the drive box 52 or from spilling into the trailer 28.

The seal assembly 400 includes a aluminum drive rod housing 402 that is bolted to a trough end plate 404. Inserted in the center are two rows of needle bearings 406. A stainless steel sleeve of an appropriate diameter is inserted between the bearings 406 to serve as an inner race 408. On the side of the assembly 400 placed inside the trough 40, a circular bearing seal 410, such as a transmission oil shaft seal, is placed over the inner race 408 and inserted into the drive rod housing 402 to prevent moisture from entering the bearings. On this same side a nylon slide block 412 is attached to the end of the inner race 408. On the opposite side of the assembly 400, another nylon slide block 414 with an integral O-ring 416 is attached to the other end of the inner race 408. Along with the slide block 414, a neoprene gasket 418, two aluminum spacer plates 420 and 422, two neoprene wipers 424 and 426, a rack slide 428 and a cover plate 430 are also attached to this side of the inner race 408.

The slide blocks 412 and 414 serve to attach the bearing assembly to the housing 402 so the circumferential motion can be achieved, and also provide drive rod 53 support surfaces for axial motion. The neoprene gasket 418 and wipes 424 and 426 act as moisture seals between adjacent parts. The two neoprene wipers 424 and 426 help strip moisture from the drive rod 54 as it moves axially. They also provide a seal and contact pressure for the rack slide 428. The rack slide, which rides over the drive rod gear rack to limit moisture escape, is guided by a threaded stud 432 and by the pressure applied by the neoprene wipers 424 and 426.

The assembly 400 outside the trough 40 is then enclosed in a Plexiglas tube. The tube is closed at one end, except for an opening to allow drive rod clearance, and is fastened and sealed with an O-ring to the drive rod housing at the opposite end. The tube provides a catch basin for any additional water that may pass through the seal. The complete assembly is then attached to the trough 40 and sealed to the outside surface by means of an O-Ring.

Each drive rod section, as depicted in FIGS. 15A-15C, includes a square cross-sectional aluminum tube 440 two inches on a side with a linear gear rack 442 attached to the complete six foot length of the drive rod section. The interior of the drive rod 54 is smooth and completely free from any projections so that all necessary cables for the scan head can be easily inserted into the drive rod 54 and pulled through without damaging the cables. The drive rod 54 is constructed using screw holes that do not penetrate the tube 440 so that there are no penetrations of the rod. This prevents water, used during the boresonic examination, from dripping into the drive box. Because the entire trough and drive box are tilted at an angle of about 2°, the water level is such that it is below the open end of the drive rod 54 which protrudes out of the back of the drive box 52. The linear rack 442 is attached to the tube 440 by welded pegs 444 which match machined slots 446 in the rack 442. Pins are inserted through the rack 442 and the pegs to securely fasten the rack 442 to the tube 440. The rack 442 rests in a machined slot 448 riding along the entire length of each tube 440.

The drive rod sections are joined together using a nickel plated brass connector 450, as illustrated in FIG. 16, that fits into the ends of adjacent drive rod sections while all scan head cables are in place and is fixed in place with screws that do not penetrate through the connector 450. Each U-shaped connector has a cover plate 452 which fits in a center slot 454 in the connector 450. When the connector 460 has been assembled into one drive rod section after the cover plate 452 is attached, a gasket material such as silicon sealant is applied around the connector 450 and cover plate 452 at the end of the first drive rod section. When a second drive rod section is pushed onto the connector 450 and cover plate 452, the gasket material forms a seal against fluid leaks. With this drive rod assembly, it is not necessary to seal inside the rods, the rods are filled with fluid and no leakage occurs as long as the extreme end of the rod assembly is above the water level which is accomplished by tilting the entire test set up as described earlier. The connector 450 is designed to allow the drive rod sections to abut each other so that the adjacent racks 442 form a continuous gear rack. The racks 442 are therefore designed to end in the middle of a gear trough so that the adjacent racks form a single gear trough.

Figure 17:
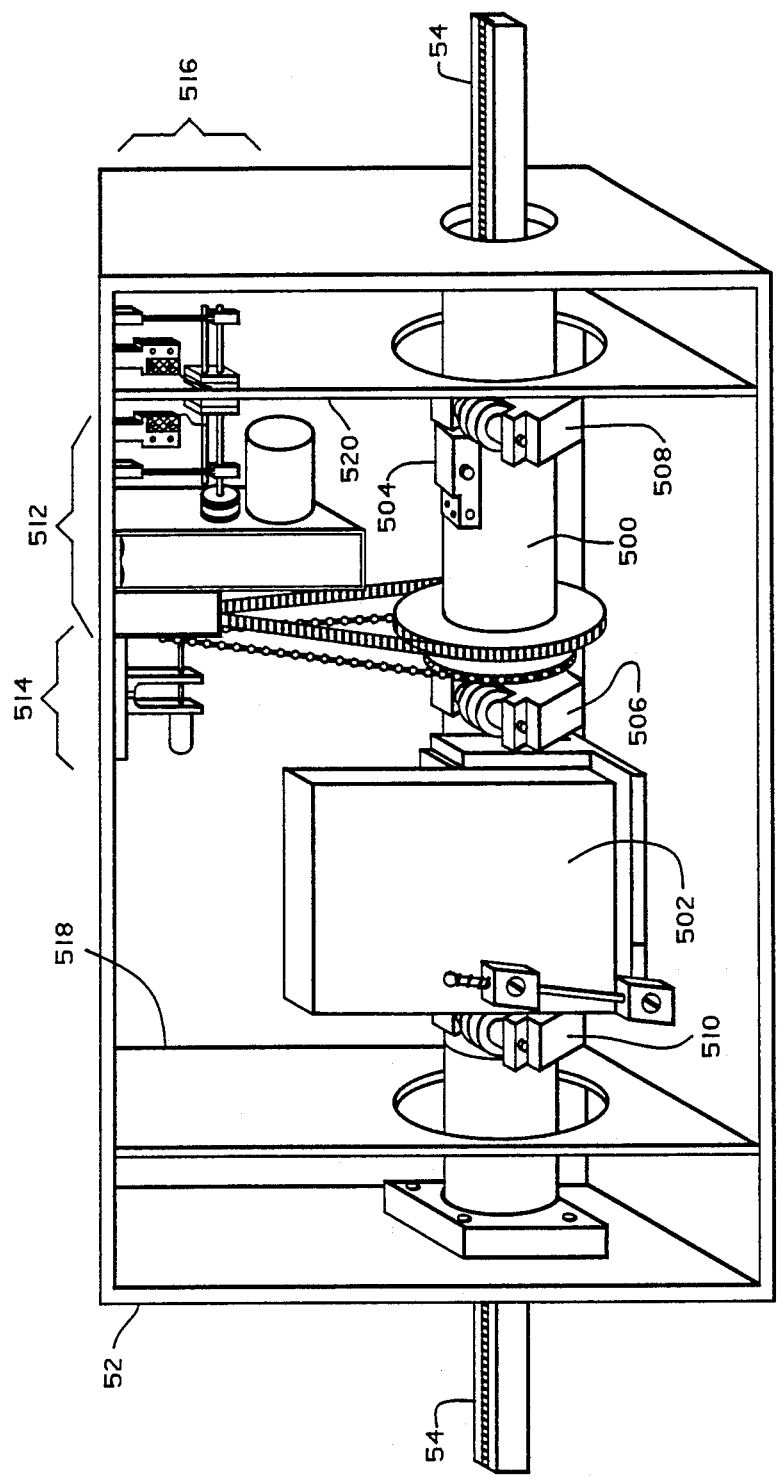
FIG. 17 is a perspective view of the drive box 52.

The basic purpose of the drive box 52 illustrated in FIG. 17 is to transmit axial and circumferential motion through the drive rod 54 to the scan head 46 which holds the ultrasonic transducers 10 that perform the inspection. The drive box 52 includes a carriage tube 500 that runs the length of the drive box 52, an axial drive assembly 502 mounted on the carriage tube 500 which moves the drive rod through box 52. An axial resolver assembly 504, also mounted on the carriage tube 500, indicates the position of the drive rod 54. The drive rod 54 is carried by roller support assemblies 506-510 which are secured to the carriage tube 500 and support the drove rod 54. A circumferential drive assembly 512 rotates the carriage tube 500 and roller assemblies 506-510 in order to rotate drive rod 54. A circumferential resolver assembly 514 is also provided to indicate the circumferential position of the drive rod 54. A limit switch assembly 516 is provided to prevent over rotation of the carriage tube 500 so that drive cables do not get damaged. The drive box 52 also includes cable shields 518 and 520 behind which control cables can be contained and spooled so that the cables do not become entangled with the rotating carriage tube 500 and attached assemblies.

The carriage tube 500 is a hollow thick walled aluminum tube that runs the length of the drive box enclosure and is supported by heavy duty roller bearings 530 and 532 which receive thick walled aluminum sleeves (not shown) that slide out of the carriage tube 500 and tightly fit into the associated bearins 530 and 532. The sleeves are held in place by set screws. The carriage tube 500 has cutouts through which the various assemblies mate with the drive rod 54.

Figure 18:
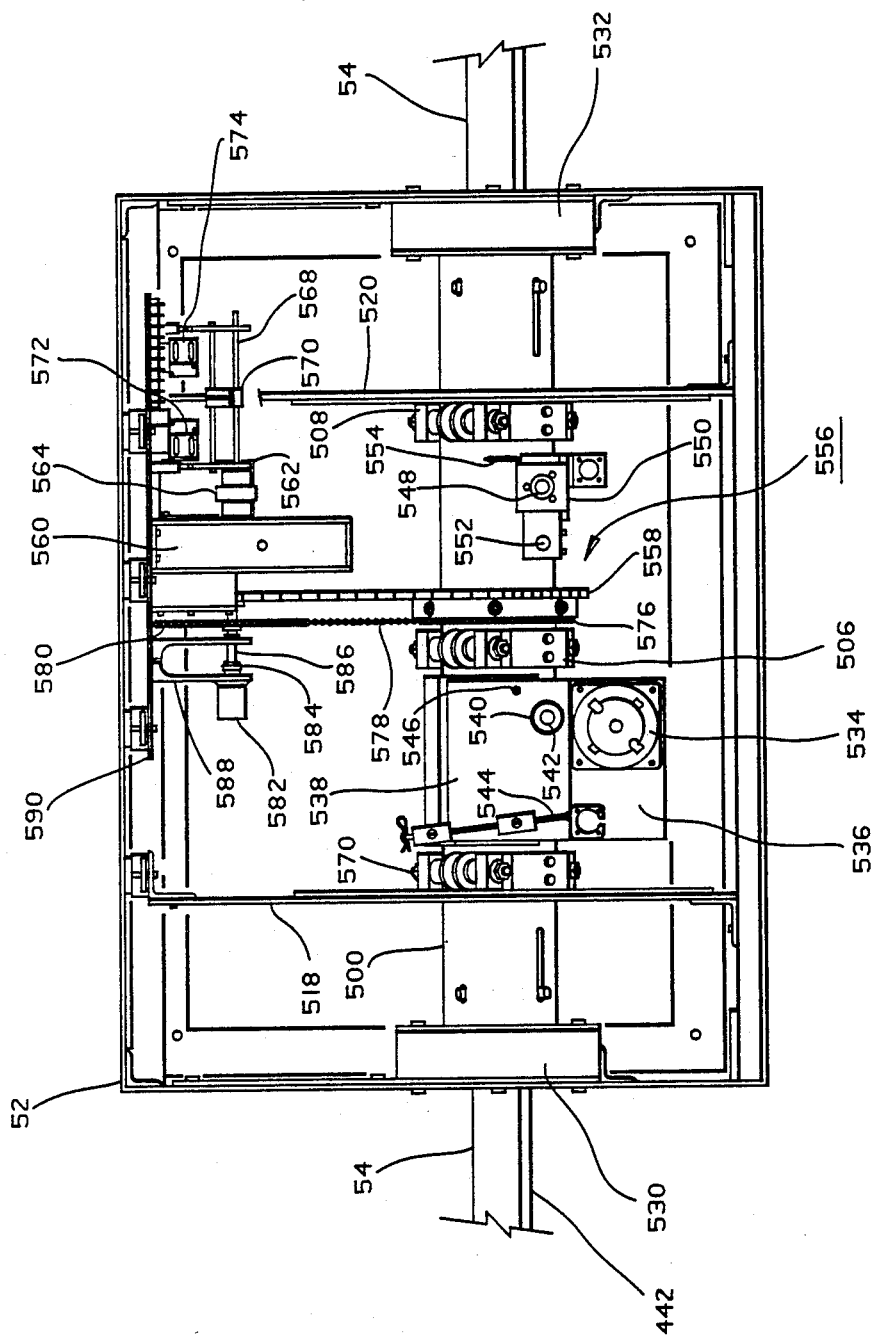
FIG. 18 is a detailed side view of the drive box 52.

The axial drive assembly 502, as illustrated in FIG. 18, includes a motor 534 coupled to a gear reduction box 536 attached to a spring loaded drive mounting box 538. A suitable combination motor-tachometer is available from EG&G Torque Systems of Massachusetts. The axial drive mounting box 538 includes a rack spur gear (not shown) mounted on a spur gear shaft 542 that couples the motion from the motor 34 and gear box 536 to the rack 442 of the drive rod 54. A spring 544 maintains engagement between the rack spur gear and the rack 442 by rotating the axial drive mounting box 538 about pivot 546. The details of the engagement mechanism for the axial drive assembly for the drive rod will be discussed in detail with respect to the details of the resolver engagement mechanism since they are substantially the same.

Figure 20B:
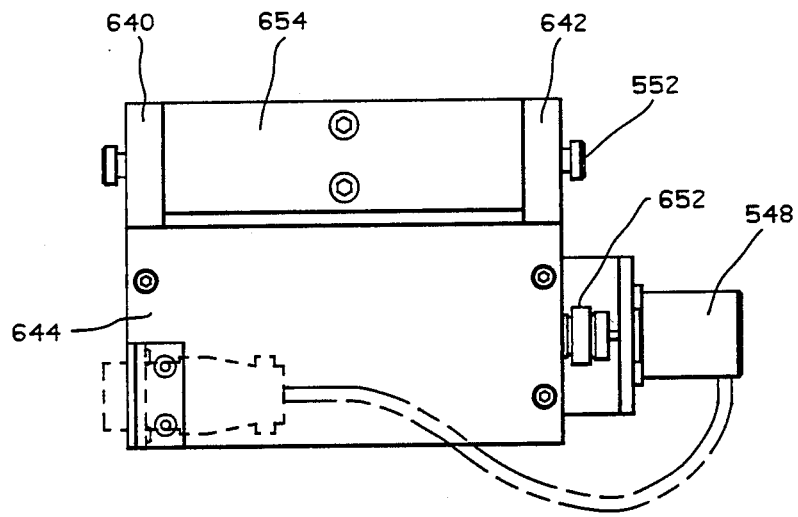
FIGS. 20A and 20B illustrate engagement of the resolver assembly with the drive rod 54.
Figure 20A:
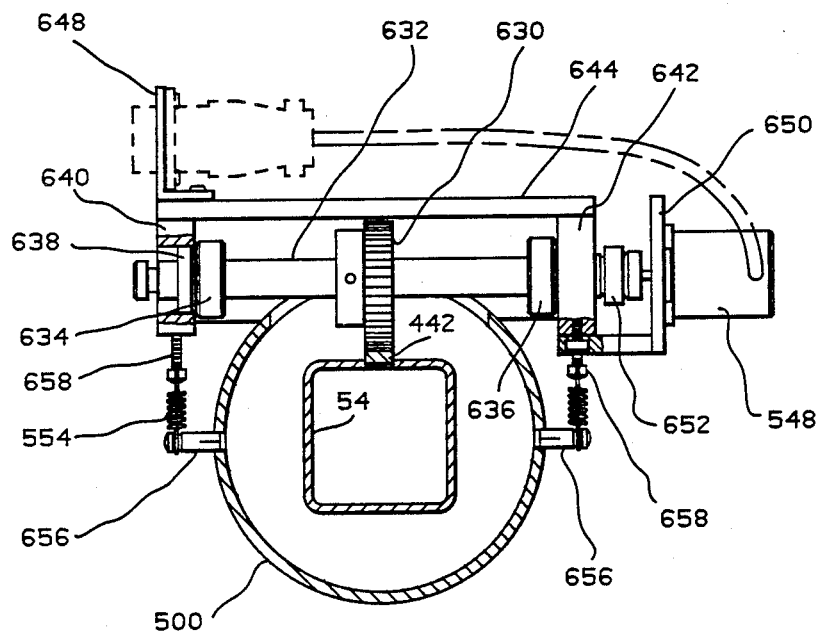

The axial resolver assembly includes a resolver 548, from one of the suppliers previously mentioned, coupled to a resolver gear (not shown) by a resolver gear shaft mounted in a spring loaded resolver mounting box 550, see FIGS. 20A and 20B. The mounting box is rotated about pivot 552 and gear contact with the rack 442 is maintained by springs 554 held at one end by a post attached to the carriage tube 500.

As discussed previously, the drive rod is held by roller assemblies 506-510 which are attached to the rotatable carriage tube 500. The carriage tube 500 is rotated by an attached gear 556 driven by a heavy duty steel chain 558. The chain 558 is coupled to a lubricating fluid type circumferential gear box 560 through a chain drive gear (not shown). The gear reduction box 560, which provides a gear reduction ratio of 30 to 1, is driven by a motor 562 which has at least 500 inchounces of peak torque that is also available from EG&G Torque systems. The gear box is also coupled to the limit switch assembly 516 which includes a wafer coupling 564 driving a worm gear 568. The worm gear moves a limit switch actuator 570 that engages limit switches 572 and 574. The limit switches immediately disable the drive motor 562 to prevent overrotation of the carriage tube 500 in either direction. The carriage tube 500 is designed to rotate more than 400° and carry sufficient cables for the axial assemblies as it rotates. The control electronics limits the rotation to 400° as discussed earlier and the limit switches prevent overrotation should the electronics fail to stop rotation after 400°.

The circumferential resolver assembly includes a belt drive gear 576 attached to the carriage tube and driving belt 578. A belt drive resolver gear 580 rotates with a one to one ratio with belt gear 576 to rotate resolver 582 through a wafer coupling 584 coupled to the resolver 580 by a shaft 586. The belt 578 and gears 576 and 580 are available from W. M. Berg. The resolver gear 580 and resolver 582 are held in position by a mounting bracket 588 attached to a plate 590.

Figure 19B:
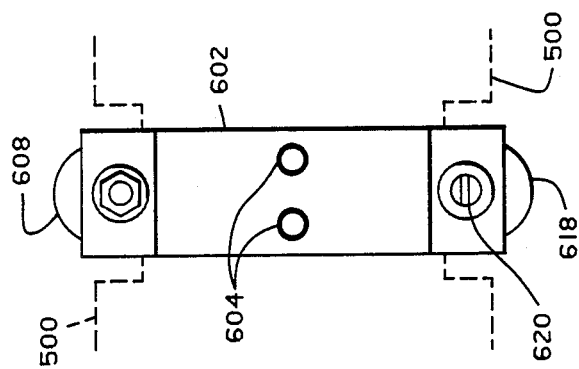
FIGS. 19A and 19B depict the details of a roller assembly.
Figure 19A:
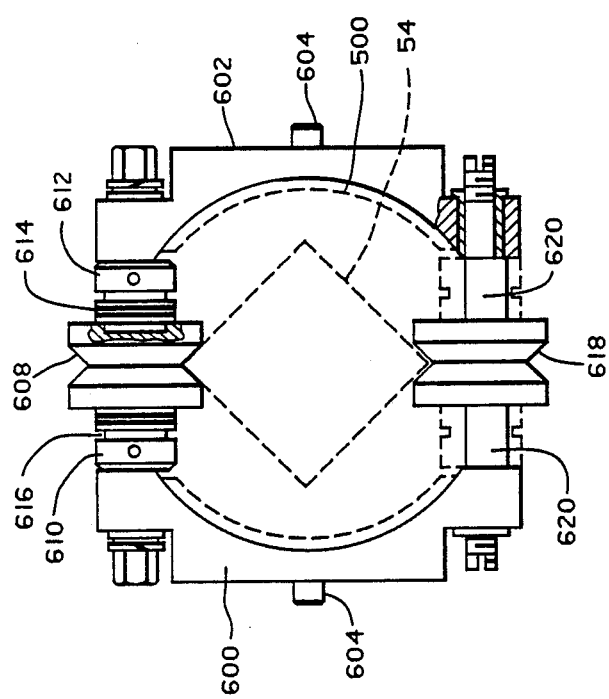

Each of the roller assemblies 506–510 includes carriage tube support members 600 and 602 which are affixed to the carriage tube 500 via bolts 604, as illustrated in FIGS. 19A and 19B. The support members 600 and 602 support a roller shaft 606 which carries a DELRIN drive roller 608. The shaft 606 also carries screw collars 610 and 612 which prevent lateral movement of the shaft 606 and also help maintain the support members in contact with the carriage tube 500. On one side of the roller 608 is a thrust bearing 614 which operates against a spring 616 on the other side of roller 608. The spring 616 and thrust bearing 614 allow the roller 608 to properly align with the drive rod 54 occurs. The lower roller 618 is mounted on an eccentric shaft 620 which, when rotated, provides vertical movement of roller 618 so that a tight fit with the square guide rod 54 occurs. Appropriate set screw collars and spacers are provided on shaft 620 to keep the roller 618 properly aligned.

FIGS. 20A and 20B illustrate the coupling mechanism for coupling the axial resolver to the drive rod 54 and a similar mechanism couples the axial motion assembly to the drive rod 54. The geared rack 442 of the drive rod 54 engages spur gear 630 mounted on shaft 632. The shaft 632 is retained in place by set screw collars 634 and 636. The shaft is supported on each end by a ball bearings 638 fixed in pivot plates 640 and 642. The pivot plates 640 and 642 are held in place by a top plate 644 which holds a connector 648. The resolver 548 is held by a resolver mounting bracket 650 and is coupled to shaft 632 by wafer spring coupling 652. The pivot plates 640 and 642 on the pivot end are held in contact with the carriage tube 500 by a pivot mounting plate 654. The resolver and engagement end of the assembly is held into contact with the rack 442 by springs 554 coupled to the carriage tube 500 by posts 656. Spring tension is adjustable by threaded tension adjustors 658. Only one resolver 648 is shown for the axial direction; however, for safety purposes, a second backup resolver should be attached to the shaft 632. Appropriate gears, shafts, bearings and resolvers for the drive box are available from the suppliers previously discussed.

Figure 21:
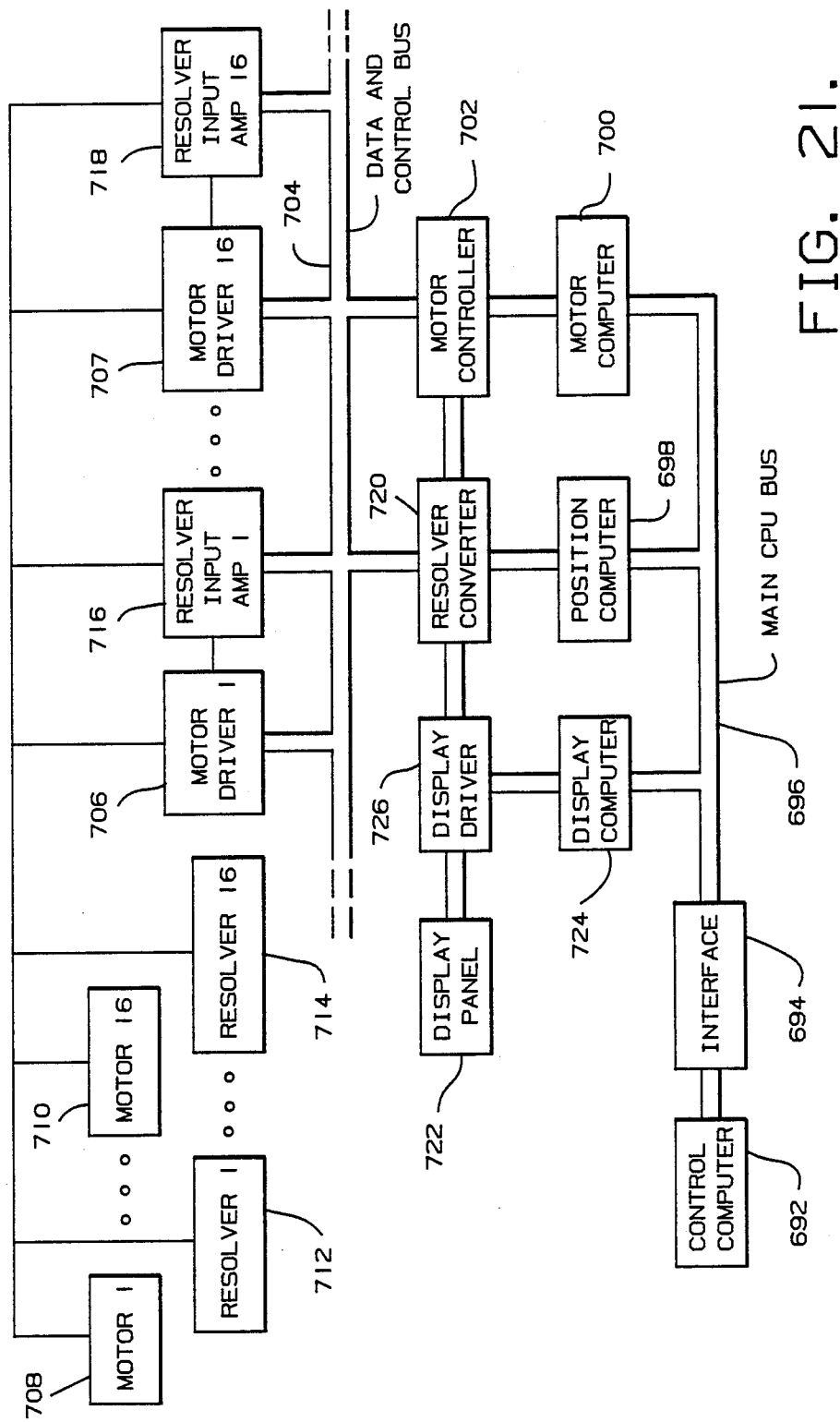
FIG. 21 depicts an electronic control system for controlling motors for various motion axes.

The motors for the 16 scan head motion axes previously discussed are controlled by a computerized control system as illustrated in FIG. 21. In general, a position computer 698 receives a motion command to move one axis of motion from a control computer 692 through interface 694 and over bus 696. The position processor 698 determines the type of motion and issues a command to the motor controller 702 indicating the type of motion and the axis to be moved. The motor processor 700 reads the command and issues a motor speed command including a speed, a direction and a motor driver address to motor controller 702. The motor controller 702 produces a pulse width modulated speed signal which is carried by a data and control bus 704 to all of the motor drivers 706–707. The motor driver having the same address as designated by motor controller 702 accepts the speed signal and direction, and actuates the corresponding one of motors 708–710 over a multiple conductor cable having direct connections between the associated motor driver and motor. A corresponding resolver, as previously discussed, which is mechanically linked to the object being driven by the motor, responds with resolver position signals to the directly connected resolver input amplifiers 716–718 over separate resolver bundles in the multiple bundle cable. The multiple bundle cable includes shielded twisted pairs for resolvers and motors, and microminiature coaxial cables for transducer signals. The resolver input amplifier for the corresponding motor driver is actuated by a signal line between the motor driver and the resolver input amplifier to place the resolver signals on a resolver signal portion of data and control bus 704. Note the data and control bus 704 is a separate and different bus than the transducer signal bus discussed in the related application entitled Ultrasonic Signal Processing System Including A Flaw Gate. The resolver signal, output by the activated resolver input amplifier, is applied to a resolver converter 720 which converts the analog resolver signals into digital values. The motor computer 698 supplies both the position and motor address to a display computer 724. The display computer 724 controls display panel 726 to indicate to the operators the position of the object being controlled.

A more detailed discussion of the sequence described above, will be provided in conjunction with the flowcharts, for the various computers, to be discussed later. The computers for the various motion axes provided on the scan head 46 and by the drive box 52 include Z80 processors available from Zilog and appropriate amounts of RAM and PROM memory, and are structured similar to those described in the related application entitled Ultrasonic Signal Processing System Including A Flaw Gate and will not be discussed in detail here. The motor 700, position 698 and display 724 computers being three such motion axis computers, have a structure identical to the structure illustrated and described in the related application entitled Ultrasonic Signal Processing System Including A Flaw Gate and will not be discussed in detail here. The registers, latches, etc., discussed hereinafter, are standard off-the-shelf items unless otherwise indicated.

Figure 22:
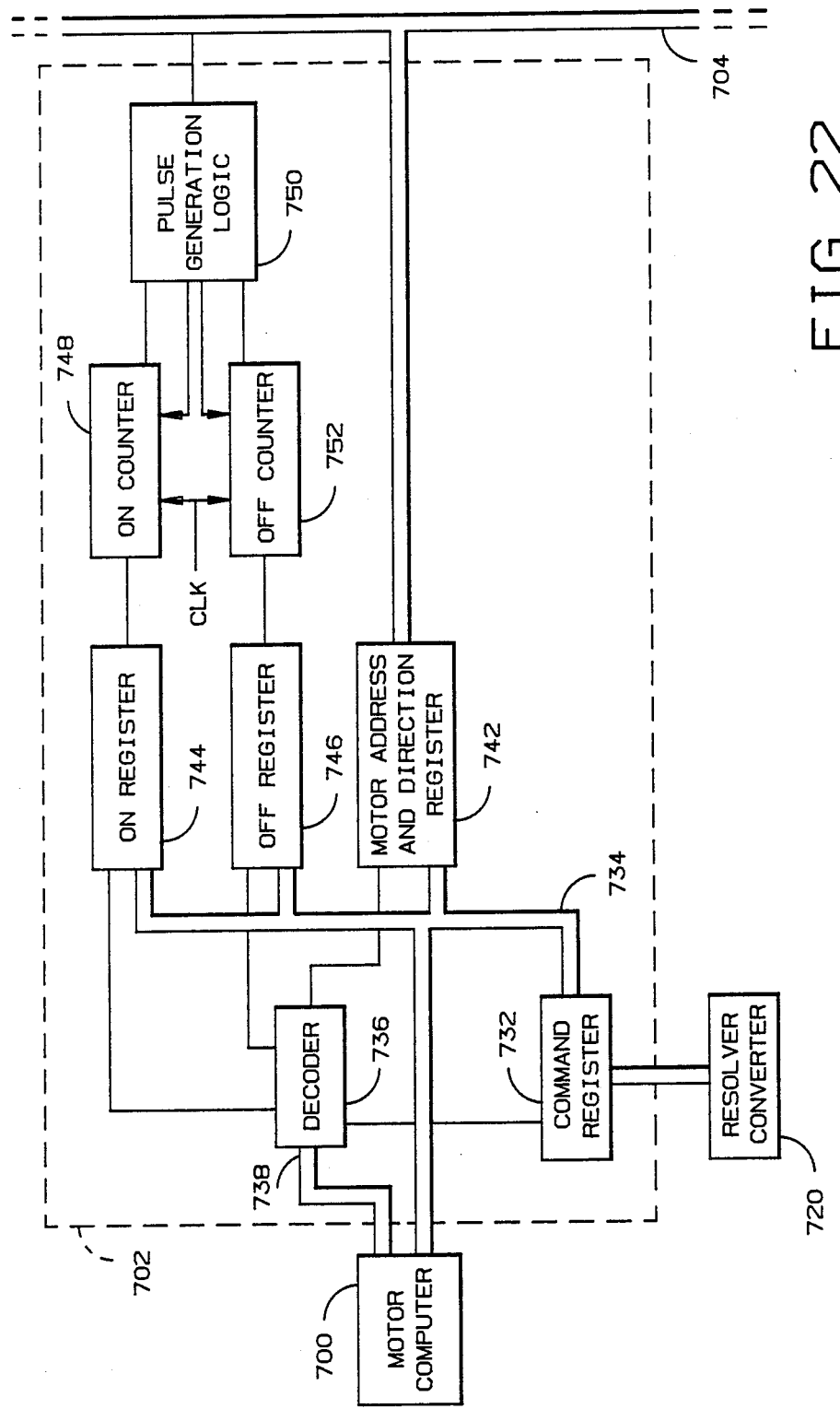
FIG. 22, illustrates components of motor controller 702.

A command register 732 in motor controller 702, as illustrated in FIG. 22, which is coupled to the position computer 698, receives a command which is retrieved by the motor computer 700 over data bus 734 by activating decoder 736 over address bus 738. The computer 700 stores and the motor address (motion axis) and direction in register 742. The motor address and direction are applied to the motor drivers over bus 704. Based on the desired speed (rate), On and Off pulse time registers 744 and 746 are loaded by computer 700. On and Off registers 744 and 746 determine the On time and Off time of the pulse in the pulse width modulation control signal applied to the motor drivers. A pulse width modulated signal is used to prevent the corrosion that occurs in water when a constant D.C. voltage is applied. The On register loads a down counting On counter 748 which controls pulse generation logic 750 to create the On portion of the pulse width control pulse. The pulse generation logic includes OR gates which are connected to the count outputs of the On counter 748 and produce an On control signal whenever the counter 746 has non zero contents. The OR gates drive the set input of a set/reset flip-flop which produces the pulse width controlled signal. A NAND gate also monitors the output of the On counter 748 and produces a load signal for a down counting Off counter 752 whenever On counter 748 reaches zero. The Off counter pulse portion of the generation control logic 750 is identical to that discussed above for the On counter 748 whereby OR gates control the reset input of the set/reset flip-flop and a NAND gate provides a load pulse to On counter 748. Even though two counters are discussed above to reduce the number of system components, it is possible to use a single counter if appropriate logic controlled gating circuitry is provided.

Figure 23:
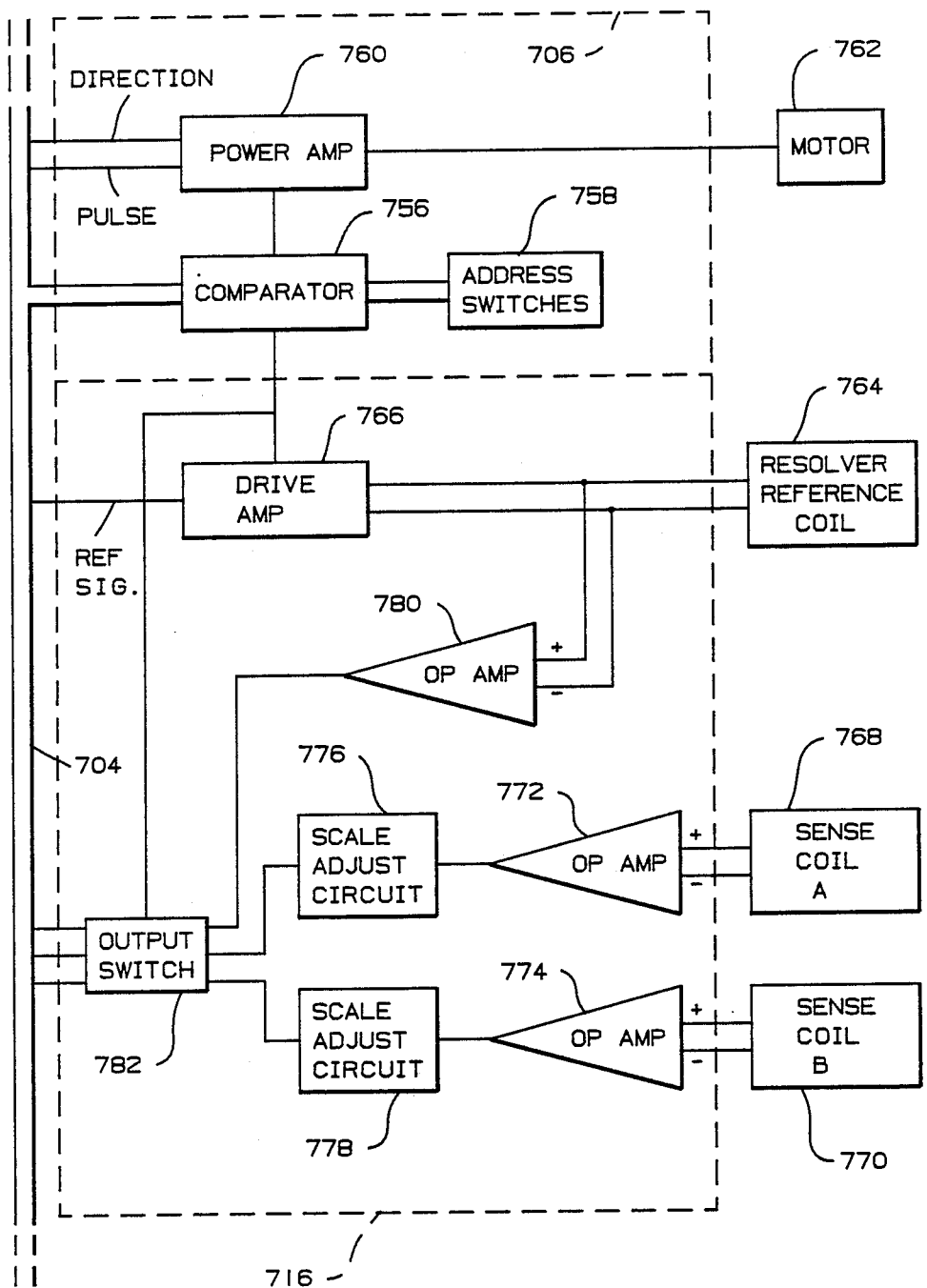
FIG. 23 illustrates components of each motor driver 716 and resolver input amplifier 706.

FIG. 23 illustrates the components of each motor driver and each resolver input amplifier. In the motor driver 706, a comparator 756 compares the address on bus 704 with the address produced by address switches 758 such as dip switches and produces an enable signal to power amplifier 760. The power amplifier 760, when activated, receives the direction signal and pulse width controlled signal and produces a polarized motor driver signal for motor 762. As the motor 762 turns, a resolver reference coil 764, receives a reference sinusoidal signal from a drive amplifier 766 based on a 400 Hertz input sin wave reference signal, stimulates sense coils A and B 768 and 770 when the comparator 756 provides the enable signal. The sense coil signals are amplified by differential amplifiers 772 and 774 and applied to scale adjust circuits 776 and 778. The scale adjust circuits 776 and 778 match the sense coil signals for different resolvers to the input requirements of the single resolver converter 720. The scale adjusted sense coil signals, along with a feedback of the reference signal through operational amplifier 780 are gated by the enable signal from comparator 756 applied to an analog output switch 782. The reference signal and sense coil signals are carried by bus 704 to the resolver converter 720.

Figure 24A:
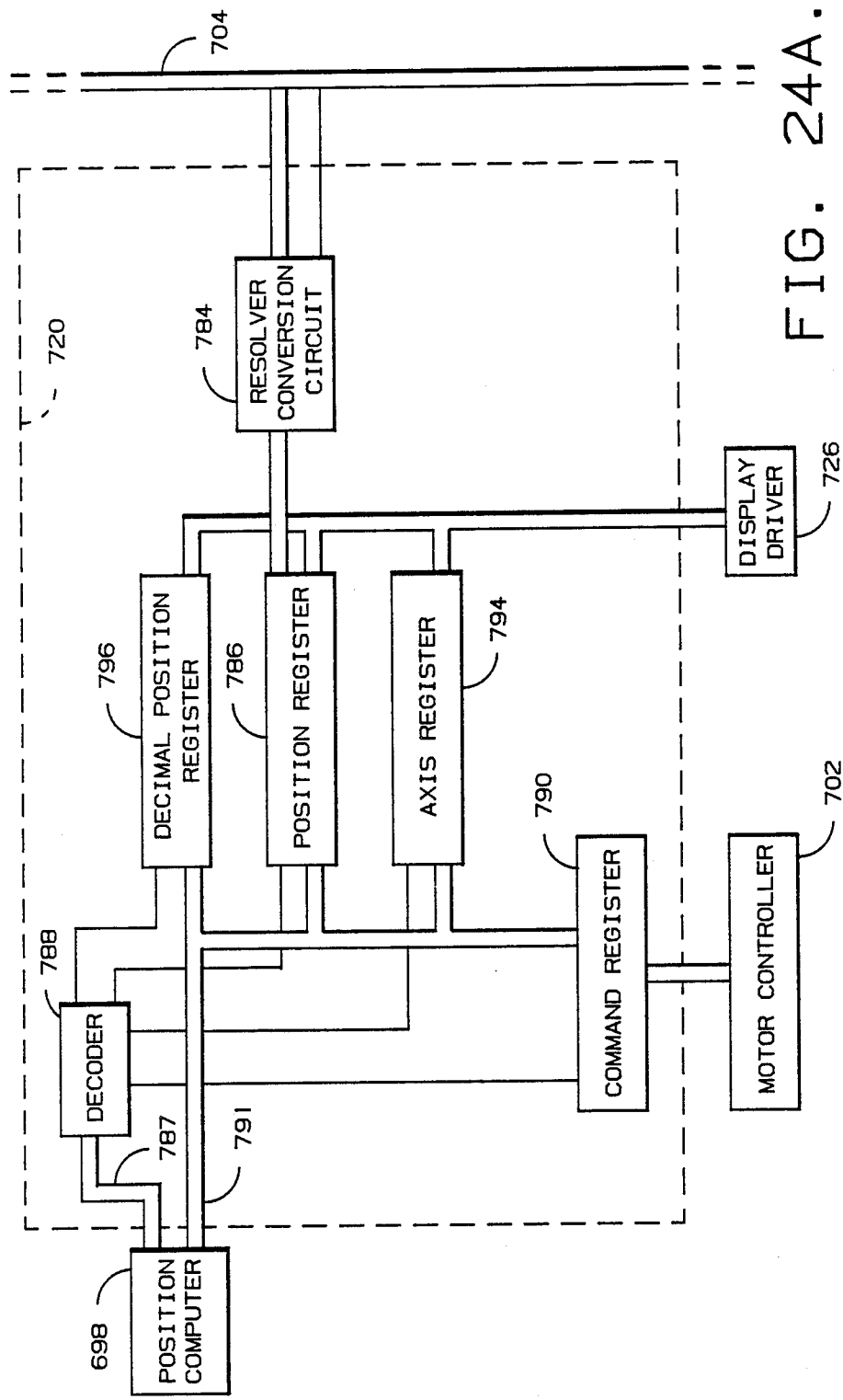
FIG. 24A depicts components of a resolver converter board.

The resolver converter board 720, as illustrated in FIG. 24A, includes a resolver conversion module 784 available from Analog Devices of Massachusetts. The resolver conversion circuit 784 produces a 14 bit position which is continuously stored in position register 786. The position register 786 makes the position available to the position processor 698 when activated by decoder. Whenever a command needs to be sent to the motor controller 700, the command is sent through command register 790. The position computer also has available an axis register 794 for the current axis being stored. A decimal position register 796 is available along with the axis register 794 to display driver 726. A detailed discussion of the sequence in which the components on the resolver board 720 are used will be provided with respect to later discussed computer flowcharts.

Figure 24B:
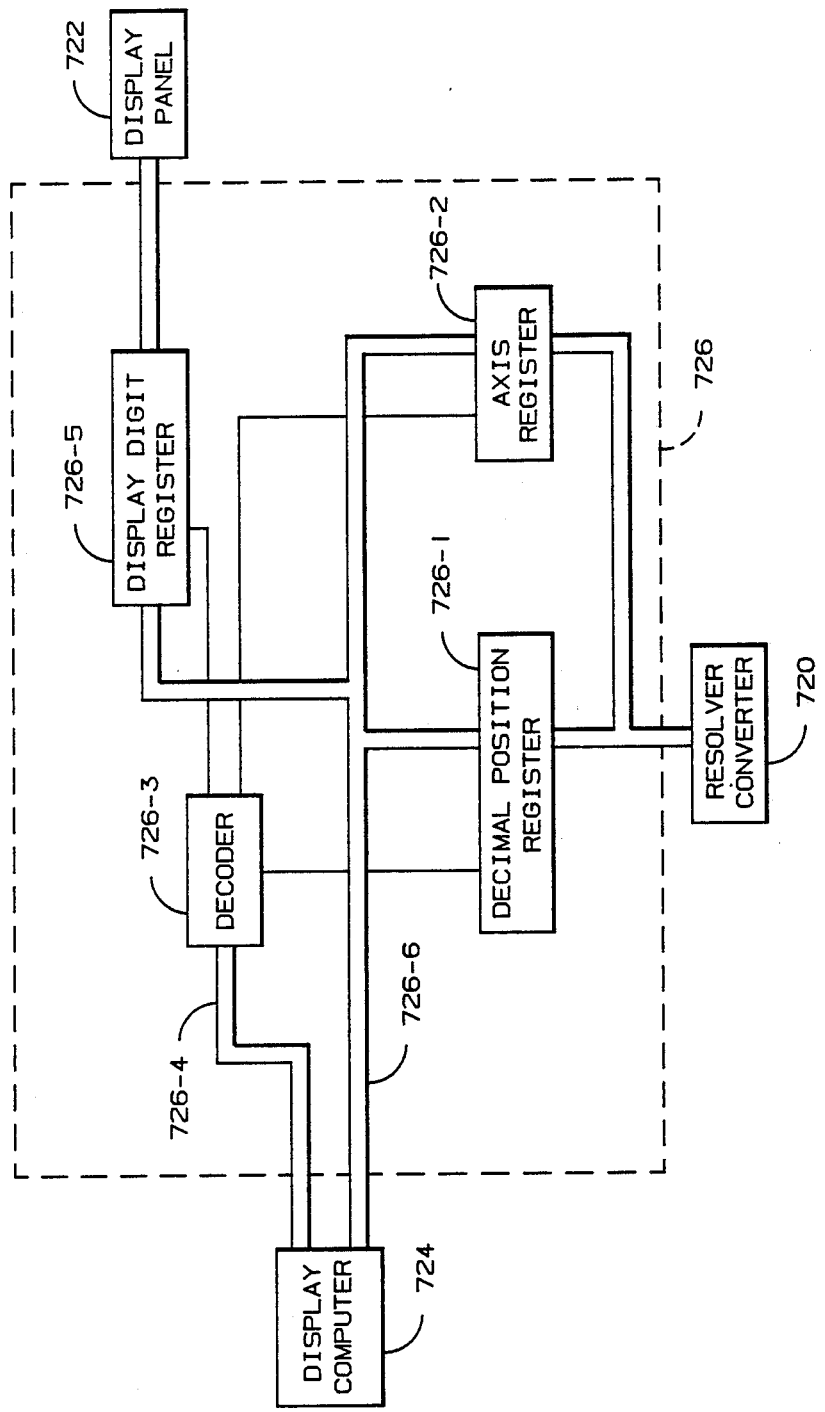
FIG. 24B shows the components of display driver 726.

The display driver 726, as illustrated in FIG. 24B, has a decimal position register 726-1 and an axis register 726-2 that are loaded by the resolver converter 720 as the position of the current axis changes and as different axes are selected. The display computer 724 can read these registers by activating decoder 726-3 over the address bus 726-4. The display computer 724 loads the display panel 722 via the display digit register 726-5 to display the decimal position value and axis value for the operator.

Figure 25:
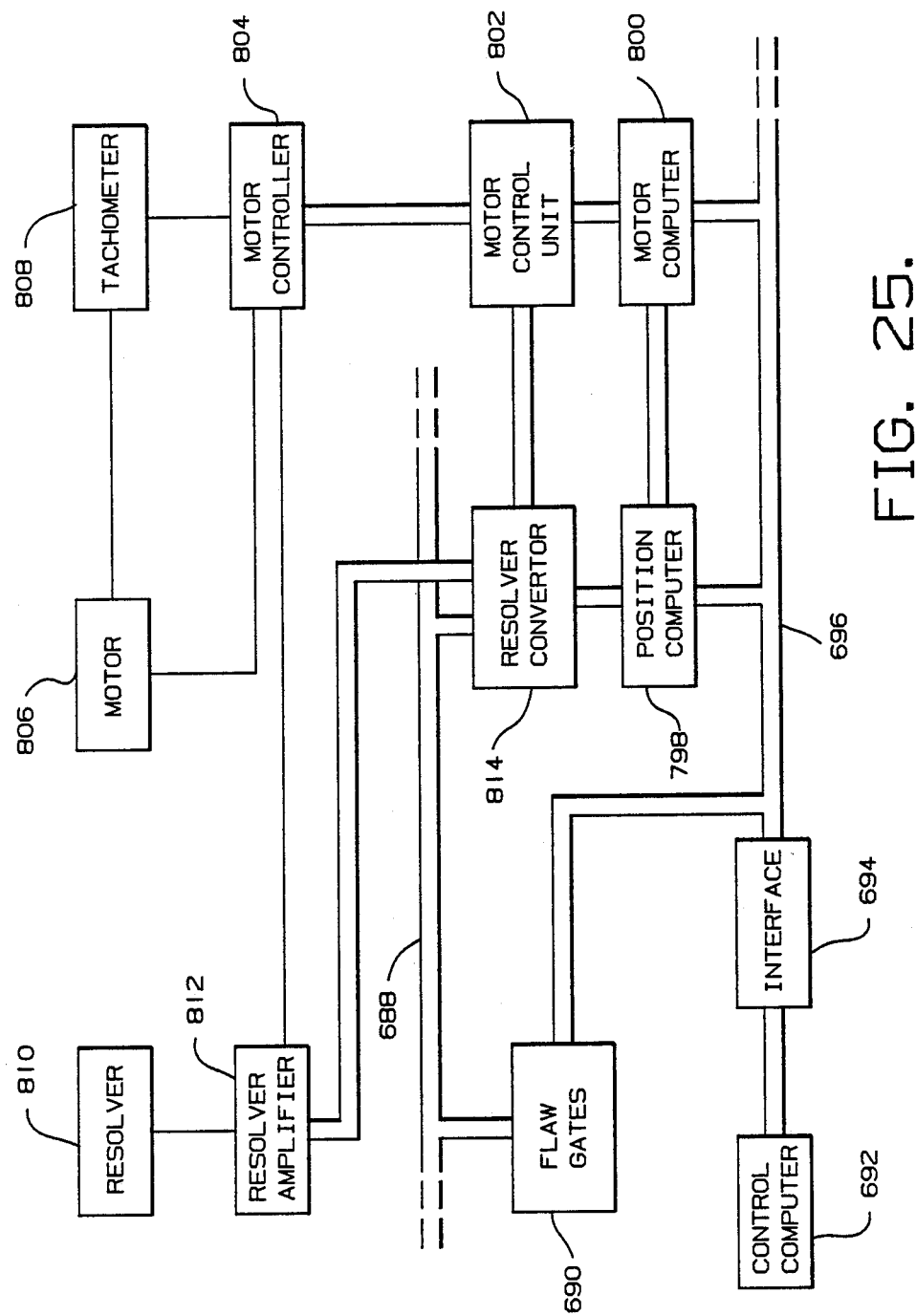
FIG. 25 shows the control system for the axial and circumferential motions.

The control system for the axial and circumferential motions is illustrated in FIG. 25. The control system for the axis and circumferential motions are identical and for simplicity only a single control system is shown. The computers discussed for the axial and circumferential motions include the same processors and conventional circuit elements such as RAMS and PROMS, as previously discussed, unless otherwise indicated. The instructions for operating the axial and circumferential systems separately activate a position processor 798 and a motor processor 772. The motor processor 800 sends a speed control command to a motor control unit 802 which activates a motor controller 804 over the bus 704. The motor controller 804 is an EG&G Torque Systems motor controller model CO501 and it provides appropriate speed control to motor 806. The motor controller 804 monitors the speed of motor 806 through a tach 808. It is possible to interpose a manual interface between motor controller 804 and bus 704 which will allow manual control of the motor 806 if desired. As the motor moves, resolver 810 produces resolver signals as discussed previously with respect to the scan head control system. The resolver signals are amplified by a resolver amp 812 which is identical to the resolver amp previously discussed. The resolver signals are converted by a resolver converter 814 which is substantially the same as the previously discussed resolver converter in which the resolver converter 814 sends a speed and direction command to the motor control unit. The resolver converter also has appropriate latches for loading the digits of panel display 815. The position determined by the resolver can be placed on the bus 688 to allow the flaw gates 690, as discussed in the related application entitled Ultrasonic Signal Processing System Including A Flaw Gate, to record the position, this capability is particularly required of the circumferential control system during circumferential scans. The details of the procedures executed by the motor processor 800 and position processor 798 will be discussed in detail later.

Figure 26:
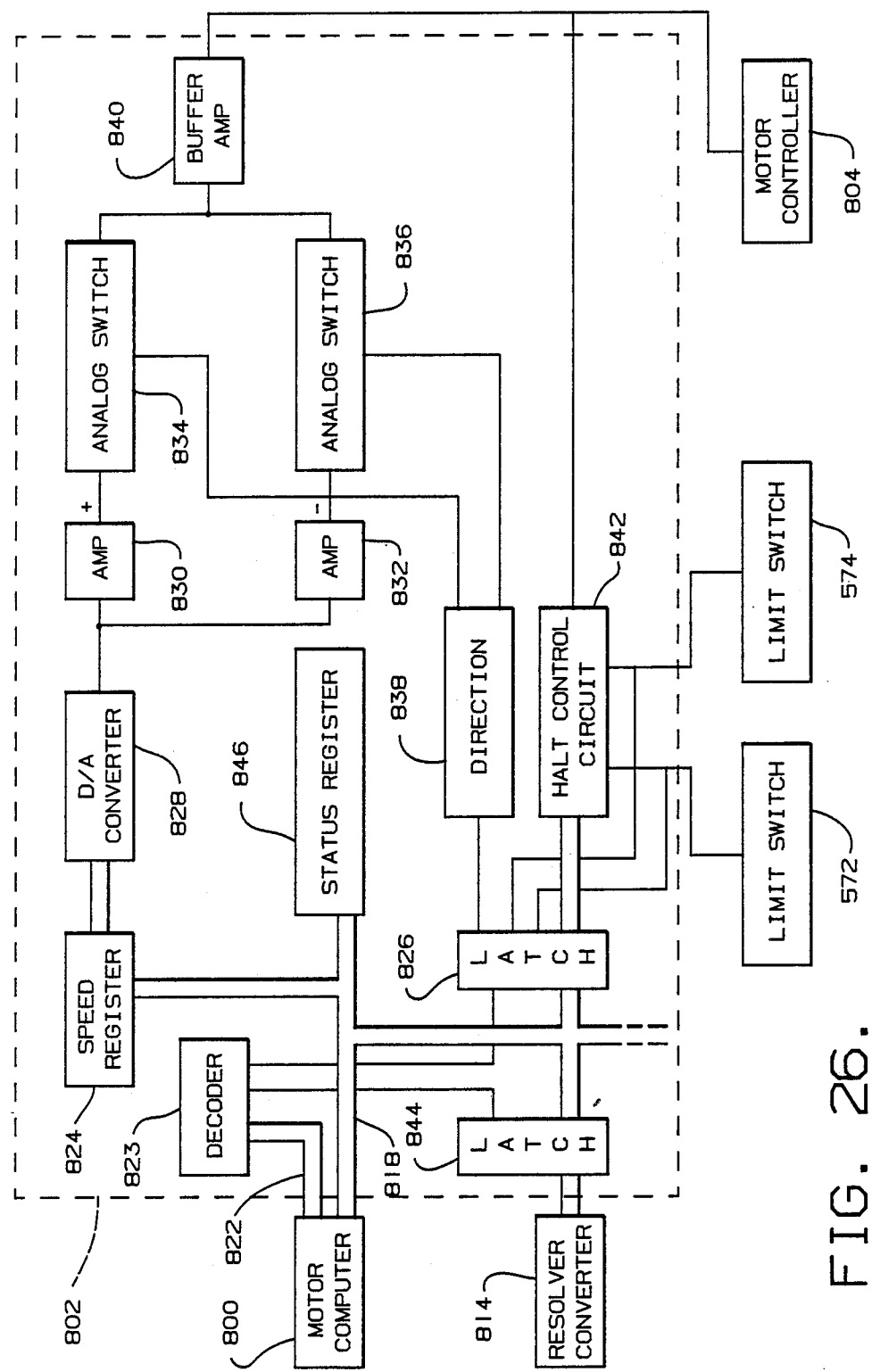
FIG. 26 is a diagram of a motor control unit.

A speed and direction command can be sent to the motor computer 800 either via latch 844 from resolver converter 814 or via RAM memory or set by control computer 692 through interface 694. The motor processor 800 then provides a speed control word to the motor control unit 802, illustrated in FIG. 26 over address data bus 818 by activating decoder 823 over address bus 822. The speed control word includes a speed portion stored in a speed register 824 along with a direction signal and a halt control signal stored in latch 826. A digital-to-analog converter 828 converts the speed portion of the speed control word into both a positive and a negative analog signal using amplifiers 830 and 832. The output of the amplifiers 830 and 832 are applied to analog switches 834 and 836 controlled by a direction circuit 838 that can be a NOT gate in which the input is connected to one analog switch 834 and the output is connected to the other analog switch 836. The output of the selected analog switch is applied to a buffer amplifier 840 which applies the polarized analog speed control signal to the motor controller 804. The outputs of limit switches 572 and 574 are applied to a halt control circuit along with the halt signal from latch 826. A halt control circuit 842 which can be an OR gate, applies a halt signal to the motor controller 804 whenever one of its inputs is active. The motor control unit 802 also includes a latch 844 for receiving the current speed and direction from the resolver converter 814 and a status register accessible by the control computer 692.

As discussed previously with respect to FIG. 23, the scan head has sixteen independently controllable motion axes, each having a different address ranging from three to twenty-one. The motion axes are divided into three types: chuck motion, radial support motion and tilt. Each of the types includes a scale factor and four motion ranges which correspond to four different speeds where a movement in a higher range corresponds to a longer movement distance and consequently has a higher speed. The speeds correspond to On and Off counts of the pulse width drive pulse supplied to the motor driver amplifiers, as previously discussed. The preferred scale factors (for a single resolver revolution), ranges and speeds for each type are listed below in Table 1:

TABLE 1

| Type | Scale Factor | Range 1 | Speed 1 | Range 2 | Speed 2 |
|---|---|---|---|---|---|
| Chuck | 2.0027" | .002" | 100/400 | .01" | 200/300 |
| Radial Support | 1.0013" | .001" | 60/600 | .01" | 60/500 |
| Tilt | 360° | .09° | 50/700 | 2° | 50/600 |
| | Range 3 | Speed 3 | Range 4 | Speed 4 | |
| Chuck | .05" | 300/200 | .1" | 400/80 | |
| Radial Support | .05" | 60/400 | .1" | 100/30 | |
| Tilt | 10° | 50/500 | 20° | 50/400 | |

The control computer 692 controls the type of movement, the speed, the direction and the motion axis, by loading a speed command into the memory of the position processor 698 and necessary data into the memory of both the position 698 and motor 700 processors. The position processor 698 and motor processor 700 then perform the necessary control, allowing the control computer 692 to process data to determine the location of flaws, as discussed in the related application entitled Ultrasonic Signal Processing System Including A Flaw Gate and discussed later herein.

Figure 27:
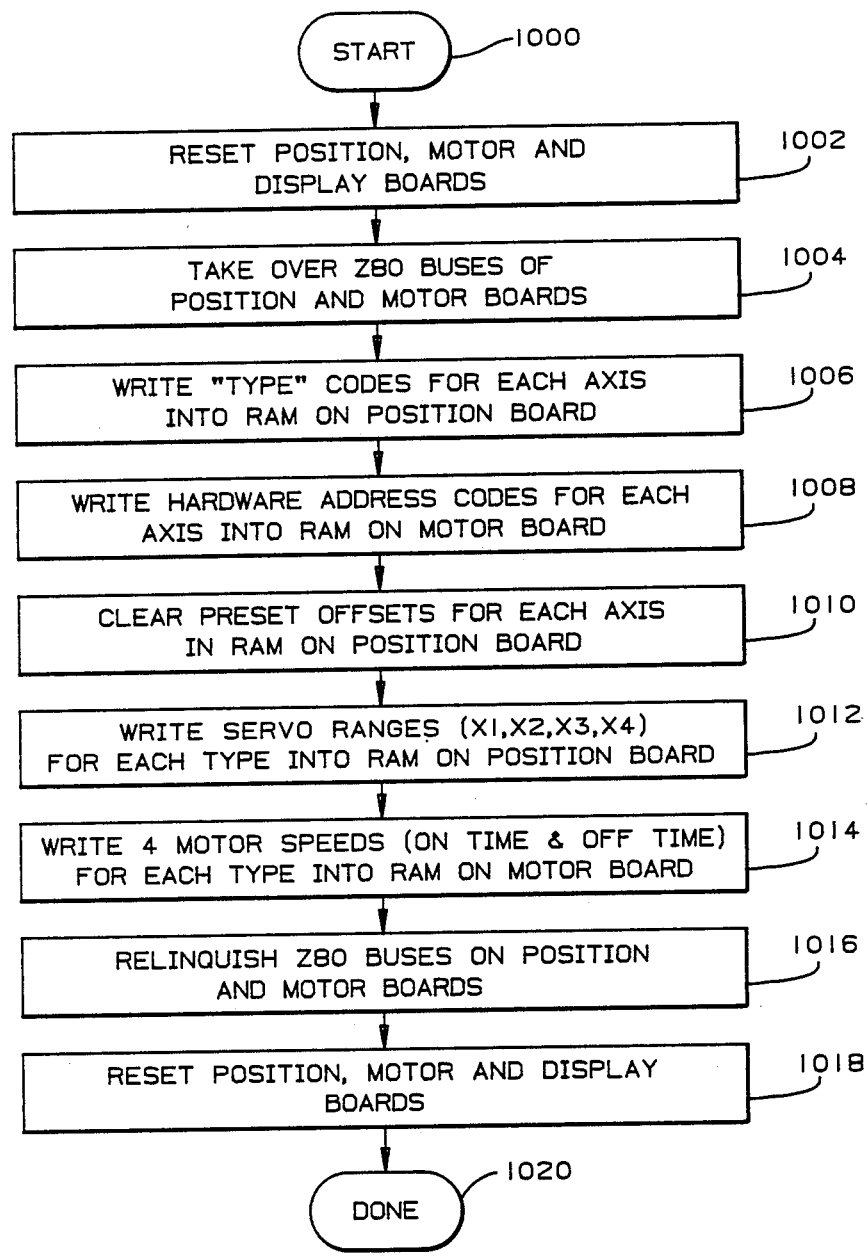
FIG. 27 is a flowchart of a procedure for initializing position 698, motor 700 and display processors 724 for the scan head 46.

Prior to any control action, the main control computer 692 must load the position processor with the contents of Table 1, illustrated above, as depicted by the procedure of FIG. 27. A preferred control computer 692 is a Digital Equipment Corporation PDP—11/73, however, other high speed, mini computers can be used. The initialization procedure for scan head motions starts by resetting 1002 the position, motor and display processors. Next, the control computer 692 takes over 1004 the buses of the position 698 and motor 700 processors, as discussed in detail in the related application entitled Ultrasonic Signal Processing System Including A Flaw Gate. The control processor 692 then loads the memory of the appropriate processors with the type codes 1006, hardware address for each axis 1008, position offsets for each axis, servo ranges 1012 and motor speeds 1014, after which the control computer releases 1016 the buses and resets 1018 the processors.

Figure 28:
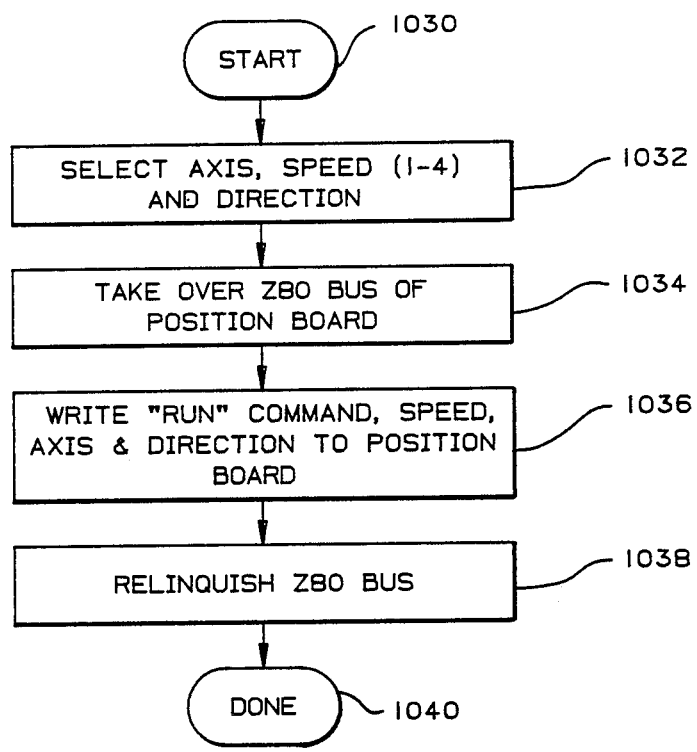
FIG. 28 depicts a continuous motion start procedure performed by the control computer 692.

When the main computer wants to move a particular axis using a continuous motion, the procedure illustrated in FIG. 28 is performed. First, the control computer 692 determines 1032 the desired axis, speed and direction. This determination could be made via a scan control program or by an operator through a keyboard in the control computer 692. The control computer 692 then seizes 1034 the position processor 698 bus and loads 1036 a run command, including speed, axis and direction into the memory of the position processor 698 and then relinquishes 1038 the bus.

Figure 29:
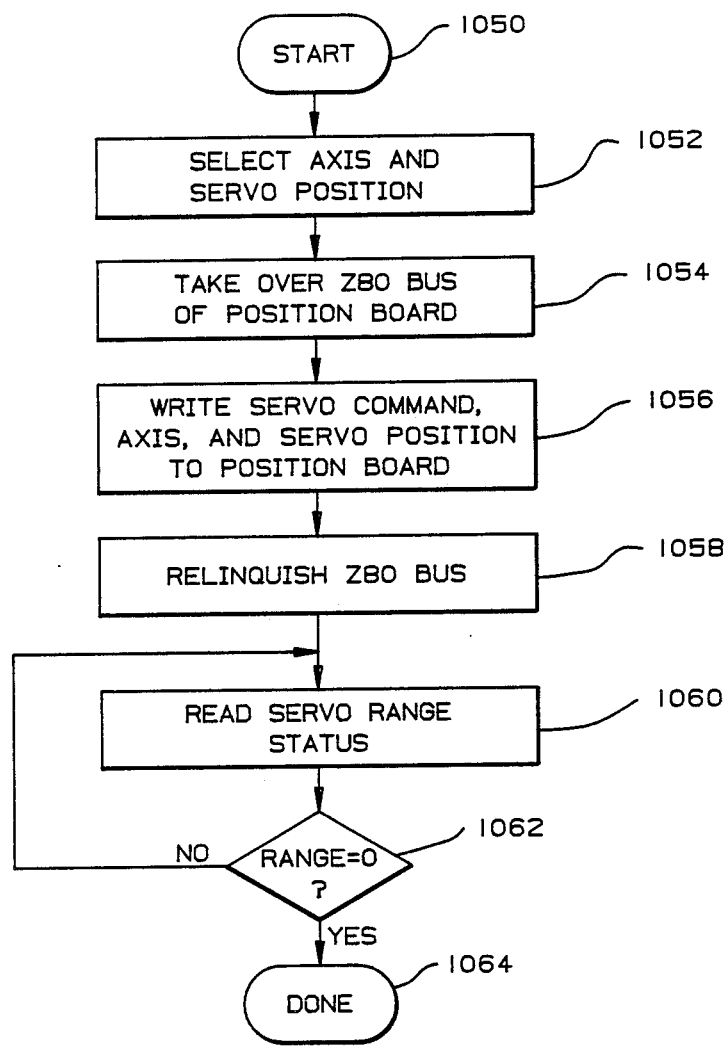
FIG. 29 is a procedure for servo control performed by the control computer 692.

If servo control of a scan head axis is desired, the control computer 692 executes the procedure of FIG. 29. During this procedure, the control computer selects 1052 the axis and servo position, takes over 1054 the bus of the position processor 698, loads 1056 the servo command including the axis and servo position into the memory of the position processor 698 and relinquishes 1058 the position processor 698 bus. The main computer then monitors 1060 the servo range status stored in the status register of the position processor 698 and when the range equals zero 1062, servo control is accomplished.

Figure 30:
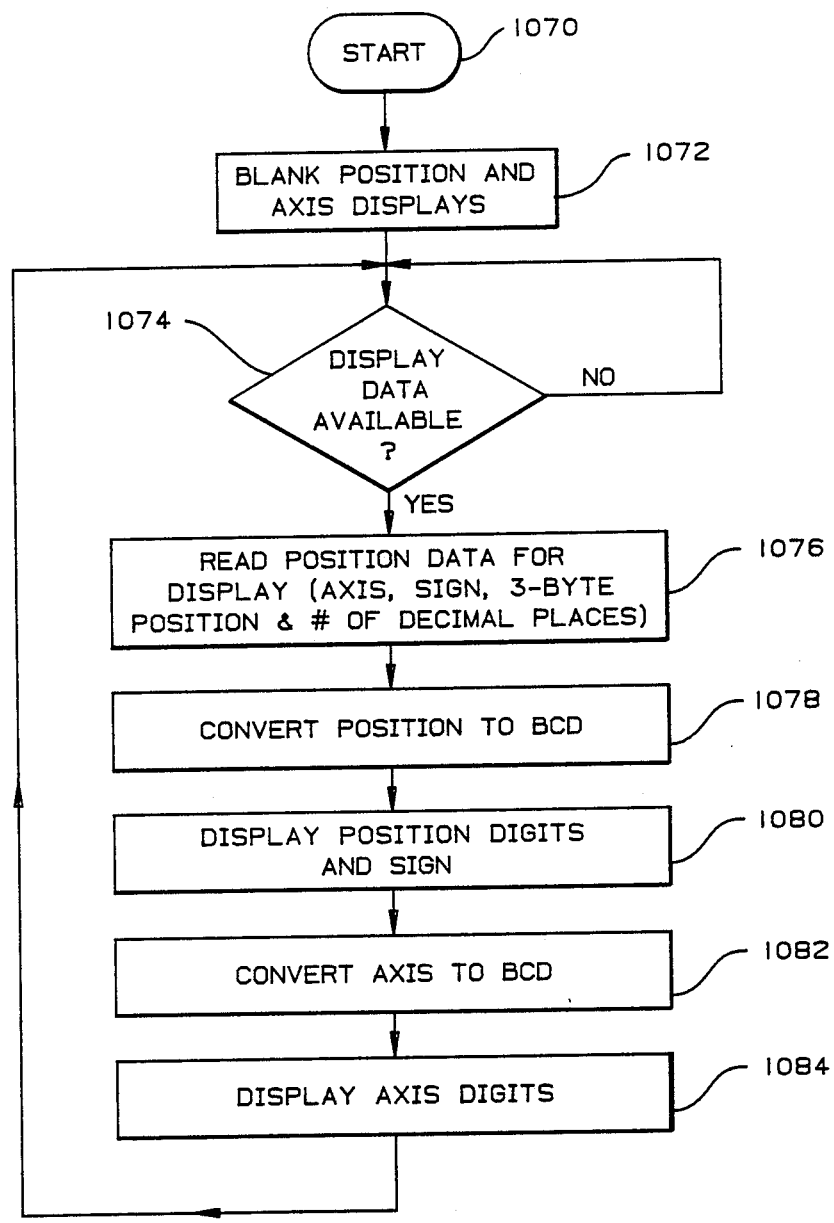
FIG. 30 depicts a procedure performed by the display processor 724.

Throughout any scan or motion performed by the scan head 46, the axis being controlled as well as the position of that axis are displayed on a display panel 722 by display computer 724 via display driver 726. The display processor 724 controls the display and retrieves the pertinent data in accordance with the continuously looping procedure illustrated in FIG. 30. At the beginning, the position and axis displayed on the display panel 726 are blanked 1072. Then the processor 724 determines 1074 whether position data is available for display by examining the appropriate registers in the display driver 726. If data is available for display, it is retrieved 1076 and converted into binary coded decimal and displayed 1078-1084. The display processor 724 then reexecutes the loop thereby continuously displaying the current axis and position being controlled.

Figure 31A:
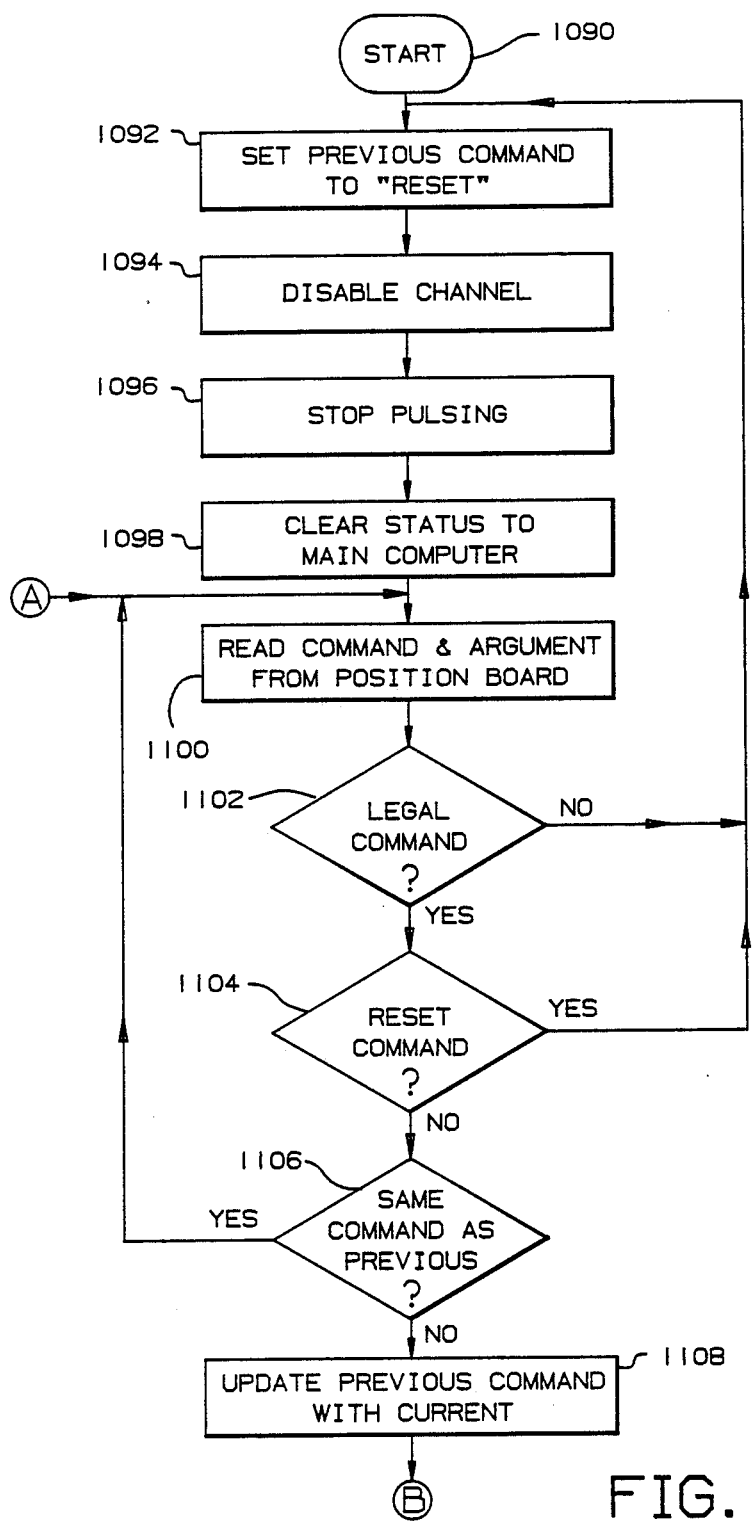
FIGS. 31A and 31B are flowcharts for a motor control procedure executed by the motor processor 700.
Figure 31B:
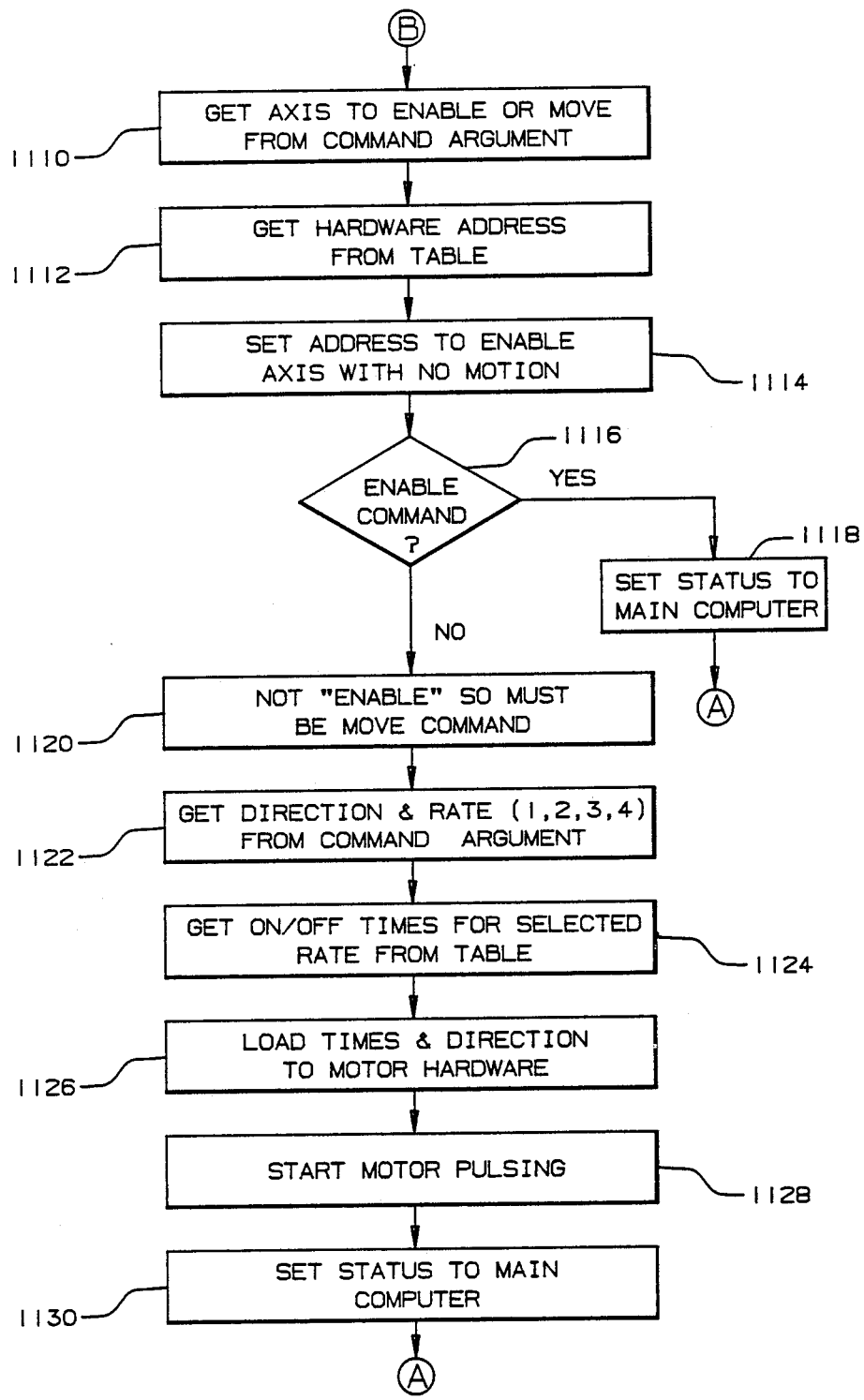

The procedure executed by the motor processor 700 is illustrated in FIGS. 31A and 31B. At the beginning, the previous command stored in the random access memory of the motor processor 772 is set 1092 to the reset command after which the channel over which the axis address is transferred is disabled 1094. The processor 772 then stops pulsing by loading a count of zero into each count register in the motor controller and then indicates a clear status to the control computer 692. The start of motor movement includes reading 1100 a command and associated argument from the command register coupled to the position board. The command is then checked to see if it is a legal command and if it is not a legal command the processor 700 forces a reset command. Next, it is determined 1104 whether the command is a reset command and if so, the reset and disable procedure is executed again. If it is not a reset command, a determination is made as to whether the command is the same as a previous command. If so, the motor computer 700 continues reading commands. If the command is different, the previous command stored in memory is updated 1108 with the current command. Next, the axis is retrieved 1110 from the command argument followed by obtaining 1112 the hardware address for the axis from an internal table constructed during the initialization procedure. Next, the address is loaded 1114 into the axis/motor address register. At this time, the pulse control circuitry is not enabled and, as a result, no motion is occurring at this time. If the command is an enable command, an enabled status is communicated 1118 to the control computer 692 through the status register. If the command is not an enable command the command must be a move command so the direction and speed are retrieved 1122 from the command argument. The On and Off times for the speed are obtained 1124 from the table previously mentioned and loaded 1126 into the motor controller 702 followed by an enable signal that starts the pulsing 1128. Status is then communicated 1130 to the control computer 692 through the status register.

Figure 32A:
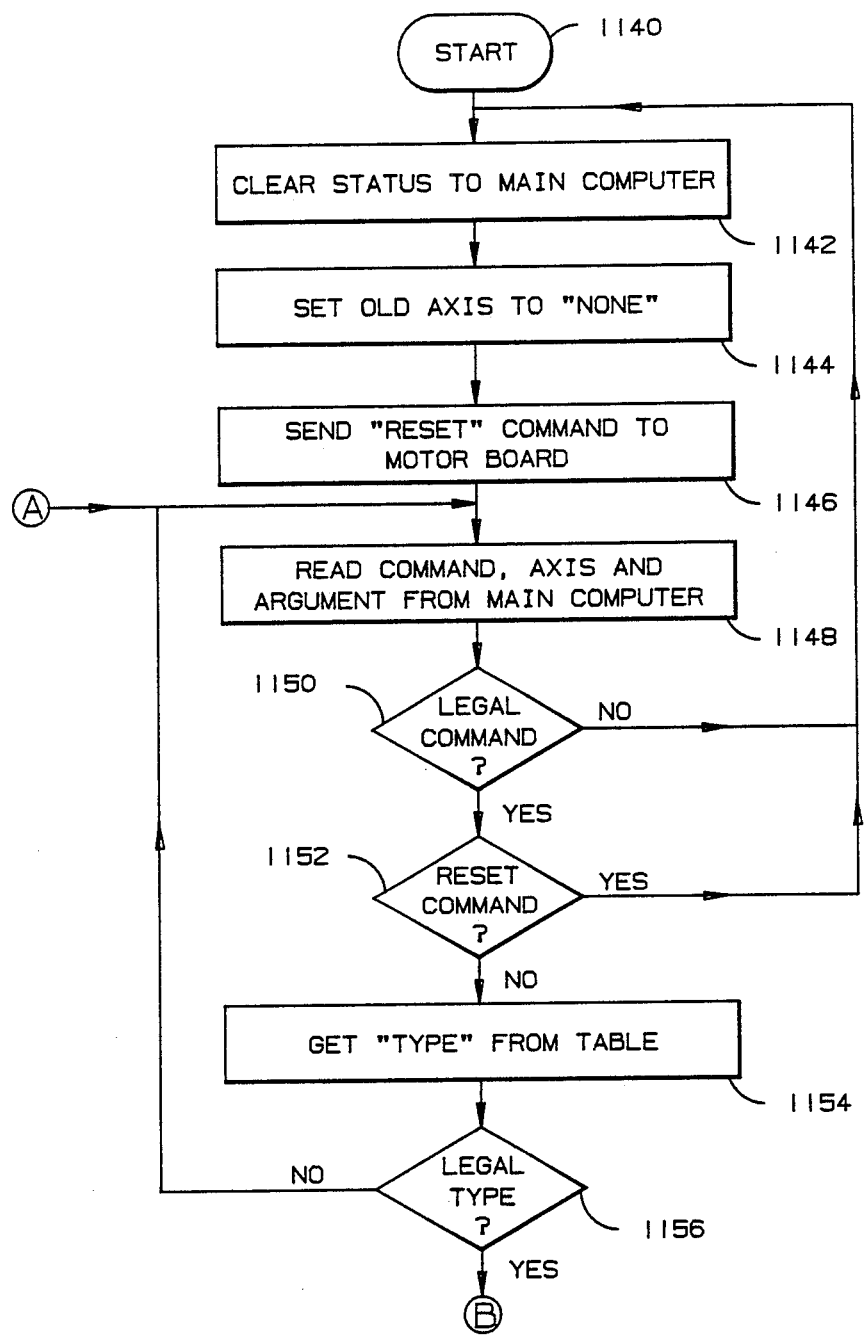
FIGS. 32A–32B are parts of a procedure executed by the position processor 698.
Figure 32B:
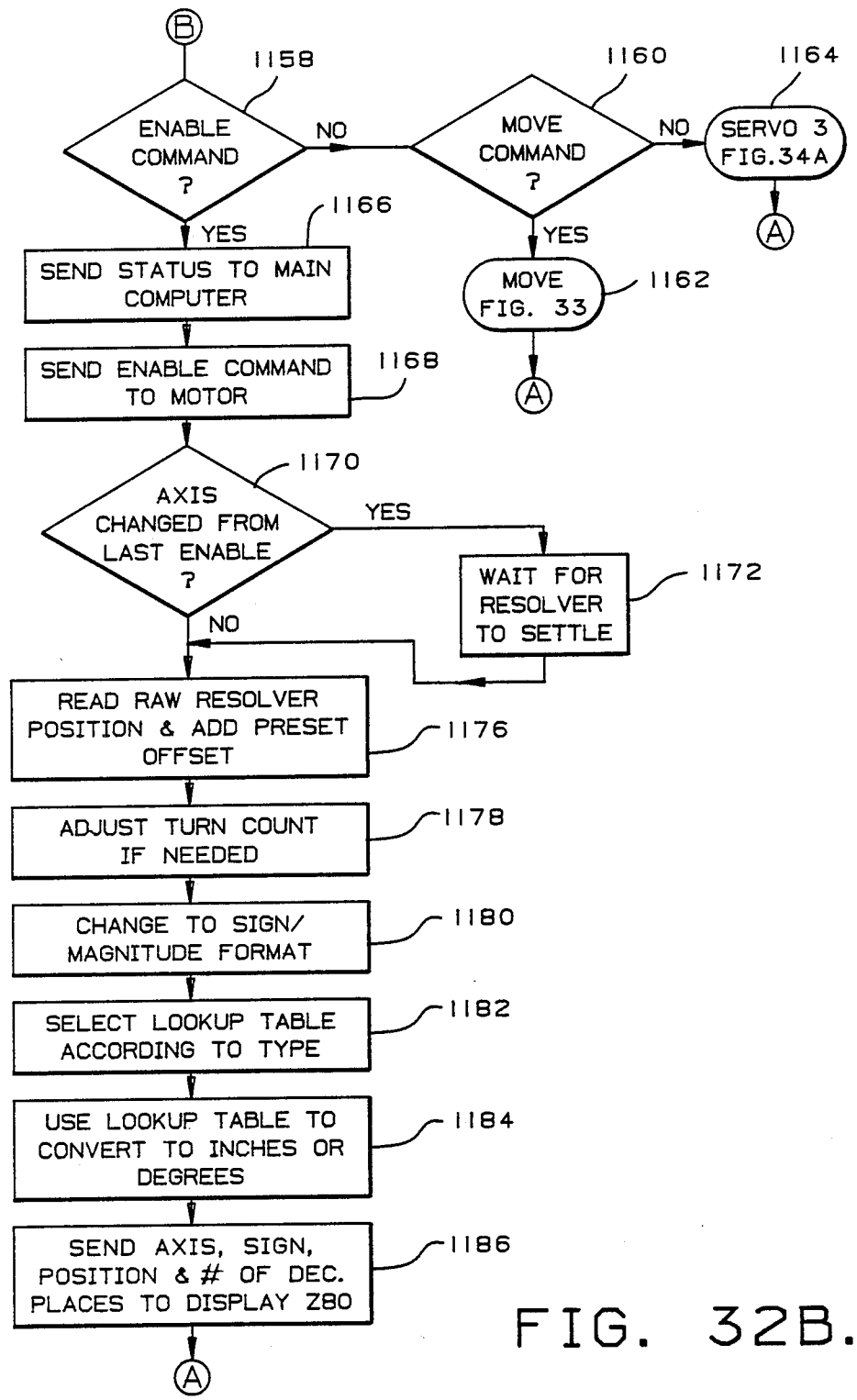
Figure 33:
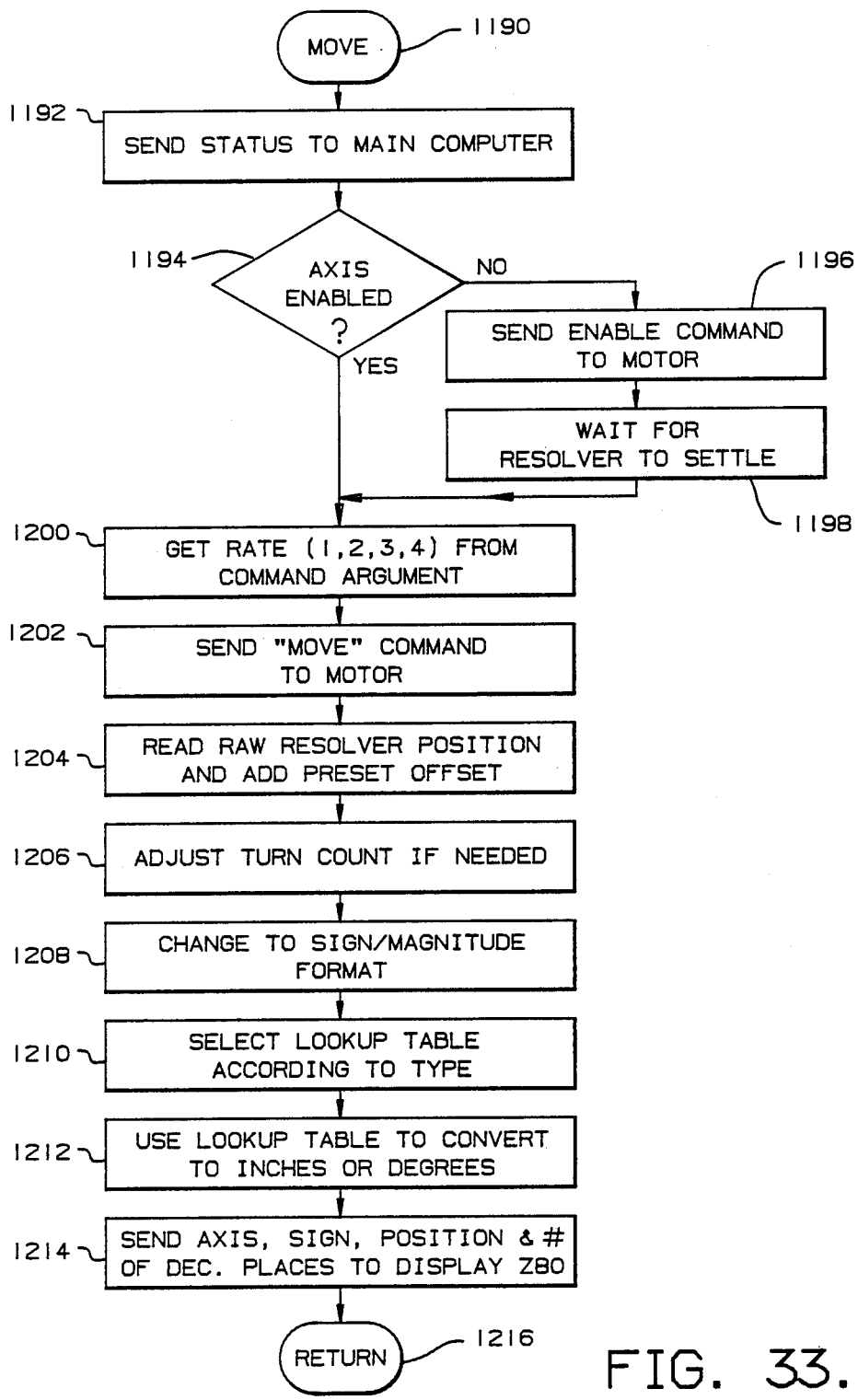
FIG. 33 is a move subroutine executed by the position processor 698.

The procedure executed by the position processor 698 is illustrated by FIGS. 32A-34. Referring to FIG. 32A, a clear status is first indicated 1142 to the control computer 692 followed by a setting 1144 of the old axis to none. Next a reset command is sent 1146 to the motor controller 702 to be executed by the motor computer 700 which stops any motion produced by the motor processor 700. The position computer 698 then reads 1148 the command axis and argument from the memory locations designated for communication between the control computer 692 and the position computer 698. The command is then tested 1150 and 1152, as previously discussed, to determine the type of command. Next, the control type or axis type is retrieved 1154 and tested 1156 to determine whether it is a legal type. This test 1158 and 1160 is performed because the control computer 692 can reload the table at any time for specialized types of motions. The command is then tested to determine whether it is an enable command or a move command. If it is a move command, the procedure of FIG. 33 is executed and if it is not a move command or an enable command, then the servo procedure of FIG. 34 is executed. If it is an enable command, the status is sent 1166 to the control computer 692 followed by the transmission 1168 of an enable command to the motor processor 700. If the axis designated since the last enable command has changed, the position processor 698 waits 1172 for approximately 0.5 seconds to allow the resolver conversion circuit 784 to accurately determine the position of the new axis. After the resolver conversion circuit 784 has settled, the raw resolver position is adjusted 1176 with a preset/offset which aligns the resolver position with the true position. If the resolver position indicates that a complete turn of the resolver has occurred, a turn count is adjusted 1178 by incrementing or decrementing in accordance with the direction. Resolver positions are divided into quadrants and the saved previous quadrant is compared to the current quadrant to determine turn count changes. The resolver position is then changed 1180 to a sign magnitude format and the lookup table for the position for the type axis is determined 1182. The lookup table is used 1184 to convert the turn count and adjusted resolver position into degrees or inches as required. The position processor then sends the axis, sign, and position and number of decimal places to the display processor.

The move subroutine, executed when the move command is received, is illustrated by FIG. 33. First the move status is sent 1192 to the control computer 692 through the status register after which a determination is made 1194 concerning whether the particular axis has been enabled. If not, the enable command is sent 1196 to the motor computer 700 after which a wait occurs for the resolver conversion circuit to settle. When the resolver conversion circuit has settled, the speed or rate is retrieved 1200 from the command argument in the appropriate portion of the position computer memory accessible by the control computer 692 and the move command is sent 1202 to the motor computer 700. Then the resolver position is read, turn count adjusted 1206, the format is converted and the conversion is performed to send the position to the display processor 724 as discussed with respect to the enable command.

Figure 34A:
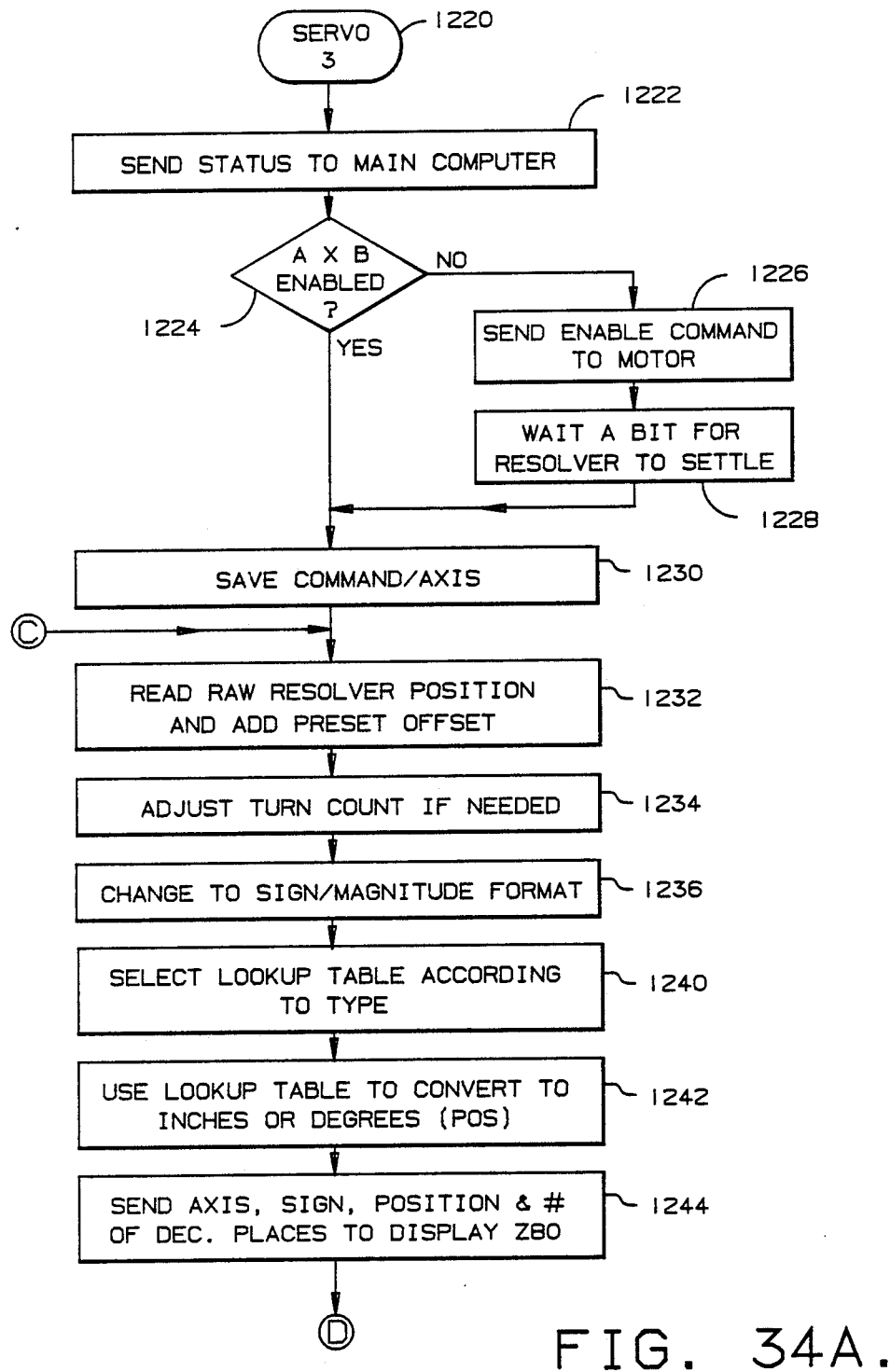
Figure 34B:
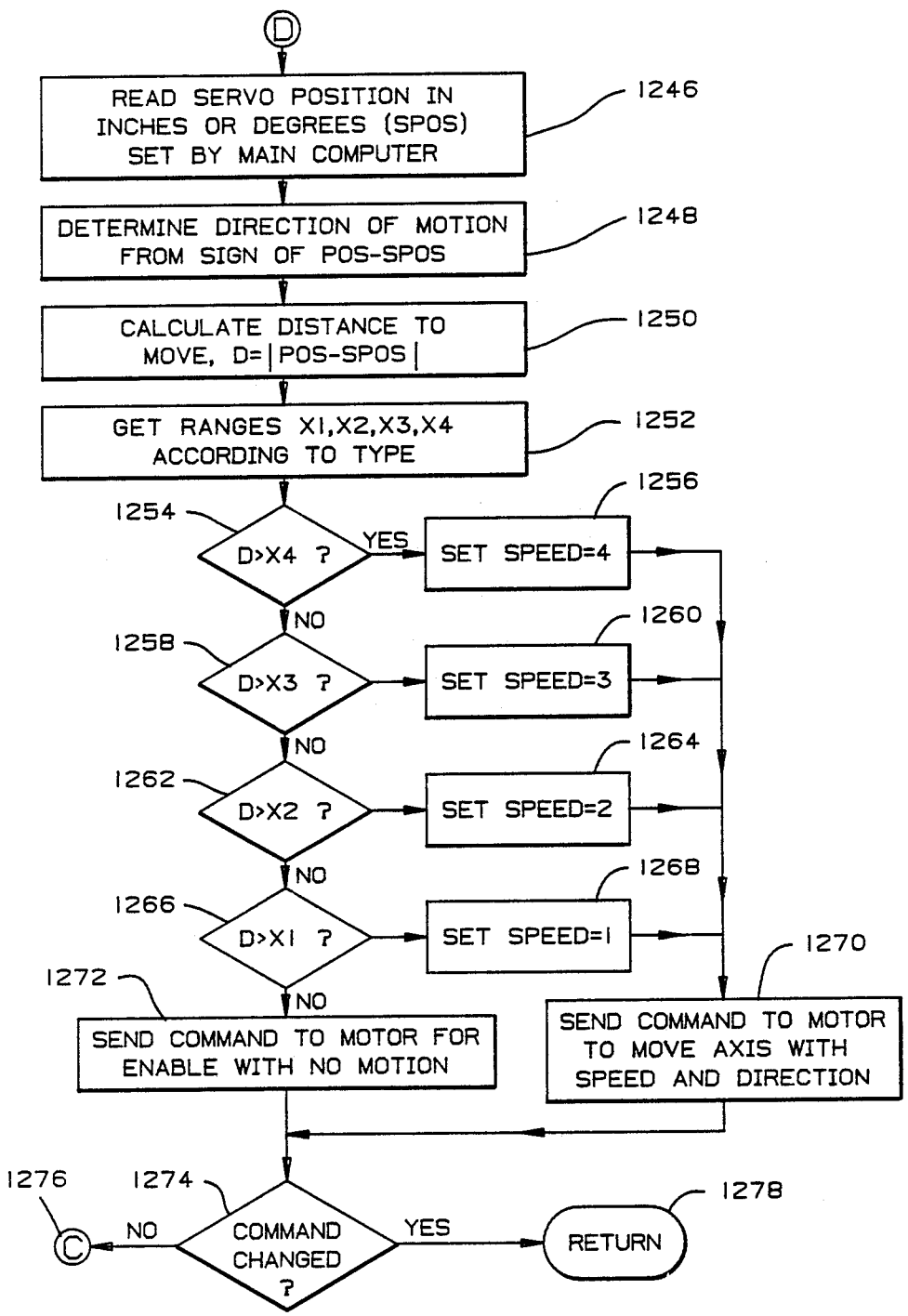

When the command from the control computer 692 is not the enable command or the move command, it must be the servo command and, as a result, the procedure of FIGS. 34A and 34B is performed. The servo control procedure starts by sending 1222 the servo control status to the control computer 692. Next, the position computer 698 determines whether the axis being controlled has been enabled and if not, sends 1226 the enable command to the motor processor 700 and waits 1228 for the resolver conversion unit on the resolver converter 720 to settle. Next the command and the axis being controlled are saved 1230. The command and axis are saved because the positioning loop, discussed below, is continuously executed to maintain the desired position. During this loop the resolver position is read 1232 adjusted by the reference offset followed by an adjustment 1234 of the turn count, if necessary. As in previously discussed procedures, the format of the resolver position and turn count is changed to sign magnitude after which the lookup table is used to convert to the appropriate measurement followed by the transmission of the axis, sign, position and number of decimal places to the display computer 724. The procedure continues by reading the desired servo position in inches and degrees from the position computer memory area set aside for communication from the control computer 692. The direction of motion is determined 1248 by comparing the current position with the desired position. The movement distance is then calculated 1250 after which the distance is compared to the appropriate ranges. When the distance falls within a particular range, the speed is determined and a command which consists of speed and a direction is sent to the motor processor 700. The use of different speeds for different travel distances allows the speed to be decreased as the target position is approached, thus, preventing overshoot. If the distance from the current position to the desired position is less than the smallest range, then the desired position is satisfied to within the specified position resolution and the enable command is sent to the motor processor 700 which enables the motor processor 700 without indicating any motion. Next, the saved command and axis is compared 1274 with the command area accessible by the control computer. If the commands are the same then servo positioning continues. If not, a return to the procedure of FIG. 32 is performed.

The following discussion concerns control of the drive box 52 by the control system illustrated in FIG. 25 using the position 798 and motor 800 processors of the appropriate axis.

Figure 35:
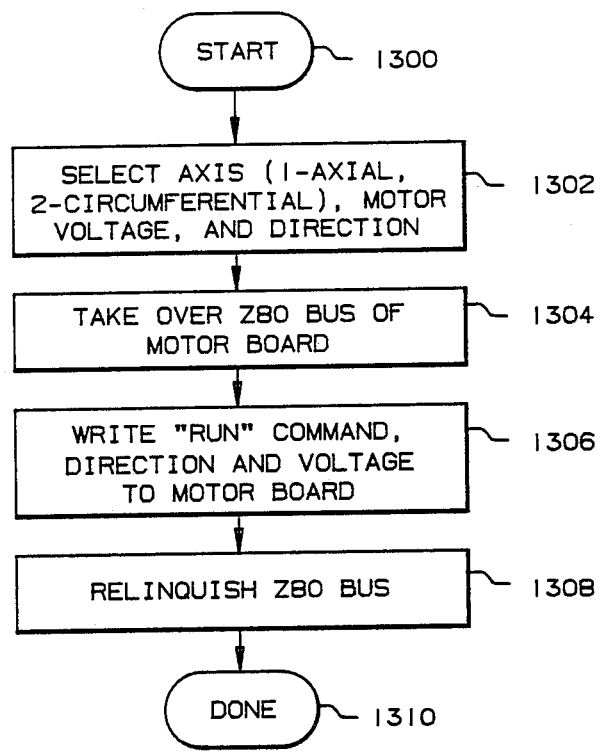
FIG. 35 is a flowchart of a procedure executed by the control computer 692 for continuous motion of the axial or circumferential axes.

If a scan control routine or an operator desires to perform a continuous motion the procedure of FIG. 35 is executed. In this procedure, as in the continuous motion procedure for the scan head, the axis is selected 1302 followed by the seizure of the motor processor 800 after which the run command indicating the direction and voltage is stored in the motor processor 800. Once the command has been transferred, the bus is relinquished 1308. Once a run command is transferred to the motor computer 800, the motor will continue to run until the run command is replaced by an idle command or a servo command or until the motor computer 800 is reset.

Figure 36:
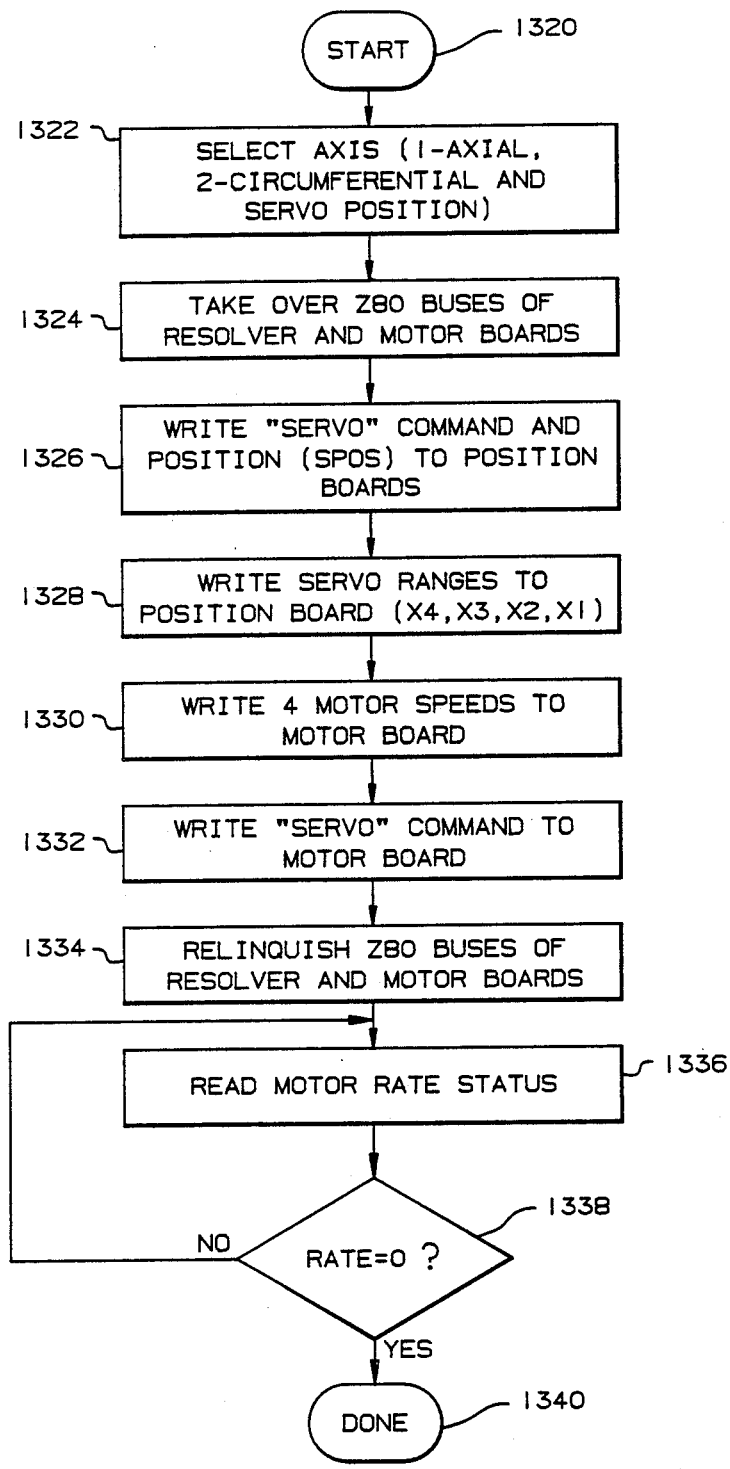
FIG. 36 is the procedure performed by the control computer 692 to initiate axial or circumferential servo control.

When the control computer 692 executes servo control, the procedure of FIG. 36 is executed. This procedure is started by selecting 1322 the desired axis and seizing 1324 the buses of the position computer 798 and the motor computer 800. The servo command is transferred 1326 to the position processor 798 by loading the appropriate memory area. Next, the servo ranges and corresponding speeds, as shown by Table 2 below are written into the memory of the position processor 798 and motor processor 800.

TABLE 2

|  | Scale Factor | Range 1 | Speed 1 | Range 2 | Speed 2 |
|---|---|---|---|---|---|
| Circumferential | 360° | 1° | 10 | 2° | 71 |
| Axial | 4.7123 | .001" | 10 | .005" | 71 |

|  | Range 3 | Speed 3 | Range 4 | Speed 4 |
|---|---|---|---|---|
| Circumferential | 8° | 132 | 15° | 255 |
| Axial | .02" | 132 | .05" | 255 |

The servo command is transferred 1332 to the motor processor 800 after which the buses are relinquished 1334. The status of the motor is then monitored until the speed reaches 1338 zero. The position 798 and motor 800 processors will continue to operate under the servo command until the servo command is replaced with the idle command or the run command, or the position and motor processors are reset.

Figure 37:
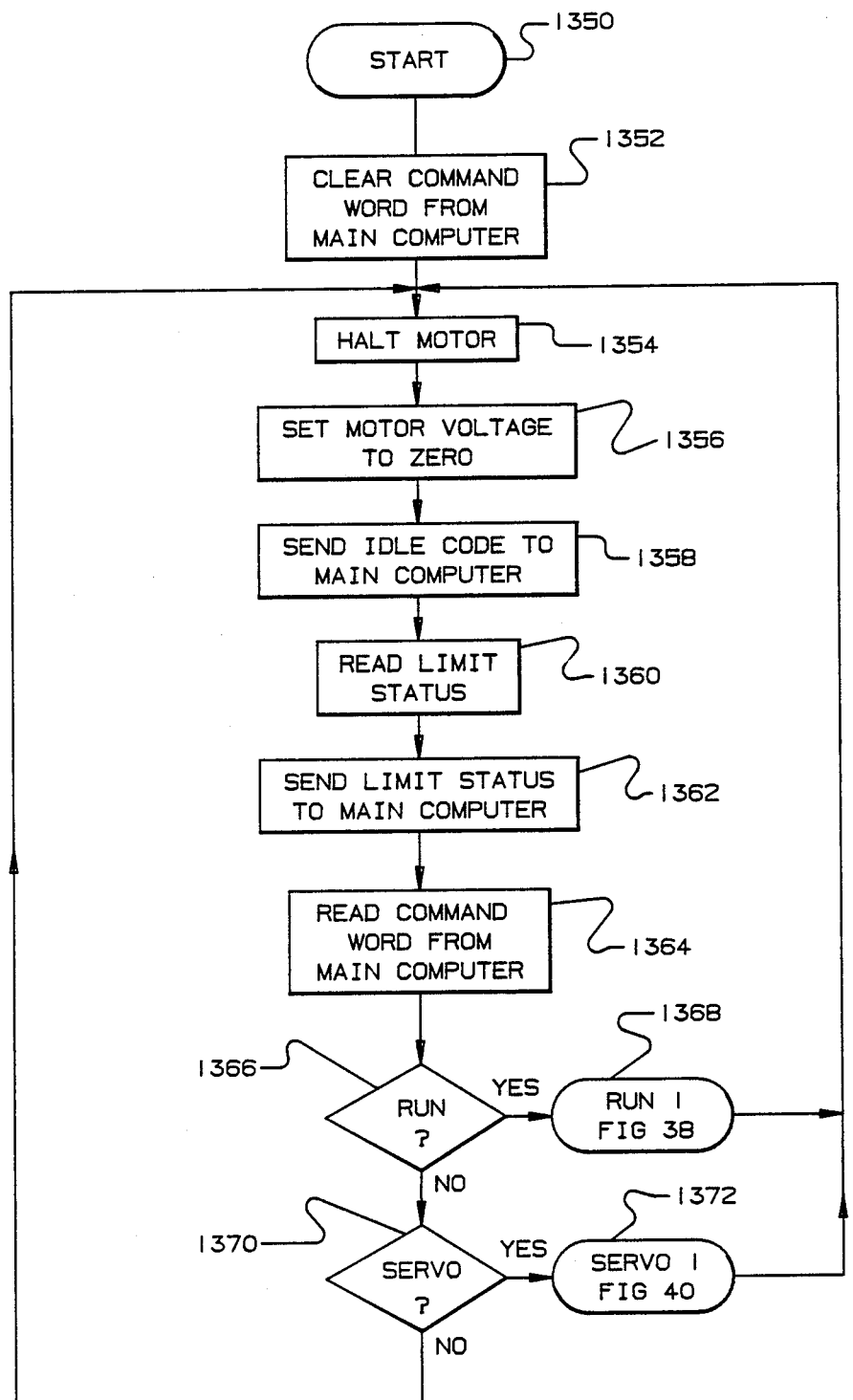
FIG. 37 is part of the procedure executed by either the axial or circumferential motor processor 772 when a command is received.
Figure 38:
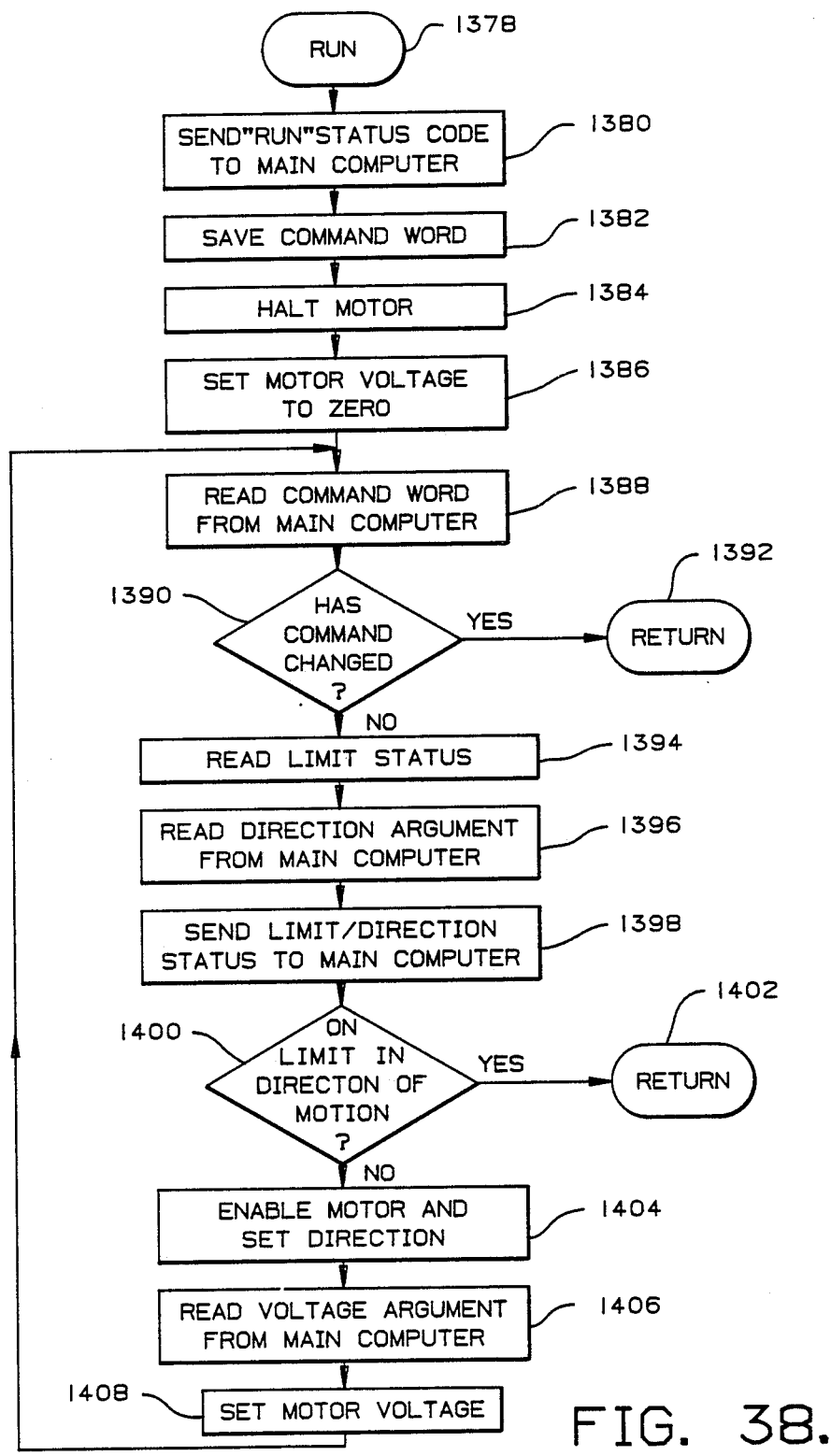
FIG. 38 is a run subroutine called by the procedure of FIG. 37.
Figure 39:
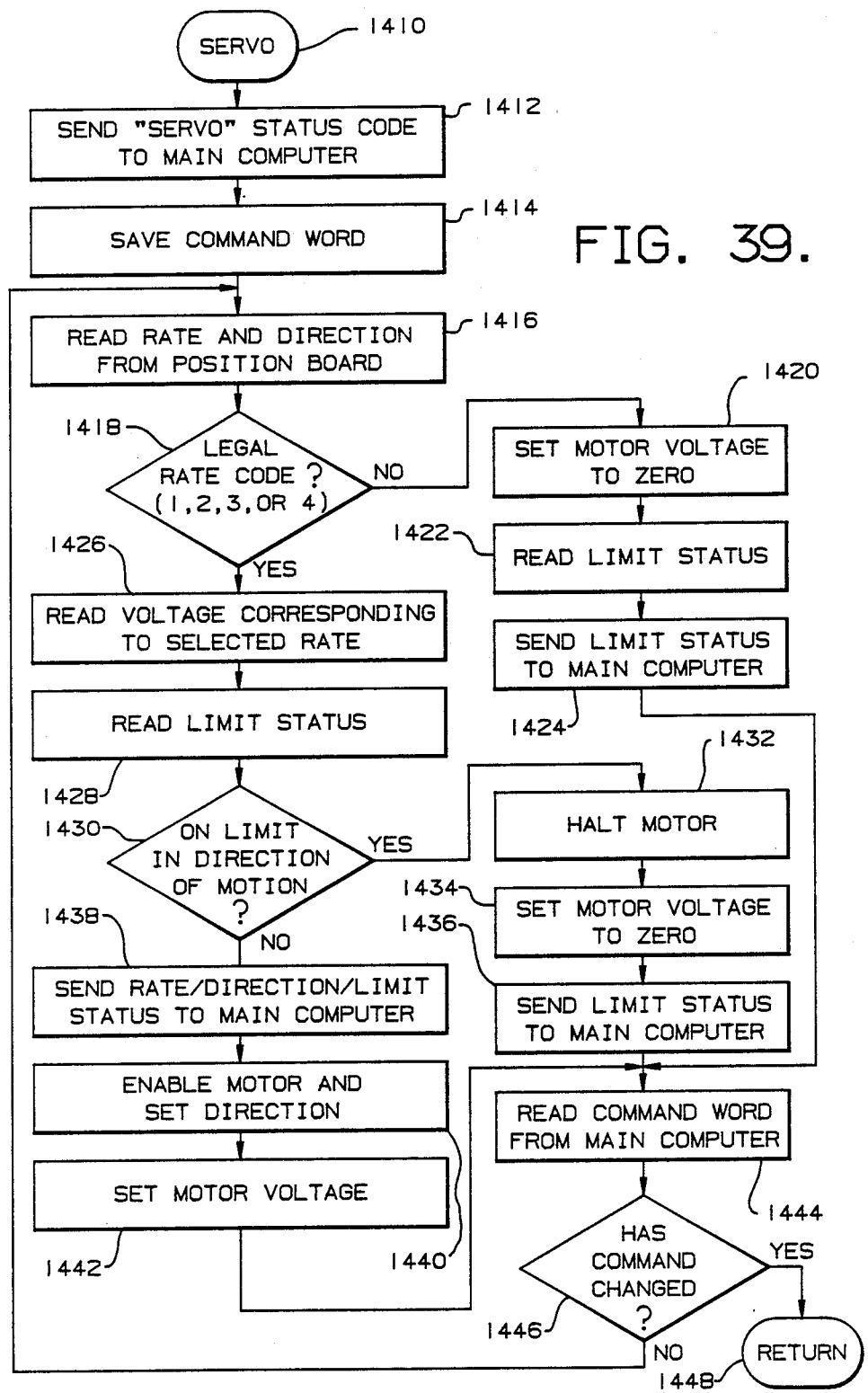
FIG. 39 is a servo subroutine executed called the procedure of FIG. 37.

When the motor computer 800 receives a command, the procedure of FIGS. 37-39 are executed. The procedure starts by clearing the command word in the processor memory which can be loaded by the main computer 692 after which the motor is halted 1354 by transmitting a halt command to the motor controller 804. Next, the motor voltage is set 1356 to zero by loading the speed register, followed by the transmission of an idle status code to the control computer 692. Next, the limit status of the limit switches is read 1360 followed by a transfer 1362 of the limit status to the control computer 692 through the status register. A command is read 1364 from the memory set aside for access by the control computer 692 and determinations are made as to whether the command is a run command or a servo command. If it is a run command the procedure of FIG. 38 is performed, and if it is a servo command, the procedure of FIG. 39 is performed.

The run procedure of FIG. 38 starts by sending 1380 a run status code to the control computer 692 after which the command is saved 1382. The motor is then halted 1384 and the motor voltage set to zero 1386. The command is then read 1388 from the memory again and compared 1390 with the save command. If the command has changed then a return to the procedure of FIG. 37 is performed. If the command has not changed the limit status is read 1394 followed by the direction arguments, supplied by the control computer 692. Then the limit and direction status is transmitted to the control computer 692 followed by a determination 1400 as to whether the limit has been reached in the particular direction of motion. If the limit has been reached the command is ignored and a return 1402 to the procedure of FIG. 37 occurs. If the limit has not been reached, then the motor is enabled and the direction is set 1404. Next, the voltage argument or speed argument is read 1406 from the control computer 692 accessible memory location and loaded 1348 into the speed register.

When the servo control command is being executed, the procedure of FIG. 39 is performed by the motor computer 800. First, the servo status is transmitted 1412 to the control computer 692 after which the command word is saved 1414. The rate and direction are read 1416 from the position processor accessible latch after which the rate code is compared 1418 to determine whether it is a legal code. If it is not a legal code, the motor speed is set 1420 to zero after which the limit switch status is read 1422 and sent to the control processor 692. If it is a legal code, the voltage for the rate is read 1426 from an internal table, loaded during the procedure of FIG. 36, according to the designated rate. The limit status is then read 1428 after which a determination 1430 is made concerning whether the limit of movement has been reached in the particular direction of motion. If the limit of movement has been reached, a halt command is sent 1432 to the motor controller 804 after which the motor voltage is set to zero and a status code is sent 1436 to the control computer 692 indicating that the limit of movement has been reached in the particular direction of motion. If the limit has not been reached, status codes for the rate, direction and limit position are sent 1438 to the control computer 692 followed by enabling 1440 of the motor and direction accompanied with the loading 1442 of the motor voltage into the speed register. Next, the command area of the memory is read 1444 to determine 1446 whether the command has changed. If the command has changed a return to the procedure of FIG. 37 is performed. If not, the servo control loop is executed again.

Figure 40:
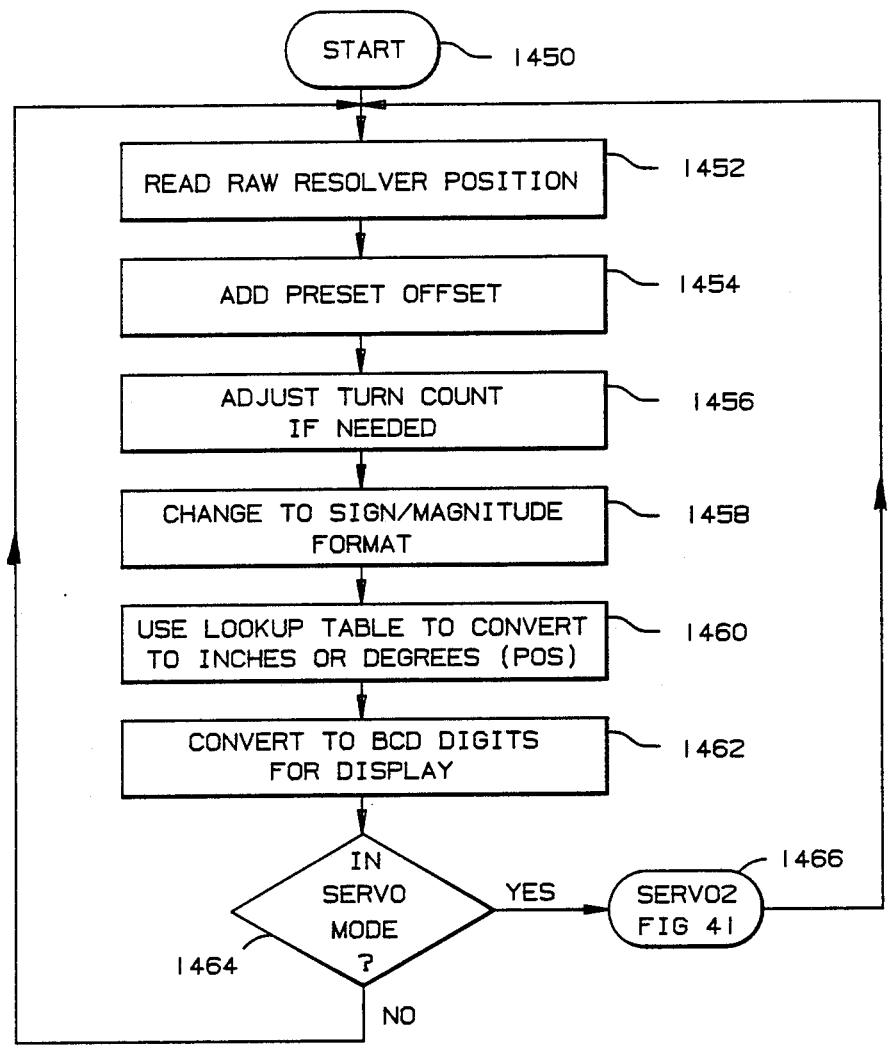
FIG. 40 is part of the procedure performed by either the axial or circumferential position processor 770 when motor control is being executed.
Figure 41:
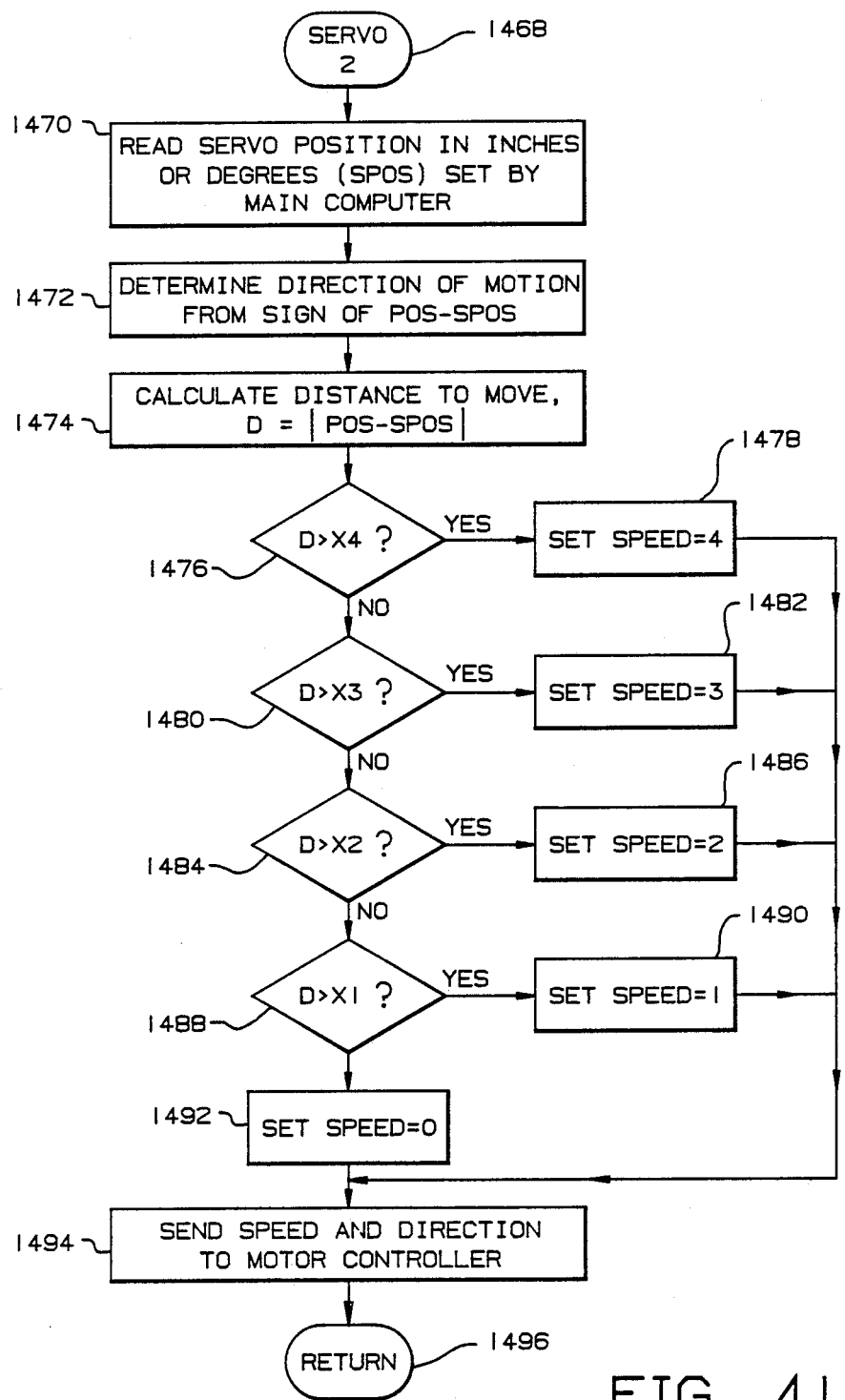
FIG. 41 is a subroutine called by the procedure of FIG. 40.

During the motion control procedure performed by the motor processor 800 the position processor 798 is executing the procedures of FIGS. 40 and 41. The position computer procedure starts by reading 1452 the resolver position and adding 1454, to the resolver position, an offset which aligns the resolver position with a reference position. If the resolver position has crossed a turn threshold, the turn count is adjusted 1456. Next, as in previous procedures, the position is converted 1458 into a sign magnitude format after which the position is converted 1460 into inches or degrees according to the scale factors of Table 2, as required for display 1422 1462 on the panel display 815. A determination 1464 is made concerning whether the mode is the servo mode and if not, the position output loop is executed again. If it is the servo mode, the procedure of FIG. 41 is executed.

At the beginning of the servo procedure of FIG. 41 executed by the position computer 798, the servo position designated by the main processor is read 1470 from the appropriate memory location in the memory of the position computer 798. The direction is determined 1472 followed by calculation 1474 of the absolute value of the distance. The distance is then compared with the appropriate ranges and an appropriate speed or rate is set. When the speed has been determined, it is sent, along with the direction, to the motor control unit 802 processor 772 followed by return to the procedure of FIG. 40.

Prior to transducer calibration, operating reference points for the chucks, radial support assemblies, transducer tilt (rotation), axial position and circumferential position must be determined by using reference fixtures and storing the associated positions at which the fixtures are engaged. The offsets between chucks and the various transducers can be determined during calibration using measurement devices to obtain offsets to within 0.01 inches.

As discussed in the related applications identified in the cross references section, the transducers must be calibrated so that reflections located during an inspection scan can be accurately determined as to their location within the rotor being inspected. The calibration starts by mounting the ranging and inspection transducers so that their beams are coincident on the same circumferential location in a calibration block. How a calibration ranging scan is performed during which the ranging offset average times are recorded and the ranging curve is loaded into the flaws, is discussed in more detail in the related application entitled Ultrasonic Signal Processing System Including a Flaw Gate.

Figure 42:
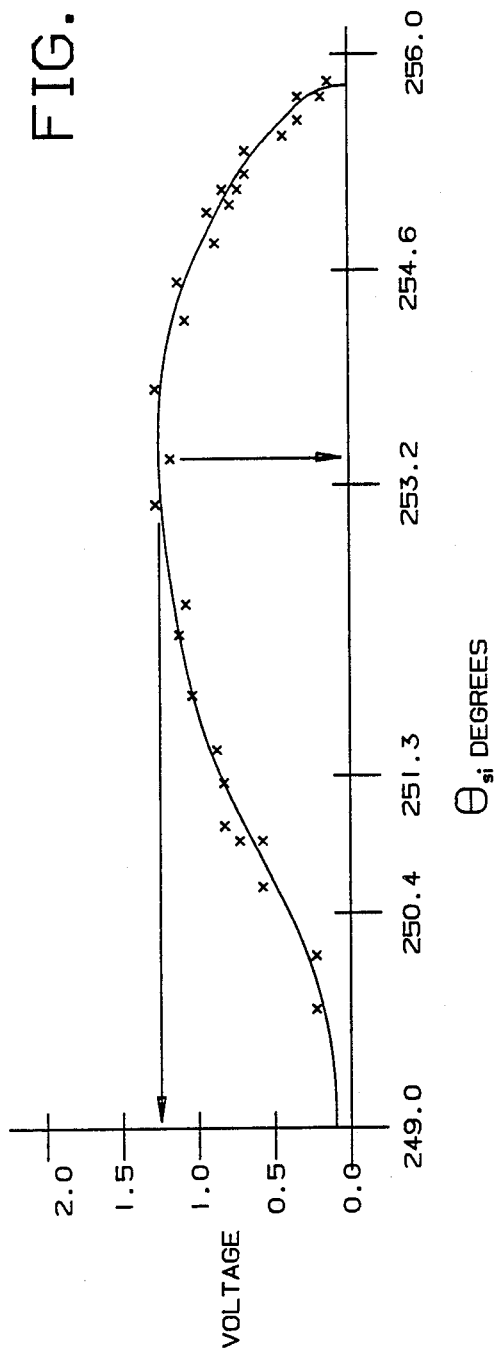
FIGS. 42 and 43 depict curve fitting procedures performed during transducer calibration to calibrate reflector angle and depth.
Figure 43:
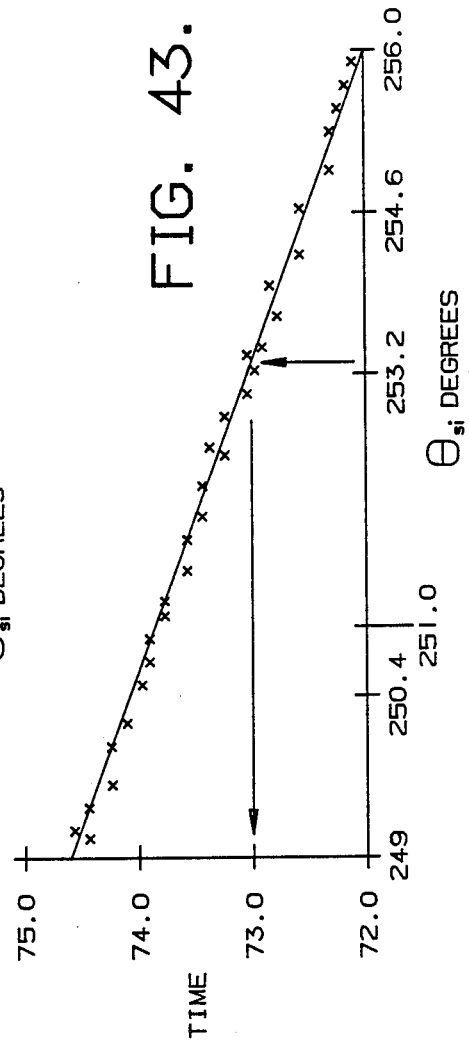

When the ranging scan by the ranging transducer is completed, the inspection transducer is moved into the calibration block and data is recorded from side drilled holes. The data from the known location side drilled holes can be used to manually select the peak signal and enter a circumferential position, time, amplitude and attenuation for the particular side drilled hole. As an alternative, the data can be applied to a curve fitting routine which produces a curve, as illustrated in FIG. 42. The curve can be used to determine the amplitude voltage and the angle at which the peak voltage occurs. The transit times for the reflection from the hole can also be applied to a curve fitting routine to produce a curve, as illustrated in FIG. 43. The angle obtained from the curve of FIG. 42 can be used to determine a measured reflection time using the curve of FIG. 43. The measured angle and measured transit time are then used in the calculations discussed below to determine the operating point of the transducer for the particular hole. From the time and amplitude data for the side drilled holes, the threshold curves, discussed in the related application entitled Ultrasonic Signal Processing System Including a Flaw Gate, are created for time windows corresponding to the side drilled holes which fall within a particular depth window. It is also possible to use the curve fitting procedure of the present invention with round bottomed holes to adjust not only circumferential position and reflection time but axial offset and tilt using the procedures discussed herein.

During an operating point calibration, suppose we have data from N holes, where N must be no smaller than three. For the $i^{th}$ hole, we have: $d_i$—known hole depth; $\Theta_i$—known hole angular position; $t_i$—measured time of peak echo from hole as determined from FIG. 43; $\Theta_{si}$—measured circumferential scanner position at the peak echo as determined from FIG. 42. If we define $\Theta_i = \Theta_i - \Theta_{si}$, then the operating point parameters for a particular window are: $\phi_2$—refracted angle; $t_1$—surface time; $V_2$—metal velocity; and $\Theta_{off}$—circumferential offset. The following ray model calculations are then used to determine the operating point parameters:

$$\Delta\theta_i = \theta_{off} + \phi_2 - \left[ \frac{r_b}{r_b + d_i} \sin\phi_2 \right].$$

where $r_b$ equals the radius of the bore;

$$t_i = t_1 + \frac{P_2^i}{V_2}$$

where $P_2^i$ is the path length in the metal from the surface to the hole, and $$P_2^i = \frac{\sin(\phi_2 - B_i)}{\sin\phi_2} (r_b + d_i)$$

where $B_i = \sin^{-1}\left[ \frac{r_b}{r_b + d_i} \sin\phi_2 \right]$

The computer then solves for $\Theta_{off}$ and $\phi_2$ by minimizing the error $E_1$, $$E_1 = \sum_{i=1}^{N} \left\{ \Delta\theta_i - \theta_{off} - \phi_2 + \sin^{-1}\left[ \frac{r_b}{r_b + d_i} \sin\phi_2 \right] \right\}^2$$

setting $\frac{\partial E}{\partial \theta_{off}} = \frac{\partial E}{\partial \phi_2} = 0$ and obtaining $$\sum_{i=1}^{N} \left\{ \Delta\theta_i - \frac{1}{N}\left( \sum_{m=1}^{N} \Delta\theta_m + \sum_{m=1}^{N} \sin^{-1}\left[ \frac{r_b}{r_b + d_m} \sin\phi_2 \right] \right) + \sin\left( \frac{r_b}{r_b + d_i} \sin\phi_2 \right) \right\} \frac{\cos\phi_2}{\left[ \left( \frac{r_b + d_i}{r_b} \right)^2 - \sin^2\phi_2 \right]^{\frac{1}{2}}} =$$

$$F(\phi_2) = 0$$

This equation is solved for $\phi_2$ using the bisection method. This is a well known method and is discussed in the book "Computer Methods for Mathematical Computations" by Forsythe, Malcolm and Moler. Then, $$\theta_{off} = \frac{1}{N}\left\{ \sum_{i=1}^{N} \Delta\theta_i + \sum_{i=1}^{N} \sin^{-1}\left( \frac{r_b}{r_b + d_i} \sin\phi_2 \right) \right\} - \phi_2$$

The computer then solves for $t_i$ and $V_2$ by minimizing $E_2$, $$E_2 = \sum_{i=1}^{N} \left( t_i - t_1 - \frac{P_2^i}{V_2} \right)^2$$

$$V_2 = \frac{\sum_{i=1}^{N} (P_2^i)^2 - \frac{1}{N}\left( \sum_{i=1}^{N} P_2^i \right)^2}{\sum_{i=1}^{N} (t_i P_2^i) - \frac{1}{N}\left( \sum_{i=1}^{N} t_i \right)\left( \sum_{i=1}^{N} P_2^i \right)}$$

$$t_i = \frac{1}{N}\left( \sum_{i=1}^{N} t_i - \frac{1}{V_2} \sum_{i=1}^{N} P_2^i \right)$$

If the operating point is determined, and it is not as desired by the operator, the transducer mounting can be adjusted and the procedure repeated to obtain the desired operating point for the channel/window of interest. The times $t_i$ and amplitudes of the reflections for each hole within each window are used to create threshold curves used to determine whether a signal contains reportable indications. The threshold procedure is discussed in more detail in the related application entitled Ultrasonic Signal Processing System Including a Flaw Gate and is not discussed further herein.

After the operating point calibration procedure discussed above is performed, the scan head is moved into a rotor bore to perform an inspection. At the beginning of each scan for each axial position, a ranging scan is performed using the ranging transducer in which adjusted delays for the surface time are determined and loaded as curves into the flaw gates discussed in detail in the related application entitled Ultrasonic Signal Processing System Including a Flaw Gate. The preferred high speed scan method produces separate pulses focussed in the center of each depth/time window that are rapidly generated to provide complete coverage of the first four to six inches of the rotor during high speed circumferential motion. The flaw gates then record hit data which include a range corrected reflection time, a scanner angle and the amplitude. The control computer 692 then retrieves the data from the flaw gates and performs the calculations below necessary to pinpoint the depth, angle and axial position of each flaw indication.

The time in microseconds, for each reflection is calculated from an integer waveform index provided by the flaws gate, $$T_{raw} = 0.05(\text{index}) + \text{delay}$$

where 0.05 is the sampling interval in microseconds, and the delay equals the transit time delay of the flaw gate. The waveform index is corrected by a ranging offset in the flaw gate, as discussed in the related application. Next the time T and circumferential position C are converted to depth D and angle $\Theta$ according to the following calculations:

$$P_2 = \tfrac{1}{2} V_2 (T - t_1)$$

where $P_2$ equals the path length in the metal; $V_2'$ equals the sound velocity in the metal; and $t_1$ is the surface time; that is, the time for the inspection pulse to reach the bore surface 26 and return; and then, $$D = \sqrt{P_2^2 + r_b^2 + 2P_2 r_b \cos \phi_2} - r_b$$

where $\phi_2$ is refracted angle and $r_b$ is the bore radius $$\theta = C + \theta_{off} + \phi_2 - \sin^{-1}\left[\frac{r_b}{r_b + D} \sin\phi_2\right]$$

Recall that $V_2$, $t_1$, $\phi_2$ and $\Theta_{off}$ are the constants determined during calibration. True axial position Z is then calculated from scanner axial position APOS $$Z = APOS - AXOFF$$

where AXOFF is the transducer mounting offset. If round bottom holes were used during calibration to determine any tilt of the beam, the true axial position is adjusted using $$Z = APOS - AXOFF + \alpha D$$

where $\alpha$ equals slope and D equals depth.

Figure 45:
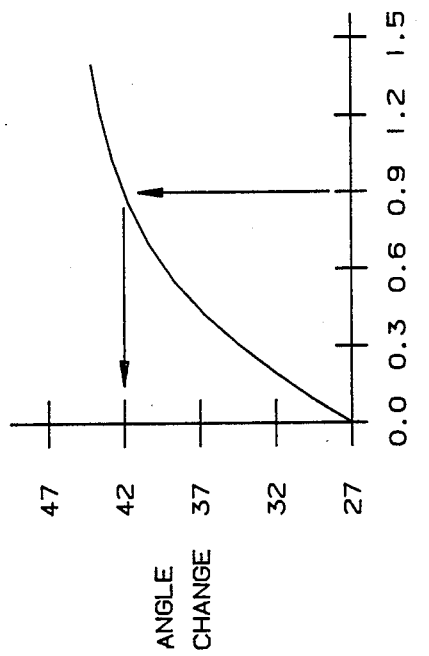
FIGS. 44 and 45 illustrate a procedure for locating the position and depth of flaws during an inspection.
Figure 44:
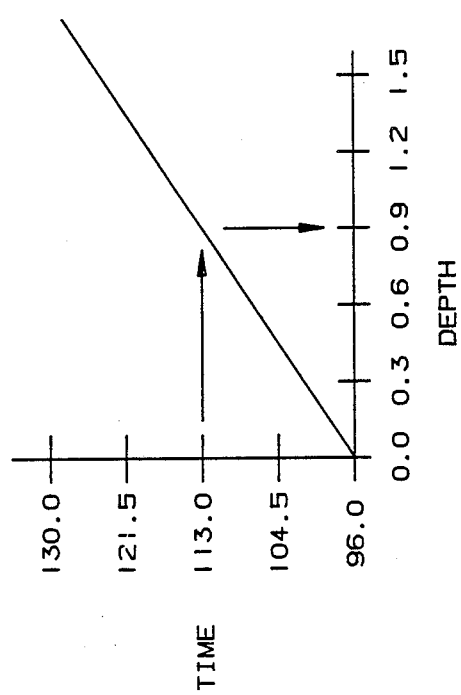

In the alternative to the calculations discussed above, it is possible to use table lookup methods to determine the depth from the reflection time using a curve, as illustrated in FIG. 44, stored in a time to depth conversion table. The depth is then used to produce an angle change from a depth to angle change conversion table which represents a curve, as illustrated in FIG. 45. Once the depth, angle of the flaw and true axial position are determined, a known graphic display program can be used to provide an image of the indication in several different views such that the size and location of the flaws within the rotor can be determined. Rotor life time predictions can then be made based on size and location of flaws.

The many features and advantages of the invention are apparent from the detailed specification and thus it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described and accordingly, all suitable modifications and equivalents may be resorted to, falling within the scope of the invention. For example, the preferred transducer is a variable focus array transducer, however, a plurality of fixed focus transducers can be substituted therefore. The refracted angle of the shear beam within the rotor material is preferably 40 to 60 degrees, however, other angles could be used with good success. It is also possible to provide the transducer carriage of the present invention with a spring loaded transducer which can contact the rotor bore. In such a situation, a proximity switch would be used to indicate that the transducer is in actual contact with the bore. The present system has been described with respect to preferred planes of propagation, refracted angles, propagation mode and water path lengths; however, other values for these parameters can be used. It is also possible to use the present invention in a partial immersion configuration whereby a stream of fluid is projected from the transducer to the bore surface. The preferred method of performing transducer scans is alternate 360 degree scan rotations at fixed axial positions, however, it is possible to perform helical scanning rather than the fixed slice axial position scan.

What is claimed is:

1. An ultrasonic inspection system for a rotor having a bore, comprising:
    scan means for carrying a positionable inspection transducer into the bore without allowing the transducer to contact the bore surface and producing a shear inspection beam in the rotor;
    positioning means for holding the scan means substantially in the center of the bore;
    a drive rod coupled to said scan means and coupling linear and rotational motion to the scan means;
    drive means, coupled to said drive rod, for providing the linear and either continuous or discontinuous rotational motion to said drive rod; and
    control means, coupled to the transducer and said drive means, for controlling the movements of the transducer and the motions provided by said drive means and providing a position of the transducer as an output.

2. A system as recited in claim 1, wherein said scan means holds the transducer at a radial offset from a center of said bore creating the shear beam in said rotor.

3. A system as recited in claim 2, further comprising:

transducer signal processing means for processing transducer signals and storing the position; and flaw location determination means for determining the position of flaws from the processed transducer signals and the position.

4. A system as recited in claim 3, wherein said control means rotates said scan means circumferentially during a scan and spirally between scans.

5. A system as recited in claim 4, wherein said transducer signal processing means stores processed transducer signals and corresponding circumferential positions during a scan.

6. A linear scan head carrying inspection transducers into a bore and driven by a drive rod, said scan head, comprising:
   inspection transducer stations coupled to each other and in which the inspection transducers are carried;
   transducer chuck stations coupled on both sides of the connected inspection transducer stations and centering the inspection transducer stations in the bore;
   a universal joint station, coupled to one of said transducer chuck stations at one end and allowing said transducer chuck stations to freely align said scan head;
   a front transducer station coupled to the other of the transducer chuck stations and carrying one of a mapping transducer and an inspection transducer; and
   a drive rod chuck station coupled to another end of the universal joint station and supporting the drive rod independently of the inspection transducer stations.

7. A scan head as recited in claim 6, wherein said inspection transducer stations include means for providing three axes of motion to the inspection transducer.

8. A scan head as recited in claim 6, wherein each of said transducer chuck stations include plural adjustable diameter means, separated axially along the transducer chuck station, for providing centering support to said scan head across bore diameter variations.

9. A scan head as recited in claim 6, wherein said universal joint station includes two hollow universal joints.

10. A scan head as recited in claim 6, wherein said front transducer station includes motion means for providing a first axis of motion for the transducers.

11. A scan head as recited in claim 10, wherein said motion means provides a second axis of motion for the transducers.

12. A scan head as recited in claim 6, wherein said front transducer station includes blind bore sensing means for sensing the end of a blind or plugged bore.

13. A mapping transducer station, comprising:
   blind bore sensing means for detecting the end of a blind or plugged bore;
   a mapping transducer frame coupled to said blind bore sensing means;
   radial motion means, coupled to the mapping transducer frame, for providing radial motion to the mapping transducer frame.

14. A station as recited in claim 13, wherein said radial motion means comprises:
   a geared rack coupled to said mapping transducer frame; and
   a rack guide slidably coupled to said geared rack, restricting lateral geared rack movement and allowing longitudinal motion.

15. A station as recited in claim 14, wherein said radial motion means further comprises:
   a gear box coupled to said geared rack;
   a motor coupled to said gear box; and
   a resolver coupled to said gear box.

16. A station as recited in claim 13, further comprising an air evacuation probe coupled to said radial motion means.

17. A chuck for a scan head positioned in a bore, said chuck comprising:
   four support arms having bore rollers for contacting the bore; and
   positioning means, coupled to said support arms, for holding the rollers at the same axial position in the bore and providing radial motion to said support arms to move the rollers either into contact with the bore or to a specified diameter, said positioning means comprising:
      support plates allowing radial movement of said support arms and restricting lateral movement;
      gear means, coupled to said support arms, for moving said support arms radially;
      a motor coupled to said gear means; and
      a resolver coupled to said gear means.

18. A chuck as recited in claim 17, wherein said chuck has a diameter and said positioning means includes means for allowing said support arms to contact a bore having a diameter greater than twice the diameter of said chuck.

19. A chuck as recited in claim 17, further including disengagement means for disengaging said positioning means from said support arms.

20. A chuck as recited in claim 19, wherein said support arms include gear racks, said positioning means includes a cluster gear coupled between said support arm gear racks and a motor, and said disengagement means comprises a pneumatically driven slide plate coupled to said cluster gear and decoupling said cluster gear from said support arm gear racks.

21. An inspection transducer station including an inspection transducer plate, said inspection transducer station comprising:
   rotation means for rotating the inspection transducer plate circumferentially;
   first radial motion means coupled to one end of said rotation means for providing a first radial motion to the one end; and
   second radial motion means coupled to the other end of said rotation means for providing a second radial motion to the other end.

22. A station, as recited in claim 21, wherein said rotation means comprises:
   a carriage coupled to said first and second radial motion means;
   a motor affixed to said carriage;
   a rotatable transducer bracket coupled to said motor and holding the inspection transducer; and
   a resolver coupled to said rotatable transducer bracket.

23. A station as recited in claim 21, wherein said first and second radial motion means each comprise:
   a geared rack coupled to said carriage;
   a rack guide slidably coupled to said geared rack, restricting lateral movement and allowing longitudinal motion;

a gear box coupled to said geared rack;
a motor coupled to said gear box; and
a resolver coupled to said gear box.

24. A motion control apparatus for a scan head held in position by an adjustable diameter chuck and carrying a positionable transducer, said scan head comprising a transducer station holding said positionable transducer and coupled to said chuck, said motion control apparatus comprising:
  scan head positioning means for controlling the diameter of the chuck and a radial position of the transducer;
  linear positioning means for controlling a linear position of the scan head; and
  rotational positioning means for controlling a rotational position of the scan head and providing the rotational position as a transducer rotational position output.

25. An apparatus, as recited in claim 24, further comprising transducer signal processing means for processing and storing transducer signals and storing the transducer rotational position output.

26. An apparatus as recited in claim 25, wherein said chuck includes a first motor for adjusting the diameter of the chuck and a first resolver providing resolver signals indicating chuck diameter and said scan head positioning means comprises:
  mechanical transducer motion means for moving the transducer, affixed to the scan head and the transducer and including a second motor and a second resolver providing signals indicating transducer position;
  first motor control means for controlling the first and second motors; and
  first position determination means for determining the positions from the resolver signals produced by said first and second resolvers, and providing the position of the transducer as a transducer scan head position output.

27. An apparatus as recited in claim 26, wherein said linear positioning means comprises:
  mechanical linear positioning means for moving the scan head linearly and including a third motor and a third resolver providing resolver signals indicating the linear position of the scan head;
  second motor control means for controlling said third motor; and
  second position determination means for determining position from the resolver signals produced by said third resolver and providing the linear position of said scan head as a scan head linear position output.

28. An apparatus as recited in claim 27, wherein said rotational positioning means comprises:
  mechanical rotation means for rotating the scan head and including a fourth motor and a fourth resolver providing resolver signals indicating the rotational position of the scan head;
  third motor control means for controlling the fourth motor; and
  third position determination means for determining position from the resolver signals produced by said fourth resolver and providing the transducer rotational position output.

* * * * *